United States Patent
Bissantz et al.

(10) Patent No.: US 8,309,734 B2
(45) Date of Patent: Nov. 13, 2012

(54) SUBSTITUTED PYRIDINES AS GPBAR1 AGONISTS

(75) Inventors: Caterina Bissantz, Village-Neuf (FR); Henrietta Dehmlow, Loerrach (DE); Rainer E. Martin, Basel (CH); Ulrike Obst Sander, Reinach BL (CH); Hans Richter, Grenzach-Wyhlen (DE); Christoph Ullmer, Fischingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/581,227

(22) Filed: Oct. 19, 2009

(65) Prior Publication Data

US 2010/0105906 A1    Apr. 29, 2010

(30) Foreign Application Priority Data

Oct. 29, 2008    (EP) .................... 08167791

(51) Int. Cl.
*C07D 213/63*    (2006.01)

(52) U.S. Cl. .......... 546/290; 540/593; 544/51; 544/105; 544/344; 544/353; 546/122; 546/167; 548/373.1; 548/469; 548/517; 548/560; 548/950; 549/510

(58) Field of Classification Search .................. 540/593; 544/51, 105, 344, 353; 546/122, 167, 290; 548/373.1, 469, 517, 560, 950; 549/510
See application file for complete search history.

(56) References Cited

FOREIGN PATENT DOCUMENTS

| EP | 0053011 | | 6/1982 |
|---|---|---|---|
| GB | 2087887 | * | 6/1982 |
| WO | 2004/085401 | | 10/2004 |
| WO | 2008/125627 | | 10/2008 |

OTHER PUBLICATIONS

Yang, et al. Journal of Translational Medicine, 6(42), 2008.*
Database Registry [Online] Chemical Abstracts Service Supplier: Enamine (2009) XP002561435 Accession No. 1181866-08-9.
Kawamata et al., *J. Biol. Chem.* 2003, 278, 9435-9440.
Maruyama et al., *Biochem. Biophys. Res. Commun.* 2002, 298,714-719.
Keitel, *Biochem. Biophys. Res. Commun.* 2008, 372, 78-84.
Keitel, *Hepatology* 2007, 45, 695-704.
Katsuma et al., *Biochem. Biophys. Res. Commun.* 2005, 329, 386-390.
Plaisancie et al., *J. Endocrin.* 1995, 145, 521-526.
Adrian et al., *Gut* 1993, 34, 1219-1224.
Kreymann et al., *Lancet* 1987, 2, 1300-1304.
Bojanowska et al., *Med. Sci. Monit.* 2005, 8, RA271-8.
Perry et al., *Current Alzheimer Res.* 2005, 3, 377-385.
Meier et al., *Diabetes Metab. Res. Rev.* 2005, 2, 91-117.
Watanabe et al., *Nature* 2006, 439, 484-489.

* cited by examiner

*Primary Examiner* — Douglas M Willis
(74) *Attorney, Agent, or Firm* — George W. Johnston; Dennis P. Tramaloni; Samuel H. Megerditchian

(57) ABSTRACT

This invention relates to novel phenyl amide or pyridyl amide derivatives of the formula

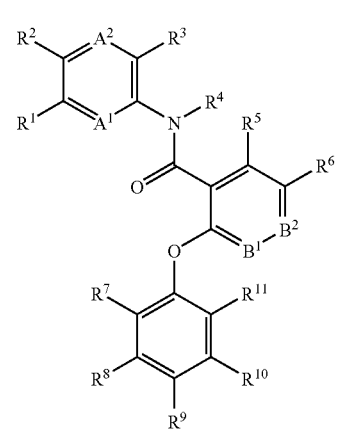

wherein $A^1$, $A^2$, $B^1$, $B^2$ and $R^1$ to $R^{11}$ are as defined in the description and in the claims, as well as pharmaceutically acceptable salts thereof. These compounds are GPBAR1 agonists and can be used as medicaments for the treatment of diseases such as type II diabetes.

3 Claims, No Drawings

SUBSTITUTED PYRIDINES AS GPBAR1 AGONISTS

PRIORITY TO RELATED APPLICATION(S)

This application claims the benefit of European Patent Application No. 08167791.6, filed Oct. 29, 2008, which is hereby incorporated by reference in its entirety.

FIELD OF THE INVENTION

The present invention is concerned with novel phenyl amide or pyridyl amide derivatives, their manufacture, pharmaceutical compositions containing them and their use as medicaments. In particular, the present invention relates to compounds of the formula

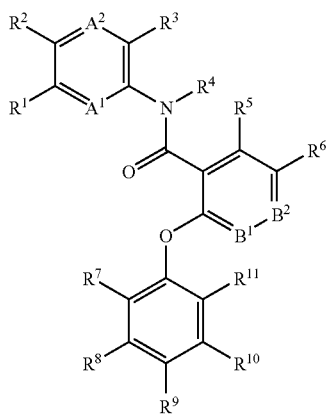

or pharmaceutically acceptable salts thereof.

The compounds of formula I possess pharmaceutical activity, in particular they are modulators or ligands of the GPBAR1 receptor. More particularly, the compounds are potent GPBAR1 agonists.

All documents cited to or relied upon below are expressly incorporated herein by reference.

BACKGROUND

Diabetes mellitus is an ever-increasing threat to human health. For example, in the United States current estimates maintain that about 16 million people suffer from diabetes mellitus. Type II diabetes also known as non-insulin-dependent diabetes mellitus accounts for approximately 90-95% of diabetes cases, killing about 193,000 U.S. residents each year. Type II diabetes is the seventh leading cause of all deaths. In Western societies, type II diabetes currently affects 6% of the adult population with world-wide frequency expected to grow by 6% per annum. Although there are certain inheritable traits that may predispose particular individuals to developing type II diabetes, the driving force behind the current increase in incidence of the disease is the increased sedentary lifestyle, diet, and obesity now prevalent in developed countries. About 80% of diabetics with type II diabetes are significantly overweight. Also, an increasing number of young people are developing the disease. Type II diabetes is now internationally recognized as one of the major threats to human health in the 21st century.

Type II diabetes manifests as inability to adequately regulate blood-glucose levels and may be characterized by a defect in insulin secretion or by insulin resistance. Namely, those who suffer from Type II diabetes have too little insulin or cannot use insulin effectively. Insulin resistance refers to the inability of the body tissues to respond properly to endogenous insulin. Insulin resistance develops because of multiple factors, including genetics, obesity, increasing age, and having high blood sugar over long periods of time. Type II diabetes, sometimes called mature on set, can develop at any age, but most commonly becomes apparent during adulthood. However, the incidence of type II diabetes in children is rising. In diabetics glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes is currently treated at several levels. A first level of therapy is through diet and/or exercise, either alone or in combination with therapeutic agents. Such agents may include insulin or pharmaceuticals that lower blood glucose levels. About 49% of individuals with Type II diabetes require oral medications, about 40% require insulin injections or a combination of insulin injections and oral medications, and 10% use diet and exercise alone.

Current therapies include: insulin secretagogues, such as sulphonylureas, which increase insulin production from pancreatic β-cells; glucose-lowering effectors, such as metformin which reduce glucose production from the liver; activators of the peroxisome proliferator-activated receptor γ (PPARγ), such as the thiazolidinediones, which enhances insulin action; and α-glucosidase inhibitors which interfere with gut glucose production. There are, however, deficiencies associated with currently available treatments. For example sulphonylureas and insulin injections can be associated with hypoglycemic episodes and weight gain. Furthermore, patients often lose responsiveness to sulphonylureas over time. Metformin and α-glucosidase inhibitors often lead to gastrointestinal problems and PPARγ agonists tend to cause increased weight gain and edema.

Bile acids (BA) are amphipathic molecules which are synthesized in the liver from cholesterol and stored in the gall bladder until secretion to the duodenum and intestine to play an important role in the solubilization and absorption of dietary fat and lipid-soluble vitamins. Approx. 99% of BA are absorbed again by passive diffusion and active transport in the terminal ileum and transported back to the liver via the portal vein (enterohepatic circulation). In the liver, BA decrease their own biosynthesis from cholesterol through the activation of the farnesoid X receptor alpha (FXRα) and small heterodimer partner (SHP), leading to the transcriptional repression of cholesterol 7α-hydroxylase, the rate-limiting step of BA biosynthesis from cholesterol.

GPBAR1, in the literature termed TGR5, M-BAR or BG37 as well, was recently identified as a G-protein coupled receptor (GPCR) responsive to BA (Kawamata et al., *J. Biol. Chem.* 2003, 278, 9435-9440; Maruyama et al., *Biochem. Biophys. Res. Commun.* 2002, 298, 714-719). GPBAR1 is a G(alpha)s-coupled GPCR and stimulation by ligand binding causes activation of adenylyl cyclase which leads to the elevation of intracellular cAMP and subsequent activation of downstream signaling pathways. The human receptor shares 86, 90, 82, and 83% amino acid identity to bovine, rabbit, rat, and mouse receptor, respectively. GPBAR1 is abundantly expressed in the intestinal tract, monocytes and macrophages, lung, spleen, placenta (Kawamata et al., *J. Biol. Chem.* 2003, 278, 9435-9440). BA induced receptor internalization, intracellular cAMP production and activation of extracellular signal-regulated kinase in GPBAR1-expressing HEK293 and CHO cells.

GPBAR1 was found to be abundantly expressed in monocytes/macrophages from humans and rabbits (Kawamata et al., *J. Biol. Chem.* 2003, 278, 9435-9440), and BA treatment suppressed LPS-induced cytokine production in rabbit alveolar macrophages and human THP-1 cells expressing GPBAR1. These data suggest that bile acids can suppress the macrophage function via activation of GPBAR1. In the liver functional GPBAR1 was found in the plasma membranes of Kupffer cells, mediating inhibition of LPS-induced cytokine expression (Keitel, *Biochem. Biophys. Res. Commun.* 2008, 372, 78-84), and of sinusoidal endothelial cells, where bile salts led to an increase in intracellular cAMP and to the activation and enhanced expression of the endothelial nitric oxide (NO) synthase (Keitel, *Hepatology* 2007, 45, 695-704). Furthermore, GPBAR1 has been detected in cholangiocytes of rat liver (Keitel, *Biochem. Biophys. Res. Commun.* 2008, 372, 78-84). Hydrophobic bile acids, such as taurolithocholic acid, increase cAMP in cholangiocytes suggesting that GPBAR1 may modulate ductal secretion and bile flow. In summary, GPBAR1 agonists may trigger a protective as well as medicative mechanism in cholestatic livers.

GPBAR1 is expressed in intestinal enteroendocrine cell lines from human (NCI-H716) and murine (STC-1, GLUTag) origin (Maruyama et al., *Biochem. Biophys. Res. Commun.* 2002, 298, 714-719). Stimulation of GPBAR1 by BA stimulated cAMP production in NCI-H716 cells. Intracellular increases in cAMP suggested that BA may induce the secretion of glucagon-like peptide-1 (GLP-1). Indeed, activation of GPBAR1 by BA promoted GLP-1 secretion in STC-1 cells (Katsuma et al., *Biochem. Biophys. Res. Commun.* 2005, 329, 386-390). Receptor-specificity has been demonstrated by RNA interference experiments which revealed that reduced expression of GPBAR1 resulted in diminished secretion of GLP-1. There is compelling evidence that GPBAR1-mediated GLP-1 release extends to in vivo. In the isolated vascularly perfused rat colon, BAs have been shown to trigger GLP-1 secretion (Plaisancie et al., *J. Endocrin.* 1995, 145, 521-526). In humans, intracolonic administration of deoxycholate showed marked increases in plasma levels of GLP-1 and the co-secreted PYY (Adrian et al., *Gut* 1993, 34, 1219-1224).

GLP-1 is a peptide secreted from enteroendocrine L cells has been shown to stimulate insulin release in glucose dependent manner in humans (Kreymann et al., *Lancet* 1987, 2, 1300-1304) and studies in experimental animals demonstrated that this incretin hormone is necessary for normal glucose homeostasis. In addition, GLP-1 can exert several beneficial effects in diabetes and obesity, including 1) increased glucose disposal, 2) suppression in glucose production, 3) reduced gastric emptying, 4) reduction in food intake and 5) weight loss. More recently, much research has been focused on the use of GLP-1 in the treatment of conditions and disorders such as diabetes mellitus, stress, obesity, appetite control and satiety, Alzheimer disease, inflammation, and diseases of the central nervous system. (see, for example, Bojanowska et al., *Med. Sci. Monit.* 2005, 8, RA271-8; Perry et al., *Current Alzheimer Res.* 2005, 3, 377-385; and Meier et al., *Diabetes Metab. Res. Rev.* 2005, 2, 91-117). However, the use of a peptide in clinical treatment is limited due to difficult administration, and in vivo stability. Therefore, a small molecule that either mimics the effects of GLP-1 directly, or increases GLP-1 secretion, may be useful in treatment of the variety of conditions or disorders described above, namely diabetes mellitus.

Furthermore, activation of GPBAR1 might be beneficial for the treatment of obesity and metabolic syndrome. Mice fed a high fat diet (HFD) containing 0.5% cholic acid gained less weight than control mice on HFD alone independent of food intake (Watanabe et al., *Nature* 2006, 439, 484-489). These effects were independent of FXR-alpha, and are likely to results from the binding of BA to GPBAR1. The proposed GPBAR1-mediated mechanism is leading to the subsequent induction of the cAMP-dependent thyroid hormone activating enzyme type 2 (D2) which converts the inactive T3 into the active T4, resulting in the stimulation of the thyroid hormone receptor and promoting energy expenditure. Mice lacking the D2 gene were resistant to cholic acid-induced weight loss. In both rodents and humans, the most thermogenically important tissues (the brown adipose and skeletal muscle) are specifically targeted by this mechanism because they co-express D2 and GPBAR1. The BA-GPBAR1-cAMP-D2 signalling pathway is therefore a crucial mechanism for fine-tuning energy homeostasis that can be targeted to improve metabolic control.

SUMMARY OF THE INVENTION

In an embodiment of the present invention, provided is a compound of formula I:

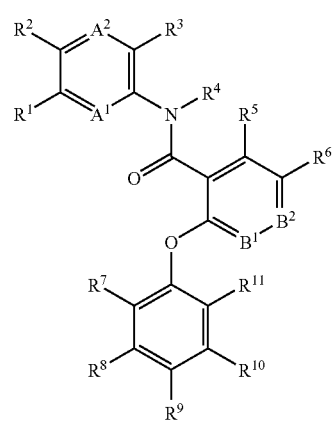

wherein:
$A^1$ is $CR^{12}$ or N;
$A^2$ is $CR^{13}$ or N;
$R^1$ and $R^2$ are independently from each other selected from the group consisting of hydrogen, $C_{1-7}$-alkyl, halogen, cyano and $C_{1-7}$-alkoxy;
$R^{12}$ and $R^{13}$ are independently from each other selected from the group consisting of hydrogen, $C_{1-7}$-alkyl, halogen, cyano, $C_{1-7}$-alkoxy, amino and $C_{1-7}$-alkylsulfanyl;
$R^3$ is selected from the group consisting of hydrogen, $C_{1-7}$-alkyl, halogen, $C_{1-7}$-alkoxy, cyano, $C_{3-7}$-cycloalkyl, N-heterocyclyl, five-membered heteroaryl and phenyl;
$R^4$ is selected from the group consisting of methyl, ethyl, isopropyl, difluoromethyl, trifluoromethyl, cyclopropyl and oxetanyl; or
$R^3$ and $R^4$ together are —X—$(CR^{14}R^{15})_n$— and form part of a ring; wherein
X is selected from the group consisting of —$CR^{16}R^{17}$—, O, S, C=O and $NR^{18}$;
$R^{14}$ and $R^{15}$ are independently from each other selected from hydrogen or $C_{1-7}$-alkyl;

$R^{16}$ and $R^{17}$ are independently from each other selected from the group consisting of hydrogen, $C_{1-7}$ alkyl, $C_{1-7}$-alkoxycarbonyl, unsubstituted heterocyclyl and heterocyclyl substituted by one or two groups selected from $C_{1-7}$-alkyl or halogen, or $R^{16}$ and $R^{17}$ together with the C atom they are attached to form a cyclopropyl or oxetanyl ring or together form a =CH$_2$ or =CF$_2$ group;

$R^{18}$ is selected from the group consisting of hydrogen, $C_{1-7}$-alkyl, halogen-$C_{1-7}$-alkyl, $C_{3-7}$-cycloalkyl, $C_{3-7}$-cycloalkyl-$C_{1-7}$-alkyl, heterocyclyl, heterocyclyl-$C_{1-7}$-alkyl, heteroaryl, heteroaryl-$C_{1-7}$-alkyl, carboxyl-$C_{1-7}$-alkyl, $C_{1-7}$-alkoxycarbonyl-$C_{1-7}$-alkyl, $C_{1-7}$-alkylcarbonyloxy-$C_{1-7}$-alkyl, phenyl, wherein phenyl is unsubstituted or substituted by carboxyl-$C_{1-7}$-alkyl or $C_{1-7}$-alkoxycarbonyl, phenylcarbonyl, wherein phenyl is unsubstituted or substituted by carboxyl-$C_{1-7}$-alkyl or $C_{1-7}$-alkoxycarbonyl, and phenylsulfonyl, wherein phenyl is unsubstituted or substituted by carboxyl-$C_{1-7}$-alkyl or $C_{1-7}$-alkoxycarbonyl, or $R^{18}$ and a $R^{14}$ together are —(CH$_2$)$_3$— and form part of a ring, or $R^{18}$ together with a pair of $R^{14}$ and $R^{15}$ are —CH=CH—CH= and form part of a ring;

and n is 1, 2 or 3;

$B^1$ is N or $CR^{19}$ and $B^2$ is N or $CR^{20}$, provided that at most one of $B^1$ and $B^2$ is N; and $R^{19}$ and $R^{20}$ are independently from each other selected from the group consisting of hydrogen, $C_{1-7}$-alkyl, halogen, halogen-$C_{1-7}$-alkyl, $C_{1-7}$-alkoxy, halogen-$C_{1-7}$-alkoxy and cyano;

$R^5$ and $R^6$ independently from each other are selected from the group consisting of hydrogen, halogen, $C_{1-7}$-alkyl, $C_{1-7}$-alkoxy, halogen-$C_{1-7}$-alkyl, halogen-$C_{1-7}$-alkoxy, and cyano;

and at least one or, in case $R^4$ is methyl or ethyl, at least two of $R^7$, $R^8$, $R^9$, $R^{10}$ and $R^{11}$ are selected from the group consisting of $C_{1-7}$-alkyl, halogen, halogen-$C_{1-7}$-alkyl, $C_{1-7}$-alkoxy, halogen-$C_{1-7}$-alkoxy, cyano, carboxyl, $C_{1-7}$-alkoxycarbonyl, hydroxy-$C_{1-7}$-alkyl, hydroxy-$C_{3-7}$-alkenyl, hydroxy-$C_{3-7}$-alkinyl, carboxyl-$C_{1-7}$-alkyl, carboxyl-$C_{2-7}$-alkenyl, carboxyl-$C_{2-7}$-alkinyl, $C_{1-7}$-alkoxycarbonyl-$C_{1-7}$-alkyl, $C_{1-7}$-alkoxycarbonyl-$C_{2-7}$-alkenyl, $C_{1-7}$-alkoxycarbonyl-$C_{2-7}$-alkinyl, carboxyl-$C_{1-7}$-alkyl-aminocarbonyl, $C_{1-7}$-alkoxycarbonyl-$C_{1-7}$-alkyl-aminocarbonyl, carboxyl-$C_{1-7}$-alkyl-aminocarbonyl-$C_{1-7}$-alkyl, $C_{1-7}$-alkoxycarbonyl-$C_{1-7}$-alkyl-aminocarbonyl-$C_{1-7}$-alkyl, carboxyl-$C_{1-7}$-alkyl-($C_{1-7}$-alkylamino)-carbonyl-$C_{1-7}$-alkyl, $C_{1-7}$-alkoxycarbonyl-$C_{1-7}$-alkyl-($C_{1-7}$-alkylamino)-carbonyl-$C_{1-7}$-alkyl, phenyl, wherein phenyl is unsubstituted or substituted by one to three groups selected from halogen, $C_{1-7}$-alkoxy, carboxyl or $C_{1-7}$-alkoxycarbonyl, phenylcarbonyl, wherein phenyl is unsubstituted or substituted by one to three groups selected from halogen, $C_{1-7}$-alkoxy, carboxyl or $C_{1-7}$-alkoxycarbonyl, phenyl-$C_{1-7}$-alkyl, wherein phenyl is unsubstituted or substituted by one to three groups selected from halogen, $C_{1-7}$-alkoxy, carboxyl or $C_{1-7}$-alkoxycarbonyl, phenyl-$C_{2-7}$-alkinyl, wherein phenyl is unsubstituted or substituted by one to three groups selected from halogen, $C_{1-7}$-alkoxy, carboxyl or $C_{1-7}$-alkoxycarbonyl, and pyrrolidinyl-carbonyl-$C_{1-7}$-alkyl, wherein pyrrolidinyl is substituted by carboxyl, and the other ones of $R^7$, $R^8$, $R^9$, $R^{10}$ and $R^{11}$ are hydrogen;

or pharmaceutically acceptable salts thereof.

In another embodiment of the present invention, provided is a pharmaceutical composition, comprising a therapeutically effective amount of a compound according to formula I and a pharmaceutically acceptable carrier and/or adjuvant.

DETAILED DESCRIPTION

The invention provides for selective, directly acting GPBAR1 agonists. Such agonists are useful as therapeutically active substances, particularly in the treatment and/or prevention of diseases which are associated with the activation of GPBAR1.

The novel compounds of the present invention exceed the compounds known in the art, inasmuch as they are small molecules and they bind to and selectively activate GPBAR1 very efficiently. They are expected to have an enhanced therapeutic potential compared to the compounds already known in the art and can be used for the treatment of diabetes, obesity, metabolic syndrome, hypercholesterolemia, dyslipidemia and a wide range of acute and chronic inflammatory diseases.

Unless otherwise indicated, the following definitions are set forth to illustrate and define the meaning and scope of the various terms used to describe the invention.

The term "halogen" refers to fluoro, chloro, bromo and iodo, with fluoro, chloro and bromo being preferred, and with fluoro and chloro being more preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "$C_{1-10}$-alkyl" refers to a branched or straight-chain monovalent saturated aliphatic hydrocarbon radical of one to ten carbon atoms, such as e.g., methyl, ethyl, n-propyl, isopropyl, n-butyl, sec-butyl, tert-butyl, pentyl, 1,1,3,3-tetramethyl-butyl and the like. Lower alkyl groups as described below are also preferred alkyl groups.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "lower alkenyl" or "$C_{2-7}$-alkenyl" signifies a straight-chain or branched chain hydrocarbon residue comprising an olefinic bond and 2 to 7, preferably 3 to 6, particularly preferred 3 to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl (allyl).

The term "lower alkinyl" or "$C_{2-7}$-alkinyl" signifies a straight-chain or branched chain hydrocarbon residue comprising a triple bond and 3 to 7, preferably 3 to 6, particularly preferred 3 to 4 carbon atoms. Preferred alkinyl groups are ethinyl and 1-propinyl (—C≡C—CH$_3$).

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred is cyclopropyl.

The term "lower cycloalkylalkyl" or "$C_{3-7}$-cycloalkyl-$C_{1-7}$- alkyl" means lower alkyl groups as defined herein before wherein one of the hydrogen atoms of the lower alkyl group is replaced by cycloalkyl. Preferred lower cycloalkylalkyl groups are —$CH_2$-cyclopropyl or —$CH_2$-cyclobutyl.

The term "lower alkoxy" or "$C_{1-7}$-alkoxy" refers to the group —O—R, wherein R is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy.

The term "lower alkylsulfanyl" or "$C_{1-7}$-alkylsulfanyl" defines the group —S—R, wherein R is lower alkyl and the term "lower alkyl" has the previously given meaning. Examples of lower alkylsulfonyl groups are methylsulfanyl (—$SCH_3$) or ethylsulfanyl (—$SC_2H_5$).

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or difluoromethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkoxy groups are trifluoromethoxy, difluoromethoxy, fluormethoxy and chloromethoxy, with trifluoromethoxy being especially preferred.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the preferred lower hydroxyalkyl groups are hydroxymethyl or hydroxyethyl.

The term "lower hydroxyalkenyl" or "hydroxy-$C_{3-7}$-alkenyl" refers to lower alkenyl groups as defined above but having at least 3 carbon atoms wherein at least one of the hydrogen atoms of the lower alkenyl group is replaced by a hydroxy group. Among the preferred lower hydroxyalkenyl groups is hydroxyallyl.

The term "lower hydroxyalkinyl" or "hydroxy-$C_{3-7}$-alkinyl" refers to lower alkinyl groups as defined above but having at least 3 carbon atoms wherein at least one of the hydrogen atoms of the lower alkinyl group is replaced by a hydroxy group. Among the preferred lower hydroxyalkinyl groups is —C≡C—$CH_2$OH.

"Amino" refers to the group —$NH_2$. The term "$C_{1-7}$-alkylamino" means a group —NHR, wherein R is lower alkyl and the term "lower alkyl" has the previously given significance.

The term "carboxyl" means the group —COOH.

The term "lower carboxylalkyl" or "carboxyl-$C_{1-7}$-alkyl" means lower alkyl groups as defined herein before wherein one of the hydrogen atoms of the lower alkyl group is replaced by carboxyl. Preferred lower carboxylalkyl groups are —$CH_2$—COOH or —$CH_2$—$CH_2$—COOH.

The term "lower carboxylalkenyl" or "carboxyl-$C_{2-7}$-alkenyl" means lower alkenyl groups as defined herein before wherein one of the hydrogen atoms of the lower alkenyl group is replaced by carboxyl. Preferred lower carboxylalkenyl group is —CH═CH—$CH_2$—COOH.

The term "lower carboxylalkinyl" or "carboxyl-$C_{2-7}$-alkinyl" means a lower alkinyl group as defined herein before wherein one of the hydrogen atoms of the lower alkinyl group is replaced by carboxyl. Preferred lower carboxylalkinyl group is —C≡C—$CH_2$—COOH.

The term "aminocarbonyl" means the group —CO—$NH_2$.

The term "lower carboxylalkylaminocarbonyl" or "carboxyl-$C_{1-7}$-alkylaminocarbonyl" refers to aminocarbonyl as defined above wherein one of the hydrogen atoms of the amino group is replaced by carboxyl-$C_{1-7}$-alkyl. Preferred lower carboxylalkylaminocarbonyl group is —CO—NH—$CH_2$—COOH.

The term "lower carboxylalkylaminocarbonylalkyl" or "carboxyl-$C_{1-7}$-alkylamino-carbonyl-$C_{1-7}$-alkyl" refers to a lower alkyl group wherein one of the hydrogen atoms of the lower alkyl group is replaced by "carboxyl-$C_{1-7}$-alkylaminocarbonyl" as defined above. Preferred lower carboxylalkylaminocarbonylalkyl group is —$CH_2$—CO—NH—$CH_2$—COOH.

The term "carboxyl-$C_{1-7}$-alkyl-($C_{1-7}$-alkylamino)-carbonyl-$C_{1-7}$-alkyl" refers to a lower alkyl group wherein one of the hydrogen atoms of the lower alkyl group is replaced by "carboxyl-$C_{1-7}$-alkyl-($C_{1-7}$-alkylamino)-carbonyl", for example a group of the formula —$CH_2$—CO—NR—$CH_2$—COOH, wherein R is lower alkyl.

"Lower alkoxycarbonyl" or "$C_{1-7}$-alkoxycarbonyl" refers to the group —CO—OR wherein R is lower alkyl and the term "lower alkyl" has the previously given significance. Preferred lower alkoxycarbonyl groups are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. Preferred lower alkoxycarbonylalkyl group are —$CH_2$—$COOCH_3$ and —$CH_2$—$CH_2$—$COOCH_3$.

The term "lower alkoxycarbonylalkenyl" or "$C_{1-7}$-alkoxycarbonyl-$C_{2-7}$-alkenyl" means a lower alkenyl group as defined above wherein one of the hydrogen atoms of the lower alkenyl group is replaced by $C_{1-7}$-alkoxycarbonyl. Preferred lower alkoxycarbonylalkenyl group is —CH═CH—$CH_2$—$COOCH_3$.

The term "lower alkoxycarbonylalkinyl" or "$C_{1-7}$-alkoxycarbonyl-$C_{2-7}$-alkinyl" means a lower alkinyl group as defined above wherein one of the hydrogen atoms of the lower alkinyl group is replaced by $C_{1-7}$-alkoxycarbonyl. Preferred lower alkoxycarbonylalkinyl group is —C≡C—$CH_2$—$COOCH_3$.

The term "lower alkoxycarbonylalkylaminocarbonyl" or "$C_{1-7}$-alkoxycarbonyl-$C_{1-7}$-alkylaminocarbonyl" refers to aminocarbonyl as defined above wherein one of the hydrogen atoms of the amino group is replaced by $C_{1-7}$-alkoxycarbonyl-$C_{1-7}$-alkyl. Preferred lower carboxylalkylaminocarbonyl group is —CO—NH—$CH_2$—$COOCH_3$.

The term "lower alkoxycarbonylalkylaminocarbonylalkyl" or "$C_{1-7}$-alkoxycarbonyl-$C_{1-7}$-alkylamino-carbonyl-$C_{1-7}$-alkyl" refers to a lower alkyl group wherein one of the hydrogen atoms of the lower alkyl group is replaced by "$C_{1-7}$-alkoxycarbonyl-$C_{1-7}$-alkylaminocarbonyl" as defined above Preferred lower alkoxycarbonylalkylaminocarbonylalkyl group is —$CH_2$—CO—NH—$CH_2$—$COOCH_3$.

The term "$C_{1-7}$-alkoxycarbonyl-$C_{1-7}$-alkyl-($C_{1-7}$-alkylamino)-carbonyl-$C_{1-7}$-allyl" refers to a lower alkyl group wherein one of the hydrogen atoms of the lower alkyl group is replaced by "$C_{1-7}$-alkoxycarbonyl-$C_{1-7}$-alkyl-($C_{1-7}$-alkylamino)-carbonyl". Preferred group is —$CH_2$—CO—$NCH_3$—$CH_2$—$COOCH_3$.

The term "$C_{1-7}$-alkylcarbonyl" means the group —CO—R, wherein R is lower alkyl as defined above.

The term "$C_{1-7}$-alkylcarbonyloxy" refers to the group —O—CO—R, wherein R is lower alkyl as defined herein before.

The term "lower alkylcarbonyloxyalkyl" or "$C_{1-7}$-alkylcarbonyloxy-$C_{1-7}$-alkyl" refers to lower alkyl groups as defined above wherein one of the hydrogen atoms of the lower alkyl group is replaced by $C_{1-7}$-alkylcarbonyloxy. A preferred lower alkylcarbonyloxyalkyl group is —CH$_2$—CH$_2$—O—CO—CH$_3$.

The term "phenylcarbonyl" refers to the group —CO—R' wherein R' is phenyl.

The term "phenylsulfonyl" means the group —SO$_2$—R' wherein R' is phenyl.

The term "lower phenylalkyl" or "phenyl-$C_{1-7}$-alkyl" refers to lower alkyl groups as defined above wherein at least one of the hydrogen atoms of the lower alkyl group is replaced by a phenyl group. The phenyl group may be further substituted. Preferred lower phenylalkyl groups are benzyl or phenethyl.

The term "lower phenylalkinyl" or "phenyl-$C_{2-7}$-alkinyl" refers to a lower alkinyl group as defined above wherein one of the hydrogen atoms of the lower alkinyl group is replaced by a phenyl group. The phenyl group may be further substituted. Preferred lower phenylalkinyl group is phenylethinyl.

The term "pyrrolidinyl-carbonyl" means a group

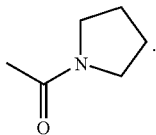

The term "heterocyclyl" in general refers to a saturated or partly unsaturated 3-, 4-, 5-, 6- or 7-membered ring which can comprise one, two or three atoms selected from nitrogen, oxygen and/or sulphur. Examples of heterocyclyl rings include azirinyl, azetidinyl, oxetanyl, piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiamorpholinyl. A preferred heterocyclyl group is oxetanyl.

The term "lower heterocyclylalkyl" or "heterocyclyl-$C_{1-7}$-alkyl" refers to lower alkyl groups as defined above wherein at least one of the hydrogen atoms of the lower alkyl group is replaced by a heterocyclyl group as defined above.

"N-heterocyclyl" means a 3-, 4-, 5-, 6- or 7-membered saturated heterocyclic ring containing a nitrogen atom ("N") and optionally containing a further heteroatom selected from nitrogen, oxygen or sulfur. Preferably, the N-heterocyclyl ring is connected by the nitrogen atom to the carbon atom the ring is attached to. Preferred N-heterocyclyl rings are selected from the group consisting of azirinyl, azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl and azepanyl.

The term "heteroaryl" in general refers to an aromatic 5- or 6-membered ring which comprises one, two or three atoms selected from nitrogen, oxygen and/or sulphur, such as pyridyl, pyrazinyl, pyrimidinyl, pyridazinyl, 2-oxo-1,2-dihydropyridinyl, oxazolyl, oxadiazolyl, isoxazolyl, thiadiazolyl, tetrazolyl, pyrazolyl, imidazolyl, furyl, thiazolyl and thienyl.

The term "heteroaryl" further refers to bicyclic aromatic groups comprising two 5- or 6-membered rings, in which one or both rings can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl and indazolyl. Preferred heteroaryl group is furyl.

The term "lower heteroarylalkyl" or "heteroaryl-$C_{1-7}$-alkyl" refers to lower alkyl groups as defined above wherein at least one of the hydrogen atoms of the lower alkyl group is replaced by a heteroaryl group as defined above.

The term "a five-membered N-heteroaryl" refers to an aromatic 5-membered ring which comprises at least one nitrogen atom and can in addition comprise one to three atoms selected from nitrogen, oxygen and/or sulphur. Preferred five-membered heteroaryl rings are selected from the group consisting of pyrrolyl, pyrazolyl, imidazolyl, triazolyl, tetrazolyl, oxazolyl, oxadiazolyl, isoxazolyl, thiadiazolyl, and thiazolyl. Preferably, the five-membered heteroaryl ring is connected by a nitrogen atom to the carbon atom the ring is attached to. Most preferably, the five-membered heteroaryl group is pyrrolyl.

Compounds of formula I can form pharmaceutically acceptable salts. The term "pharmaceutically acceptable salts" refers to those salts which retain the biological effectiveness and properties of the free bases or free acids, which are not biologically or otherwise undesirable. The salts are for example acid addition salts of compounds of formula I with physiologically compatible mineral acids, such as hydrochloric acid, sulfuric acid, sulfurous acid or phosphoric acid; or with organic acids, such as methanesulfonic acid, ethanesulfonic acid, p-toluenesulfonic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable minor images are termed "enantiomers", or sometimes optical isomers. A carbon atom bonded to four nonidentical substituents is termed a "chiral center".

In detail, the present invention relates to compounds of the formula

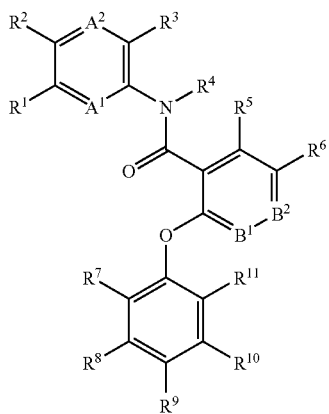

I wherein
$A^1$ is $CR^{12}$ or N;
$A^2$ is $CR^{13}$ or N;
$R^1$ and $R^2$ are independently from each other selected from the group consisting of hydrogen, $C_{1-7}$-alkyl, halogen, cyano and $C_{1-7}$-alkoxy;
$R^{12}$ and $R^{13}$ are independently from each other selected from the group consisting of hydrogen, $C_{1-7}$-alkyl, halogen, cyano, $C_{1-7}$-alkoxy, amino and $C_{1-7}$-alkylsulfanyl;
$R^3$ is selected from the group consisting of hydrogen, $C_{1-7}$-alkyl, halogen, $C_{1-7}$-alkoxy, cyano, $C_{3-7}$-cycloalkyl, N-heterocyclyl, five-membered heteroaryl and phenyl;
$R^4$ is selected from the group consisting of methyl, ethyl, isopropyl, difluoromethyl, trifluoromethyl, cyclopropyl and oxetanyl; or
$R^3$ and $R^4$ together are $-X-(CR^{14}R^{15})_n-$ and form part of a ring; wherein
X is selected from the group consisting of $-CR^{16}R^{17}-$, O, S, C=O and $NR^{18}$;
$R^{14}$ and $R^{15}$ are independently from each other selected from hydrogen or $C_{1-7}$-alkyl;
$R^{16}$ and $R^{17}$ are independently from each other selected from the group consisting of hydrogen, $C_{1-7}$-alkyl, $C_{1-7}$-alkoxycarbonyl, unsubstituted heterocyclyl and heterocyclyl substituted by one or two groups selected from $C_{1-7}$-alkyl or halogen,
or $R^{16}$ and $R^{17}$ together with the C atom they are attached to form a cyclopropyl or oxetanyl ring or together form a =$CH_2$ or =$CF_2$ group;
$R^{18}$ is selected from the group consisting of hydrogen, $C_{1-7}$-alkyl,
halogen-$C_{1-7}$-alkyl, $C_{3-7}$-cycloalkyl, $C_{3-7}$-cycloalkyl-$C_{1-7}$-alkyl,
heterocyclyl, heterocyclyl-$C_{1-7}$-alkyl,
heteroaryl, heteroaryl-$C_{1-7}$-alkyl,
carboxyl-$C_{1-7}$-alkyl, $C_{1-7}$-alkoxycarbonyl-$C_{1-7}$-alkyl,
$C_{1-7}$-alkylcarbonyloxy-$C_{1-7}$-alkyl,
phenyl, wherein phenyl is unsubstituted or substituted by carboxyl-$C_{1-7}$-alkyl or $C_{1-7}$-alkoxycarbonyl,
phenylcarbonyl, wherein phenyl is unsubstituted or substituted by carboxyl-$C_{1-7}$-alkyl or $C_{1-7}$-alkoxycarbonyl, and
phenylsulfonyl, wherein phenyl is unsubstituted or substituted by carboxyl-$C_{1-7}$-alkyl or $C_{1-7}$-alkoxycarbonyl,
or $R^{18}$ and a $R^{14}$ together are $-(CH_2)_3-$ and form part of a ring, or $R^{18}$ together with a pair
of $R^{14}$ and $R^{15}$ are $-CH=CH-CH=$ and form part of a ring;
and n is 1, 2 or 3;
$B^1$ is N or $CR^{19}$ and $B^2$ is N or $CR^{20}$, provided that at most one of $B^1$ and $B^2$ is N; and
$R^{19}$ and $R^{20}$ are independently from each other selected from the group consisting of hydrogen, $C_{1-7}$-alkyl, halogen, halogen-$C_{1-7}$-alkyl, $C_{1-7}$-alkoxy, halogen-$C_{1-7}$-alkoxy and cyano;
$R^5$ and $R^6$ independently from each other are selected from the group consisting of hydrogen, halogen, $C_{1-7}$-alkyl, $C_{1-7}$-alkoxy, halogen-$C_{1-7}$-alkyl, halogen-$C_{1-7}$-alkoxy, and cyano;
and at least one or, in case $R^4$ is methyl or ethyl, at least two of $R^7$, $R^8$, $R^9$, $R^{10}$ and are selected from the group consisting of
$C_{1-7}$-alkyl, halogen, halogen-$C_{1-7}$-alkyl, $C_{1-7}$-alkoxy, halogen-$C_{1-7}$-alkoxy,
cyano, carboxyl, $C_{1-7}$-alkoxycarbonyl,
hydroxy-$C_{1-7}$-alkyl, hydroxy-$C_{3-7}$-alkenyl, hydroxy-$C_{3-7}$-alkinyl,
carboxyl-$C_{1-7}$-alkyl, carboxyl-$C_{2-7}$-alkenyl, carboxyl-$C_{2-7}$-alkinyl,
$C_{1-7}$-alkoxycarbonyl-$C_{1-7}$-alkyl, $C_{1-7}$-alkoxycarbonyl-$C_{2-7}$-alkenyl,
$C_{1-7}$-alkoxycarbonyl-$C_{2-7}$-alkinyl,
carboxyl-$C_{1-7}$-alkyl-aminocarbonyl, $C_{1-7}$-alkoxycarbonyl-$C_{1-7}$-alkyl-aminocarbonyl,
carboxyl-$C_{1-7}$-alkyl-aminocarbonyl-$C_{1-7}$-alkyl,
$C_{1-7}$-alkoxycarbonyl-$C_{1-7}$-alkyl-aminocarbonyl-$C_{1-7}$-alkyl,
carboxyl-$C_{1-7}$-alkyl-($C_{1-7}$-alkyl amino)-carbonyl-$C_{1-7}$-alkyl,
$C_{1-7}$-alkoxycarbonyl-$C_{1-7}$-alkyl-($C_{1-7}$-alkylamino)-carbonyl-$C_{1-7}$-alkyl,
phenyl, wherein phenyl is unsubstituted or substituted by one to three groups selected from halogen, $C_{1-7}$-alkoxy, carboxyl or $C_{1-7}$-alkoxycarbonyl,
phenylcarbonyl, wherein phenyl is unsubstituted or substituted by one to three groups selected from halogen, $C_{1-7}$-alkoxy, carboxyl or $C_{1-7}$-alkoxycarbonyl,
phenyl-$C_{1-7}$-alkyl, wherein phenyl is unsubstituted or substituted by one to three groups selected from halogen, $C_{1-7}$-alkoxy, carboxyl or $C_{1-7}$-alkoxycarbonyl,
phenyl-$C_{2-7}$-alkinyl, wherein phenyl is unsubstituted or substituted by one to three groups selected from halogen, $C_{1-7}$-alkoxy, carboxyl or $C_{1-7}$-alkoxycarbonyl, and
pyrrolidinyl-carbonyl-$C_{1-7}$-alkyl, wherein pyrrolidinyl is substituted by carboxyl,
and the other ones of $R^7$, $R^8$, $R^9$, $R^{10}$ and $R^{11}$ are hydrogen;
or pharmaceutically acceptable salts thereof.

Preferred compounds of formula I according to the present invention are those, wherein $A^1$ is $CR^{12}$ and $A^2$ is $CR^{13}$ or wherein $A^1$ is $CR^{12}$ and $A^2$ is N or wherein $A^1$ is N and $A^2$ is $CR^{13}$, with $R^{12}$ and $R^{13}$ being independently from each other selected from the group consisting of hydrogen, $C_{1-7}$-alkyl, halogen, cyano, $C_{1-7}$-alkoxy, amino and $C_{1-7}$-alkylsulfanyl.

Especially preferred are those compounds of formula I according to the present invention, wherein $A^1$ is $CR^{12}$ and $A^2$ is $CR^{13}$, wherein $R^{12}$ and $R^{13}$ are independently from each other selected from the group consisting of hydrogen, $C_{1-7}$-alkyl, halogen, cyano, $C_{1-7}$-alkoxy, amino and $C_{1-7}$-alkylsulfanyl. These are compounds of the formula

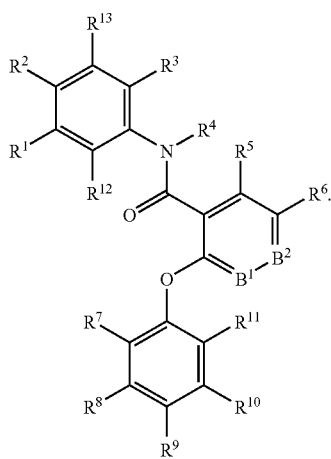

I-A

Furthermore, compounds of formula I are preferred, wherein $A^1$ is N and $A^2$ is $CR^{12}$ or wherein $A^1$ is $CR^{13}$ and $A^2$ is N, with $R^{12}$ and $R^{13}$ being independently from each other selected from the group consisting of hydrogen, $C_{1-7}$-alkyl, halogen, cyano, $C_{1-7}$-alkoxy, amino and $C_{1-7}$-alkylsulfanyl.

Especially preferred are those compounds of formula I, wherein $A^1$ is $CR^{13}$ and $A^2$ is N, with $R^{12}$ and $R^{13}$ being independently from each other selected from the group consisting of hydrogen, $C_{1-7}$-alkyl, halogen, cyano, $C_{1-7}$-alkoxy, amino and $C_{1-7}$-alkylsulfanyl.

In addition, compounds of formula I are preferred, wherein $R^1$ and $R^2$ are independently from each other selected from the group consisting of hydrogen, $C_{1-7}$-alkyl, halogen, cyano and $C_{1-7}$-alkoxy, more preferably from the group consisting of hydrogen, $C_{1-7}$-alkyl and halogen.

Compounds of formula I are further preferred, wherein $R^3$ and $R^4$ together are —X—$(CR^{14}R^{15})_n$— and form part of a ring; wherein X is selected from the group consisting of —$CR^{16}R^{17}$—, O, S, C=O and $NR^{18}$;

$R^{14}$ and $R^{15}$ are independently from each other selected from hydrogen or $C_{1-7}$-alkyl;

$R^{16}$ and $R^{17}$ are independently from each other selected from the group consisting of hydrogen,
$C_{1-7}$-alkyl, $C_{1-7}$-alkoxycarbonyl, unsubstituted heterocyclyl and heterocyclyl substituted by one or two groups selected from $C_{1-7}$-alkyl or halogen,
or $R^{16}$ and $R^{17}$ together with the C atom they are attached to form a cyclopropyl or oxetanyl ring or together form a =$CH_2$ or =$CF_2$ group;

$R^{18}$ is selected from the group consisting of hydrogen, $C_{1-7}$-alkyl,
halogen $C_{1-7}$ alkyl, $C_{3-7}$-cycloalkyl, $C_{3-7}$-cycloalkyl-$C_{1-7}$-alkyl,
heterocyclyl, heterocyclyl-$C_{1-7}$-alkyl,
heteroaryl, heteroaryl-$C_{1-7}$-alkyl,
carboxyl-$C_{1-7}$-alkyl, $C_{1-7}$-alkoxycarbonyl-$C_{1-7}$-alkyl,
$C_{1-7}$-alkylcarbonyloxy-$C_{1-7}$-alkyl,
phenyl, wherein phenyl is unsubstituted or substituted by carboxyl-$C_{1-7}$-alkyl or $C_{1-7}$-alkoxycarbonyl,
phenylcarbonyl, wherein phenyl is unsubstituted or substituted by carboxyl-$C_{1-7}$-alkyl or $C_{1-7}$-alkoxycarbonyl, and
phenylsulfonyl, wherein phenyl is unsubstituted or substituted by carboxyl-$C_{1-7}$-alkyl or $C_{1-7}$-alkoxycarbonyl,
or $R^{18}$ and a $R^{14}$ together are —$(CH_2)_3$— and form part of a ring, or $R^{18}$ together with a pair of $R^{14}$ and $R^{15}$ are —CH=CH—CH= and form part of a ring;
and n is 1, 2 or 3.

Within this group, compounds of formula I are especially preferred, wherein X is selected from the group consisting of —$CR^{16}R^{17}$—, O, S, C=O and $NR^{18}$; $R^{14}$ and $R^{15}$ are independently from each other selected from hydrogen or $C_{1-7}$-alkyl; $R^{16}$ and $R^{17}$ are independently from each other selected from hydrogen or $C_{1-7}$-alkyl or together with the C atom they are attached to form a cyclopropyl or oxetanyl ring or together form a =$CH_2$ or =$CF_2$ group; $R^{18}$ is selected from the group consisting of methyl, ethyl, propyl, isopropyl, phenyl and pyridyl, and n is 1, 2 or 3.

Furthermore, compounds of formula I are especially preferred, wherein X is —$CH_2$—, $R^{14}$ and $R^{15}$ are independently from each other selected from hydrogen or methyl, and n is 2. Even more preferred are those, wherein $R^{14}$ and $R^{15}$ are hydrogen. These are compounds of the formula

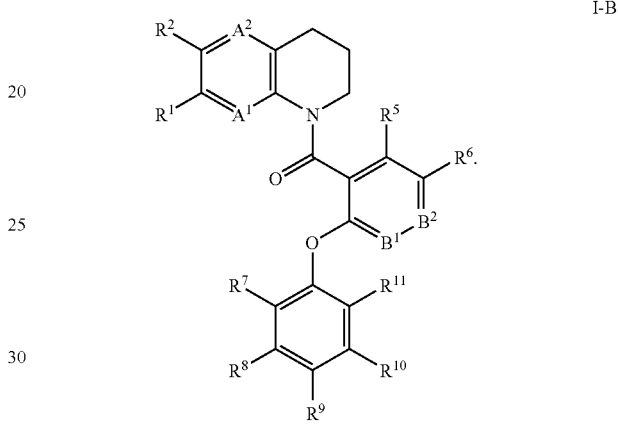

I-B

Also especially preferred are compounds of formula I, wherein X is O, $R^{14}$ and $R^{15}$ are hydrogen and n is 2. These are compounds of the formula

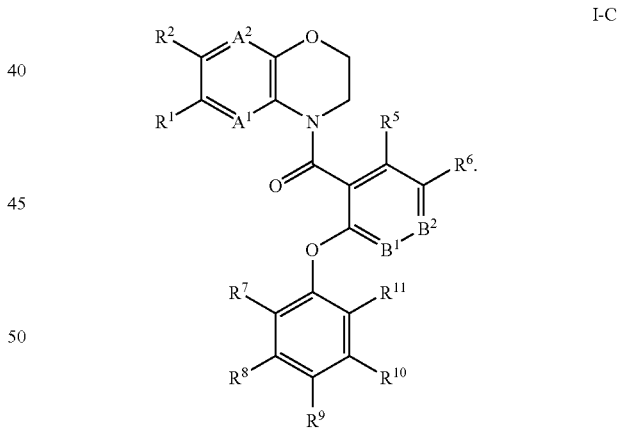

I-C

In addition, compounds of formula I are especially preferred, wherein $R^{14}$ and $R^{15}$ are hydrogen, n is 2 and X is $NR^{18}$ with $R^{18}$ being selected from the group consisting of hydrogen, $C_{1-7}$-alkyl, halogen-$C_{1-7}$-alkyl, $C_{3-7}$-cycloalkyl, $C_{3-7}$-cycloalkyl-$C_{1-7}$-alkyl, heterocyclyl, heterocyclyl-$C_{1-7}$-alkyl, heteroaryl, heteroaryl-$C_{1-7}$-alkyl, carboxyl-$C_{1-7}$-alkyl, $C_{1-7}$-alkoxycarbonyl-$C_{1-7}$-alkyl, $C_{1-7}$-alkylcarbonyloxy-$C_{1-7}$-alkyl, phenyl, wherein phenyl is unsubstituted or substituted by carboxyl-$C_{1-7}$-alkyl or $C_{1-7}$-alkoxycarbonyl, phenylcarbonyl, wherein phenyl is unsubstituted or substituted by carboxyl-$C_{1-7}$-alkyl or $C_{1-7}$-alkoxycarbonyl, and phenylsulfonyl, wherein phenyl is unsubstituted or substituted by carboxyl-$C_{1-7}$-alkyl or $C_{1-7}$-alkoxycarbonyl. These are compounds having the formula

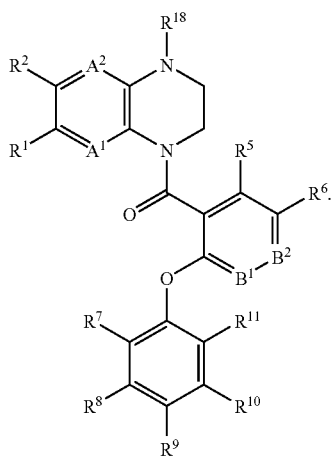

I-D

Also included in the invention are compounds of formula I, wherein $R^{18}$ and a $R^{14}$ together are —(CH$_2$)$_3$— and form part of a ring. These compounds have the formula

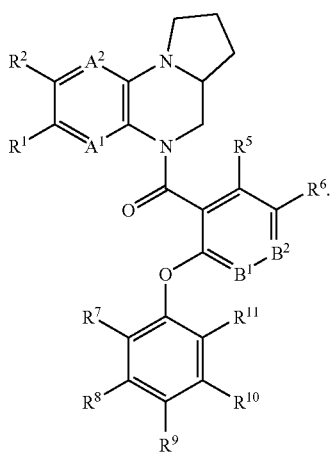

I-D$^x$

In addition, compounds of formula I are included in the present invention, wherein $R^{18}$ together with a pair of $R^{14}$ and $R^{15}$ are —CH=CH—CH= and form part of a ring. These are compounds having the formula

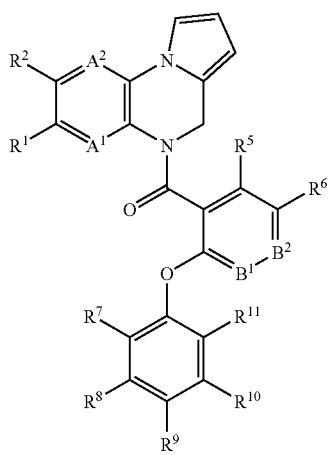

I-D$^{xx}$

Another group of preferred compounds of formula I are those, wherein $R^3$ is selected from the group consisting of hydrogen, C$_{1-7}$-alkyl, halogen, C$_{1-7}$-alkoxy, cyano, C$_{3-7}$-cycloalkyl, N-heterocyclyl, a five-membered heteroaryl ring and phenyl; and $R^4$ is selected from the group consisting of methyl, ethyl, isopropyl, difluoromethyl, trifluoromethyl, cyclopropyl and oxetanyl. Especially preferred are those compounds of formula I, wherein $R^4$ is methyl or ethyl. Preferably, $R^3$ is selected from the group consisting of hydrogen, C$_{1-7}$-alkyl, halogen, C$_{1-7}$-alkoxy, cyano, cyclopropyl, pyrrolyl and phenyl.

Furthermore, compounds of formula I are preferred, wherein B$^1$ is N and B$^2$ is CR$^{20}$, with R$^{20}$ being selected from the group consisting of hydrogen, C$_{1-7}$-alkyl, halogen, halogen-C$_{1-7}$-alkyl, C$_{1-7}$-alkoxy, halogen-C$_{1-7}$-alkoxy and cyano. These are compounds of the formula

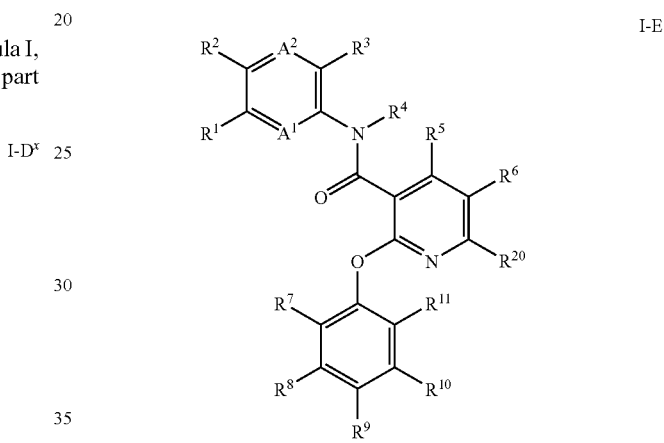

I-E

Also preferred are compounds of formula I of the present invention, wherein B$^1$ is CR$^{19}$ and B$^2$ is N, with R$^{19}$ being selected from the group consisting of hydrogen, C$_{1-7}$-alkyl, halogen, halogen-C$_{1-7}$-alkyl, C$_{1-7}$-alkoxy, halogen-C$_{1-7}$-alkoxy and cyano. These are compounds of the formula

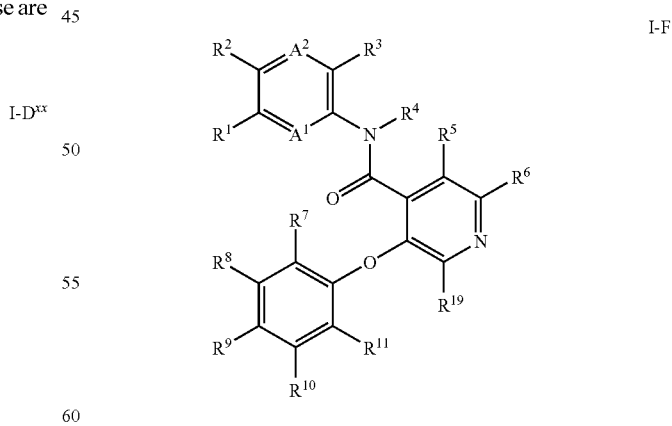

I-F

Preferred are further compounds of formula I, wherein B$^1$ is CR$^{19}$ and B$^2$ is CR$^{20}$, with R$^{19}$ and R$^{20}$ being independently from each other selected from the group consisting of hydrogen, C$_{1-7}$-alkyl, halogen, halogen-C$_{1-7}$-alkyl, C$_{1-7}$-alkoxy, halogen-C$_{1-7}$-alkoxy and cyano. These are compounds of the formula

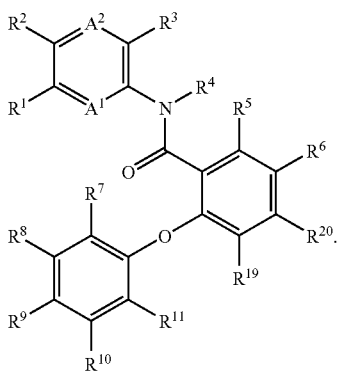

I-G $R^5$ and $R^6$ are independently from each other selected from the group consisting of hydrogen, halogen, $C_{1-7}$-alkyl, $C_{1-7}$-alkoxy and halogen-$C_{1-7}$-alkoxy. Preferred are compounds of formula I, wherein $R^5$ and $R^6$ are independently from each other hydrogen or halogen.

Compounds of the present invention are further those, wherein and at least one or, in case $R^4$ is methyl or ethyl, at least two of $R^7$, $R^8$, $R^9$, $R^{10}$ and $R^{11}$ are selected from the group consisting of $C_{1-7}$-alkyl, halogen, halogen-$C_{1-7}$-alkyl, $C_{1-7}$-alkoxy, halogen-$C_{1-7}$-alkoxy, cyano, carboxyl, $C_{1-7}$-alkoxycarbonyl, hydroxy-$C_{1-7}$-alkyl, hydroxy-$C_{3-7}$-alkenyl, hydroxy-$C_{3-7}$-alkinyl, carboxyl-$C_{1-7}$-alkyl, carboxyl-$C_{2-7}$-alkenyl, carboxyl-$C_{2-7}$-alkinyl, $C_{1-7}$-alkoxycarbonyl-$C_{1-7}$-alkyl, $C_{1-7}$-alkoxycarbonyl-$C_{2-7}$-alkenyl, $C_{1-7}$-alkoxycarbonyl-$C_{2-7}$-alkinyl, carboxyl-$C_{1-7}$-alkyl-aminocarbonyl, $C_{1-7}$-alkoxycarbonyl-$C_{1-7}$-alkyl-aminocarbonyl, carboxyl-$C_{1-7}$-alkyl-aminocarbonyl-$C_{1-7}$-alkyl, $C_{1-7}$-alkoxycarbonyl-$C_{1-7}$-alkyl-aminocarbonyl-$C_{1-7}$-alkyl, carboxyl-$C_{1-7}$-alkyl-($C_{1-7}$-alkylamino)-carbonyl-$C_{1-7}$-alkyl, $C_{1-7}$-alkoxycarbonyl-$C_{1-7}$-alkyl-($C_{1-7}$-alkylamino)-carbonyl-$C_{1-7}$-alkyl, phenyl, wherein phenyl is unsubstituted or substituted by one to three groups selected from halogen, $C_{1-7}$-alkoxy, carboxyl or $C_{1-7}$-alkoxycarbonyl, phenylcarbonyl, wherein phenyl is unsubstituted or substituted by one to three groups selected from halogen, $C_{1-7}$-alkoxy, carboxyl or $C_{1-7}$-alkoxycarbonyl, phenyl-$C_{1-7}$-alkyl, wherein phenyl is unsubstituted or substituted by one to three groups selected from halogen, $C_{1-7}$-alkoxy, carboxyl or $C_{1-7}$-alkoxycarbonyl, phenyl-$C_{2-7}$-alkinyl, wherein phenyl is unsubstituted or substituted by one to three groups selected from halogen, $C_{1-7}$-alkoxy, carboxyl or $C_{1-7}$-alkoxycarbonyl, and pyrrolidinyl-carbonyl-$C_{1-7}$-alkyl, wherein pyrrolidinyl is substituted by carboxyl, and the other ones of $R^7$, $R^8$, $R^9$, $R^{10}$ and $R^{11}$ are hydrogen.

More preferably, at least two of $R^7$, $R^8$, $R^9$, $R^{10}$ and $R^{11}$ are selected from the group consisting of $C_{1-7}$-alkyl, halogen, halogen-$C_{1-7}$-alkyl, $C_{1-7}$-alkoxy, halogen-$C_{1-7}$-alkoxy, cyano, carboxyl, $C_{1-7}$-alkoxycarbonyl, hydroxy-$C_{1-7}$-alkyl, hydroxy-$C_{3-7}$-alkenyl, hydroxy-$C_{3-7}$-alkinyl, carboxyl-$C_{1-7}$-alkyl, carboxyl-$C_{2-7}$-alkenyl, carboxyl-$C_{2-7}$-alkinyl, $C_{1-7}$-alkoxycarbonyl-$C_{1-7}$-alkyl, $C_{1-7}$-alkoxycarbonyl-$C_{2-7}$-alkenyl, $C_{1-7}$-alkoxycarbonyl-$C_{2-7}$-alkinyl, carboxyl-$C_{1-7}$-alkyl-aminocarbonyl, $C_{1-7}$-alkoxycarbonyl-$C_{1-7}$-alkyl-aminocarbonyl, carboxyl-$C_{1-7}$-alkyl-aminocarbonyl-$C_{1-7}$-alkyl, $C_{1-7}$-alkoxycarbonyl-$C_{1-7}$-alkyl-aminocarbonyl-$C_{1-7}$-alkyl, carboxyl-$C_{1-7}$-alkyl-($C_{1-7}$-alkylamino)-carbonyl-$C_{1-7}$-alkyl, $C_{1-7}$-alkoxycarbonyl-$C_{1-7}$-alkyl-($C_{1-7}$-alkylamino)-carbonyl-$C_{1-7}$-alkyl, phenyl, wherein phenyl is unsubstituted or substituted by one to three groups selected from halogen, $C_{1-7}$-alkoxy, carboxyl or $C_{1-7}$-alkoxycarbonyl, phenylcarbonyl, wherein phenyl is unsubstituted or substituted by one to three groups selected from halogen, $C_{1-7}$-alkoxy, carboxyl or $C_{1-7}$-alkoxycarbonyl, phenyl-$C_{1-7}$-alkyl, wherein phenyl is unsubstituted or substituted by one to three groups selected from halogen, $C_{1-7}$-alkoxy, carboxyl or $C_{1-7}$-alkoxycarbonyl, phenyl-$C_{2-7}$-alkinyl, wherein phenyl is unsubstituted or substituted by one to three groups selected from halogen, $C_{1-7}$-alkoxy, carboxyl or $C_{1-7}$-alkoxycarbonyl, and pyrrolidinyl-carbonyl-$C_{1-7}$-alkyl, wherein pyrrolidinyl is substituted by carboxyl, and the other ones of $R^7$, $R^8$, $R^9$, $R^{10}$ and $R^{11}$ are hydrogen.

Especially preferred are compounds of formula I, wherein $R^7$ and $R^{10}$ are halogen. Most preferably, $R^7$ and $R^{10}$ are halogen and $R^8$, $R^9$ and $R^{11}$ are hydrogen.

Furthermore, preferred are compounds of formula

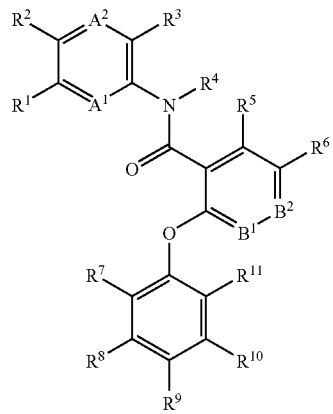

I wherein
$A^1$ is $CR^{12}$ or N;
$A^2$ is $CR^{13}$ or N;
$R^1$ and $R^2$ are independently from each other selected from the group consisting of hydrogen, $C_{1-7}$-alkyl, halogen, cyano and $C_{1-7}$-alkoxy;
$R^{12}$ and $R^{13}$ are independently from each other selected from the group consisting of hydrogen, $C_{1-7}$-alkyl, halogen, cyano and $C_{1-7}$-alkoxy;
$R^3$ is selected from the group consisting of hydrogen, $C_{1-7}$-alkyl, halogen, $C_{1-7}$-alkoxy, cyano, N-heterocyclyl, five-membered heteroaryl and phenyl;
$R^4$ is selected from the group consisting of methyl, ethyl, isopropyl, difluoromethyl, trifluoromethyl, cyclopropyl and oxetanyl; or
$R^3$ and $R^4$ together are —X—$(CR^{14}R^{15})_n$— and form part of a ring; wherein
X is selected from the group consisting of —$CR^{16}R^{17}$—, O, S, C=O and $NR^{18}$;
$R^{14}$ and $R^{15}$ are independently from each other selected from hydrogen or $C_{1-7}$-alkyl,
$R^{16}$ and $R^{17}$ are independently from each other selected from hydrogen or $C_{1-7}$-alkyl or together with the C atom they are attached to form a cyclopropyl or oxetanyl ring or together form a =$CH_2$ or =$CF_2$ group,
$R^{18}$ is selected from the group consisting of methyl, ethyl, propyl, isopropyl, phenyl and pyridyl,
and n is 1, 2 or 3;
$B^1$ is N or $CR^{19}$ and $B^2$ is N or $CR^{20}$, provided that at most one of $B^1$ and $B^2$ is N; and
$R^{19}$ and $R^{20}$ are independently from each other selected from the group consisting of hydrogen, $C_{1-7}$-alkyl, halogen, halogen-$C_{1-7}$-alkyl, $C_{1-7}$-alkoxy, halogen-$C_{1-7}$-alkoxy and cyano;

R$^5$ and R$^6$ independently from each other are selected from the group consisting of hydrogen, halogen, C$_{1-7}$-alkyl, C$_{1-7}$-alkoxy and halogen-C$_{1-7}$-alkoxy, and at least one or, in case R$^4$ is methyl or ethyl, at least two of R$^7$, R$^8$, R$^9$, R$^{10}$ and R$^{11}$ are selected from the group consisting of C$_{1-7}$-alkyl, halogen, halogen-C$_{1-7}$-alkyl, C$_{1-7}$-alkoxy, halogen-C$_{1-7}$-alkoxy, cyano, phenyl and phenylcarbonyl, and the other ones of R$^7$, R$^8$, R$^9$, R$^{10}$ and R$^{11}$ are hydrogen;

or pharmaceutically acceptable salts thereof.

Examples of preferred compounds of formula I are the following:

(3,4-dihydro-2H-quinolin-1-yl)-[2-(3-trifluoromethyl-phenoxy)-pyridin-3-yl]-methanone,
[2-(2-chloro-phenoxy)-pyridin-3-yl]-(3,4-dihydro-2H-quinolin-1-yl)-methanone,
[2-(3-chloro-phenoxy)-pyridin-3-yl]-(3,4-dihydro-2H-quinolin-1-yl)-methanone,
(6-methyl-3,4-dihydro-2H-quinolin-1-yl)-[2-(3-trifluoromethyl-phenoxy)-pyridin-3-yl]-methanone,
[2-(3-chloro-phenoxy)-pyridin-3-yl]-(6-methyl-3,4-dihydro-2H-quinolin-1-yl)-methanone,
[2-(3,4-dichloro-phenoxy)-pyridin-3-yl]-(3,4-dihydro-2H-quinolin-1-yl)-methanone,
3-[3-(3,4-dihydro-2H-quinoline-1-carbonyl)-pyridin-2-yloxy]-benzonitrile,
(3,4-dihydro-2H-quinolin-1-yl)-(2-m-tolyloxy-pyridin-3-yl)-methanone,
[2-(3-chloro-4-methyl-phenoxy)-pyridin-3-yl]-(3,4-dihydro-2H-quinolin-1-yl)-methanone,
[2-(3-chloro-4-fluoro-phenoxy)-pyridin-3-yl]-(3,4-dihydro-2H-quinolin-1-yl)-methanone,
[2-(5-chloro-2-methyl-phenoxy)-pyridin-3-yl]-(3,4-dihydro-2H-quinolin-1-yl)-methanone,
[2-(2,3-dichloro-phenoxy)-pyridin-3-yl]-(3,4-dihydro-2H-quinolin-1-yl)-methanone,
[2-(3-chloro-5-fluoro-phenoxy)-pyridin-3-yl]-(3,4-dihydro-2H-quinolin-1-yl)-methanone,
(3,4-dihydro-2H-quinolin-1-yl)-[2-(2,4,5-trichloro-phenoxy)-pyridin-3-yl]-methanone,
[2-(3-benzoyl-phenoxy)-pyridin-3-yl]-(3,4-dihydro-2H-quinolin-1-yl)-methanone,
(3,4-dihydro-2H-quinolin-1-yl)-[2-(3-trifluoromethoxy-phenoxy)-pyridin-3-yl]-methanone,
[2-(3,5-dichloro-phenoxy)-pyridin-3-yl]-(3,4-dihydro-2H-quinolin-1-yl)-methanone,
(3,4-dihydro-2H-quinolin-1-yl)-[2-(3-fluoro-phenoxy)-pyridin-3-yl]-methanone,
(3,4-dihydro-2H-quinolin-1-yl)-[2-(3-isopropyl-phenoxy)-pyridin-3-yl]-methanone,
(3,4-dihydro-2H-quinolin-1-yl)-[2-(3-ethyl-phenoxy)-pyridin-3-yl]-methanone,
(3,4-dihydro-2H-quinolin-1-yl)-[2-(3-iodo-phenoxy)-pyridin-3-yl]-methanone,
[2-(3-chloro-2-fluoro-5-trifluoromethyl-phenoxy)-pyridin-3-yl]-(3,4-dihydro-2H-quinolin-1-yl)-methanone,
[2-(3-bromo-phenoxy)-pyridin-3-yl]-(3,4-dihydro-2H-quinolin-1-yl)-methanone,
[2-(2,5-dichloro-phenoxy)-pyridin-3-yl]-(3,4-dihydro-2H-quinolin-1-yl)-methanone,
[2-(3-chloro-phenoxy)-5-fluoro-pyridin-3-yl]-(3,4-dihydro-2H-quinolin-1-yl)-methanone,
[2-(2,5-difluoro-phenoxy)-5-fluoro-pyridin-3-yl]-(3,4-dihydro-2H-quinolin-1-yl)-methanone,
[5-chloro-2-(2,5-dichloro-phenoxy)-pyridin-3-yl]-(3,4-dihydro-2H-quinolin-1-yl)-methanone,
[5-chloro-2-(2,5-difluoro-phenoxy)-pyridin-3-yl]-(3,4-dihydro-2H-quinolin-1-yl)-methanone,
[2-(2,5-dichloro-phenoxy)-6-trifluoromethyl-pyridin-3-yl]-(3,4-dihydro-2H-quinolin-1-yl)-methanone,
[2-(3-chloro-phenoxy)-pyridin-3-yl]-(2,3-dihydro-benzo[1,4]oxazin-4-yl)-methanone,
[2-(2,5-dichloro-phenoxy)-pyridin-3-yl]-(6-methyl-3,4-dihydro-2H-quinolin-1-yl)-methanone,
2-(2,5-dichloro-phenoxy)-N-ethyl-N-phenyl-nicotinamide,
(7-chloro-3,4-dihydro-2H-quinolin-1-yl)-[2-(2,5-dichloro-phenoxy)-pyridin-3-yl]-methanone,
[2-(2,5-dichloro-phenoxy)-pyridin-3-yl]-(7-fluoro-3,4-dihydro-2H-quinolin-1-yl)-methanone,
2-(2,5-dichloro-phenoxy)-N-methyl-N-phenyl-nicotinamide,
[2-(2,5-dichloro-phenoxy)-pyridin-3-yl]-(2,3-dihydro-benzo[1,4]oxazin-4-yl)-methanone,
[2-(2,5-dichloro-phenoxy)-pyridin-3-yl]-(6-fluoro-3,4-dihydro-2H-quinolin-1-yl)-methanone,
[2-(2,5-dichloro-phenoxy)-pyridin-3-yl]-(6,7-difluoro-3,4-dihydro-2H-quinolin-1-yl)-methanone,
[2-(2,5-dichloro-phenoxy)-pyridin-3-yl]-(2,3-dihydro-benzo[1,4]thiazin-4-yl)-methanone,
N-(2-chloro-phenyl)-2-(2,5-dichloro-phenoxy)-N-methyl-nicotinamide,
2-(2,5-dichloro-phenoxy)-N-methyl-N-o-tolyl-nicotinamide,
2-(2,5-dichloro-phenoxy)-N-(2-methoxy-phenyl)-N-methyl-nicotinamide,
N-biphenyl-2-yl-2-(2,5-dichloro-phenoxy)-N-methyl-nicotinamide,
[2-(2,5-dichloro-phenoxy)-pyridin-3-yl]-(6,8-difluoro-3,4-dihydro-2H-quinolin-1-yl)-methanone,
2-(2,5-dichloro-phenoxy)-N-(2-ethyl-phenyl)-N-methyl-nicotinamide,
N-(3-chloro-pyridin-2-yl)-2-(2,5-dichloro-phenoxy)-N-methyl-nicotinamide,
N-(4-chloro-pyridin-3-yl)-2-(2,5-dichloro-phenoxy)-N-methyl-nicotinamide,
2-(2,5-dichloro-phenoxy)-N-(2-methoxy-pyridin-3-yl)-N-methyl-nicotinamide,
N-(3-chloro-2-methyl-phenyl)-2-(2,5-dichloro-phenoxy)-N-methyl-nicotinamide,
N-(5-chloro-2-methyl-phenyl)-2-(2,5-dichloro-phenoxy)-N-methyl-nicotinamide,
N-(2-chloro-6-methyl-phenyl)-2-(2,5-dichloro-phenoxy)-N-methyl-nicotinamide,
2-(2,5-dichloro-phenoxy)-N-(2,6-dimethyl-phenyl)-N-methyl-nicotinamide,
2-(2,5-dichloro-phenoxy)-N-(2-methoxy-6-methyl-phenyl)-N-methyl-nicotinamide,
2-(2,5-dichloro-phenoxy)-N-(5-fluoro-2-methoxy-phenyl)-N-methyl-nicotinamide,
N-(5-chloro-2-methoxy-phenyl)-2-(2,5-dichloro-phenoxy)-N-methyl-nicotinamide,
N-(4-chloro-2-methyl-phenyl)-2-(2,5-dichloro-phenoxy)-N-methyl-nicotinamide,
2-(2,5-dichloro-phenoxy)-N-(2,3-dimethyl-phenyl)-N-methyl-nicotinamide,
2-(2,5-dichloro-phenoxy)-N-(2,4-dimethyl-phenyl)-N-methyl-nicotinamide,
2-(2,5-dichloro-phenoxy)-N-(2-methoxy-5-methyl-phenyl)-N-methyl-nicotinamide,
2-(2,5-dichloro-phenoxy)-N-(2,6-dimethoxy-phenyl)-N-methyl-nicotinamide,
N-(6-chloro-4-methyl-pyridin-3-yl)-2-(2,5-dichloro-phenoxy)-N-methyl-nicotinamide, N-(2-cyano-phenyl)-2-(2,5-dichloro-phenoxy)-N-methyl-nicotinamide,
2-(2,5-dichloro-phenoxy)-N-(2-fluoro-phenyl)-N-methyl-nicotinamide,
2-(2,5-dichloro-phenoxy)-N-(2,6-difluoro-phenyl)-N-methyl-nicotinamide,
2-(2,5-dichloro-phenoxy)-N-methyl-N-(2-pyrrol-1-yl-phenyl)-nicotinamide,
2-(2,5-dichloro-phenoxy)-N-(2,4-difluoro-phenyl)-N-methyl-nicotinamide,
[2-(2,5-dichloro-phenoxy)-pyridin-3-yl]-(2-methyl-3,4-dihydro-2H-quinolin-1-yl)-methanone,
[2-(2,5-dichloro-phenoxy)-pyridin-3-yl]-(8-fluoro-6-methyl-3,4-dihydro-2H-quinolin-1-yl)-methanone,
N-(2-chloro-4-methyl-pyridin-3-yl)-2-(2,5-dichloro-phenoxy)-N-methyl-nicotinamide,
[2-(2,5-dichloro-phenoxy)-pyridin-3-yl]-(8-methoxy-3,4-dihydro-2H-quinolin-1-yl)-methanone,
(6-chloro-3,4-dihydro-2H-quinolin-1-yl)-[2-(2,5-dichloro-phenoxy)-pyridin-3-yl]-methanone,
[2-(2,5-dichloro-phenoxy)-pyridin-3-yl]-(6-fluoro-2,3-dihydro-benzo[1,4]oxazin-4-yl)-methanone,
[2-(2,5-dichloro-phenoxy)-pyridin-3-yl]-(6,8-difluoro-2,3-dihydro-benzo[1,4]oxazin-4-yl)-methanone,
[2-(2,5-dichloro-phenoxy)-pyridin-3-yl]-(4-phenyl-3,4-dihydro-2H-quinoxalin-1-yl)-methanone,
2-(2,5-dichloro-phenoxy)-N-(4-methoxy-pyridin-3-yl)-N-methyl-nicotinamide,
[2-(2,4-dichloro-phenoxy)-pyridin-3-yl]-(3,4-dihydro-2H-quinolin-1-yl)-methanone,
[2-(3-chloro-4-fluoro-phenoxy)-pyridin-3-yl]-(6-methyl-3,4-dihydro-2H-quinolin-1-yl)-methanone,
[2-(3-chloro-4-fluoro-phenoxy)-pyridin-3-yl]-(3,4-dihydro-2H-[1,5]naphthyridin-1-yl)-methanone,
[2-(3-chloro-4-fluoro-phenoxy)-pyridin-3-yl]-(6,7-difluoro-3,4-dihydro-2H-quinolin-1-yl)-methanone,
[2-(2,5-dichloro-phenoxy)-5-fluoro-pyridin-3-yl]-(2-methyl-3,4-dihydro-2H-quinolin-1-yl)-methanone,
[2-(2,5-dichloro-phenoxy)-5-fluoro-pyridin-3-yl]-(2,3-dihydro-benzo[1,4]oxazin-4-yl)-methanone,
1-[2-(2,5-dichloro-phenoxy)-5-fluoro-pyridine-3-carbonyl]-1,2,3,4-tetrahydro-benzo[b]azepin-5-one,
[2-(2,5-dichloro-phenoxy)-5-fluoro-pyridin-3-yl]-(3,4-dihydro-2H-quinolin-1-yl)-methanone,
2-(2,5-dichloro-phenoxy)-N-ethyl-5-fluoro-N-phenyl-nicotinamide,
[2-(3-chloro-phenoxy)-5-fluoro-pyridin-3-yl]-(6,7-difluoro-3,4-dihydro-2H-quinolin-1-yl)-methanone,
[2-(3-chloro-4-fluoro-phenoxy)-5-fluoro-pyridin-3-yl]-(3,4-dihydro-2H-quinolin-1-yl)-methanone,
[2-(3-chloro-4-fluoro-phenoxy)-5-fluoro-pyridin-3-yl]-(6,7-difluoro-3,4-dihydro-2H-quinolin-1-yl)-methanone,
[2-(3-chloro-4-fluoro-phenoxy)-5-fluoro-pyridin-3-yl]-(8-methyl-3,4-dihydro-2H-quinolin-1-yl)-methanone,
[3-(2,5-dichloro-phenoxy)-pyridin-4-yl]-(3,4-dihydro-2H-quinolin-1-34)-methanone,
[3-(2,5-dichloro-phenoxy)-pyridin-4-yl]-(7-fluoro-3,4-dihydro-2H-quinolin-1-yl)-methanone,
[3-(2,5-dichloro-phenoxy)-pyridin-4-yl]-(6-fluoro-3,4-dihydro-2H-quinolin-1-yl)-methanone,
[3-(2,5-dichloro-phenoxy)-pyridin-4-yl]-(6,8-difluoro-3,4-dihydro-2H-quinolin-1-yl)-methanone,
3-(2,5-dichloro-phenoxy)-N-methyl-N-o-tolyl-isonicotinamide,
N-(2-chloro-phenyl)-3-(2,5-dichloro-phenoxy)-N-methyl-isonicotinamide,
3-(2,5-dichloro-phenoxy)-N-(2-methoxy-phenyl)-N-methyl-isonicotinamide,
[3-(2,4-dichloro-phenoxy)-pyridin-4-yl]-(7-fluoro-3,4-dihydro-2H-quinolin-1-yl)-methanone,
[3-(2,4-dichloro-phenoxy)-pyridin-4-yl]-(6-fluoro-3,4-dihydro-2H-quinolin-1-yl)-methanone,
[3-(2,4-dichloro-phenoxy)-pyridin-4-yl]-(6,8-difluoro-3,4-dihydro-2H-quinolin-1-yl)-methanone,
3-(2,4-dichloro-phenoxy)-N-methyl-N-o-tolyl-isonicotinamide,
N-(2-chloro-phenyl)-3-(2,4-dichloro-phenoxy)-N-methyl-isonicotinamide,
3-(2,4-dichloro-phenoxy)-N-(2-methoxy-phenyl)-N-methyl-isonicotinamide,
3-(2,4-dichloro-phenoxy)-N-(2-methoxy-pyridin-3-yl)-N-methyl-isonicotinamide,
[3-(3-chloro-4-fluoro-phenoxy)-pyridin-4-yl]-(7-fluoro-3,4-dihydro-2H-quinolin-1-yl)-methanone,
[3-(3-chloro-4-fluoro-phenoxy)-pyridin-4-yl]-(6-fluoro-3,4-dihydro-2H-quinolin-1-yl)-methanone,
[3-(3-chloro-4-fluoro-phenoxy)-pyridin-4-yl]-(6,8-difluoro-3,4-dihydro-2H-quinolin-1-yl)-methanone,
3-(3-chloro-4-fluoro-phenoxy)-N-methyl-N-o-tolyl-isonicotinamide,
3-(3-chloro-4-fluoro-phenoxy)-N-(2-chloro-phenyl)-N-methyl-isonicotinamide,
3-(3-chloro-4-fluoro-phenoxy)-N-(2-methoxy-phenyl)-N-methyl-isonicotinamide,
3-(3-chloro-4-fluoro-phenoxy)-N-(2-methoxy-pyridin-3-yl)-N-methyl-isonicotinamide,
[2-(2,5-dichloro-phenoxy)-phenyl]-(3,4-dihydro-2H-quinolin-1-yl)-methanone,
[2-(2,5-dichloro-phenoxy)-phenyl]-(6,7-difluoro-3,4-dihydro-2H-quinolin-1-yl)-methanone,
[2-(2,5-dichloro-phenoxy)-phenyl]-(2-methyl-2,3-dihydro-indol-1-yl)-methanone,
[2-(2,5-dichloro-phenoxy)-5-fluoro-phenyl]-(3,4-dihydro-2H-quinolin-1-yl)-methanone,
[2-(2,5-dichloro-phenoxy)-5-fluoro-phenyl]-(2-methyl-3,4-dihydro-2H-quinolin-1-yl)-methanone,
[2-(2,5-dichloro-phenoxy)-5-fluoro-phenyl]-(8-methyl-3,4-dihydro-2H-quinolin-1-yl)-methanone,
[2-(2,5-dichloro-phenoxy)-5-fluoro-phenyl]-(6-methyl-3,4-dihydro-2H-quinolin-1-yl)-methanone,
[2-(2,5-dichloro-phenoxy)-5-fluoro-phenyl]-(2,3-dihydro-benzo[1,4]oxazin-4-yl)-methanone,
2-(2,5-dichloro-phenoxy)-5-fluoro-N-methyl-N-phenyl-benzamide,
4-(2,5-dichloro-phenoxy)-3-(3,4-dihydro-2H-quinoline-1-carbonyl)-benzonitrile,
[2-(2,5-dichloro-phenoxy)-phenyl]-(8-fluoro-6-methyl-3,4-dihydro-2H-quinolin-1-yl)-methanone,
[2-(2,5-dichloro-phenoxy)-phenyl]-(6,8-difluoro-3,4-dihydro-2H-quinolin-1-yl)-methanone,
or pharmaceutically acceptable salts thereof.

Further preferred compounds of formula I are the following:
[2-(2,5-dichloro-phenoxy)-pyridin-3-yl]-(3,4-dihydro-2H-quinoxalin-1-yl)-methanone,
[2-(2,5-dichloro-phenoxy)-pyridin-3-yl]-(4-methyl-3,4-dihydro-2H-quinoxalin-1-yl)-methanone,
[2-(2,5-dichloro-phenoxy)-pyridin-3-yl]-(4-isopropyl-3,4-dihydro-2H-quinoxalin-1-yl)-methanone,
(4-cyclopropyl-3,4-dihydro-2H-quinoxalin-1-yl)-[2-(2,5-dichloro-phenoxy)-pyridin-3-yl]-methanone,
(4-cyclobutyl-3,4-dihydro-2H-quinoxalin-1-yl)-[2-(2,5-dichloro-phenoxy)-pyridin-3-yl]-methanone,

[2-(2,5-dichloro-phenoxy)-pyridin-3-yl]-(4-oxetan-3-yl-3,4-dihydro-2H-quinoxalin-1-yl)-methanone,
1-[2-(2,5-dichloro-phenoxy)-pyridine-3-carbonyl]-2,3-dihydro-1H-quinolin-4-one,
[2-(2,5-dichloro-phenoxy)-pyridin-3-yl]-(4-methylene-3,4-dihydro-2H-quinolin-1-yl)-methanone,
[2-(2,5-dichloro-phenoxy)-pyridin-3-yl]-[4-(3,3-difluoro-azetidin-1-yl)-3,4-dihydro-2H-quinolin-1-yl]-methanone,
N-(2-cyclopropyl-phenyl)-2-(2,5-dichloro-phenoxy)-N-methyl-nicotinamide,
2-(2,5-dichloro-phenoxy)-N-methyl-N-(2-methylsulfanyl-phenyl)-nicotinamide,
2-(2,5-dichloro-phenoxy)-N-methyl-N-[2-(2-methyl-2H-pyrazol-3-yl)-phenyl]-nicotinamide,
N-(2-amino-phenyl)-2-(2,5-dichloro-phenoxy)-N-methyl-nicotinamide,
2-(2,5-dichloro-phenoxy)-N-(2,5-dichloro-phenyl)-N-methyl-nicotinamide,
[2-(2,5-dichloro-phenoxy)-pyridin-3-yl]-(2,3,3a,4-tetrahydro-1H-pyrrolo[1,2-a]quinoxalin-5-yl)-methanone,
[2-(2,5-dichloro-phenoxy)-pyridin-3-yl]-(4-isobutyl-3,4-dihydro-2H-quinoxalin-1-yl)-methanone,
(4-cyclopropylmethyl-3,4-dihydro-2H-quinoxalin-1-yl)-[2-(2,5-dichloro-phenoxy)-pyridin-3-yl]-methanone,
(4-cyclobutylmethyl-3,4-dihydro-2H-quinoxalin-1-yl)-[2-(2,5-dichloro-phenoxy)-pyridin-3-yl]-methanone,
acetic acid 2-{-4-[2-(2,5-dichloro-phenoxy)-pyridine-3-carbonyl]-3,4-dihydro-2H-quinoxalin-1-yl}-ethyl ester,
{4-[2-(2,5-dichloro-phenoxy)-pyridine-3-carbonyl]-3,4-dihydro-2H-quinoxalin-1-yl}-acetic acid ethyl ester,
{4-[2-(2,5-dichloro-phenoxy)-pyridine-3-carbonyl]-3,4-dihydro-2H-quinoxalin-1-yl}-acetic acid,
3-(4-{-4-[2-(2,5-dichloro-phenoxy)-pyridine-3-carbonyl]-3,4-dihydro-2H-quinoxaline-1-sulfonyl}-phenyl)-propionic acid,
(3,4-dihydro-2H-quinolin-1-yl)-[2-(2-fluoro-5-trifluoromethyl-phenoxy)-pyridin-3-yl]-methanone,
2-(2,5-dichloro-phenoxy)-5-fluoro-N-(2-methoxy-pyridin-3-yl)-N-methyl-nicotinamide,
N-(2,6-dichloro-3-methoxy-phenyl)-2-(2,5-dichloro-phenoxy)-5-fluoro-N-methyl-nicotinamide,
[2-(2,5-dichloro-phenoxy)-5-fluoro-pyridin-3-yl]-(3,4-dihydro-2H-quinoxalin-1-yl)-methanone,
1-[2-(2,5-dichloro-phenoxy)-5-fluoro-pyridine-3-carbonyl]-1,2,3,4-tetrahydro-quinoline-4-carboxylic acid methyl ester,
[2-(2,5-dichloro-phenoxy)-5-fluoro-pyridin-3-yl]-(4H-pyrrolo[1,2-a]quinoxalin-5-yl)-methanone,
(4-cyclobutyl-3,4-dihydro-2H-quinoxalin-1-yl)-[2-(2,5-dichloro-phenoxy)-5-fluoro-pyridin-3-yl]-methanone,
[2-(2,5-dichloro-phenoxy)-5-fluoro-pyridin-3-yl]-(4-furan-3-ylmethyl-3,4-dihydro-2H-quinoxalin-1-yl)-methanone,
(4-cyclobutylmethyl-3,4-dihydro-2H-quinoxalin-1-yl)-[2-(2,5-dichloro-phenoxy)-5-fluoro-pyridin-3-yl]-methanone,
[2-(2,5-dichloro-phenoxy)-5-fluoro-pyridin-3-yl]-[4-(3,3,3-trifluoro-propyl)-3,4-dihydro-2H-quinoxalin-1-yl]-methanone,
{4-[2-(2,5-dichloro-phenoxy)-5-fluoro-pyridine-3-carbonyl]-3,4-dihydro-2H-quinoxalin-1-yl}-acetic acid ethyl ester,
{-4-[2-(2,5-dichloro-phenoxy)-5-fluoro-pyridine-3-carbonyl]-3,4-dihydro-2H-quinoxalin-1-yl}-acetic acid,
3-{4-[2-(2,5-dichloro-phenoxy)-5-fluoro-pyridine-3-carbonyl]-3,4-dihydro-2H-quinoxalin-1-yl}-propionic acid ethyl ester,
3-{-4-[2-(2,5-dichloro-phenoxy)-5-fluoro-pyridine-3-carbonyl]-3,4-dihydro-2H-quinoxalin-1-yl}-2-methyl-propionic acid,
4-{4-[2-(2,5-dichloro-phenoxy)-5-fluoro-pyridine-3-carbonyl]-3,4-dihydro-2H-quinoxalin-1-yl}-butyric acid ethyl ester,
5-{4-[2-(2,5-dichloro-phenoxy)-5-fluoro-pyridine-3-carbonyl]-3,4-dihydro-2H-quinoxalin-1-yl}-pentanoic acid ethyl ester,
6-{-4-[2-(2,5-dichloro-phenoxy)-5-fluoro-pyridine-3-carbonyl]-3,4-dihydro-2H-quinoxalin-1-yl}-hexanoic acid methyl ester,
6-{4-[2-(2,5-dichloro-phenoxy)-5-fluoro-pyridine-3-carbonyl]-3,4-dihydro-2H-quinoxalin-1-yl}-hexanoic acid,
4-{-4-[2-(2,5-dichloro-phenoxy)-5-fluoro-pyridine-3-carbonyl]-3,4-dihydro-2H-quinoxaline-1-carbonyl}-benzoic acid methyl ester,
[2-(4-bromo-2,5-dichloro-phenoxy)-pyridin-3-yl]-(4-cyclopropyl-3,4-dihydro-2H-quinoxalin-1-yl)-methanone,
(4-cyclopropyl-3,4-dihydro-2H-quinoxalin-1-yl)-{2-[2,5-dichloro-4-(3-hydroxy-prop-1-ynyl)-phenoxy]-pyridin-3-yl}-methanone,
[2-(4-bromo-2,5-dichloro-phenoxy)-pyridin-3-yl]-(3,4-dihydro-2H-quinolin-1-yl)-methanone,
5-{2,5-dichloro-4-[3-(3,4-dihydro-2H-quinoline-1-carbonyl)-pyridin-2-yloxy]-phenyl}-pent-4-ynoic acid methyl ester,
2-chloro-4-{2,5-dichloro-4-[3-(4-cyclopropyl-3,4-dihydro-2H-quinoxaline-1-carbonyl)-pyridin-2-yloxy]-phenyl-ethynyl}-benzoic acid methyl ester,
2-chloro-4-{2,5-dichloro-4-[3-(4-cyclopropyl-3,4-dihydro-2H-quinoxaline-1-carbonyl)-pyridin-2-yloxy]-phenyl-ethynyl}-benzoic acid,
2-chloro-4-(2-{2,5-dichloro-4-[3-(4-cyclopropyl-3,4-dihydro-2H-quinoxaline-1-carbonyl)-pyridin-2-yloxy]-phenyl}-ethyl)-benzoic acid,
4-(2-{2,5-dichloro-4-[3-(4-cyclopropyl-3,4-dihydro-2H-quinoxaline-1-carbonyl)-pyridin-2-yloxy]-phenyl}-ethyl)-benzoic acid,
4-(2-{2,5-dichloro-4-[3-(4-cyclopropyl-3,4-dihydro-2H-quinoxaline-1-carbonyl)-pyridin-2-yloxy]-phenyl}-ethyl)-3-methoxy-benzoic acid,
3-{2,5-dichloro-4-[3-(4-cyclopropyl-3,4-dihydro-2H-quinoxaline-1-carbonyl)-pyridin-2-yloxy]-phenyl}-acrylic acid,
3-{2,5-dichloro-4-[3-(4-cyclopropyl-3,4-dihydro-2H-quinoxaline-1-carbonyl)-pyridin-2-yloxy]-phenyl}-propionic acid,
4-{2,5-dichloro-4-[3-(4-cyclopropyl-3,4-dihydro-2H-quinoxaline-1-carbonyl)-pyridin-2-yloxy]-phenyl}-but-3-enoic acid methyl ester,
4-{2,5-dichloro-4-[3-(4-cyclopropyl-3,4-dihydro-2H-quinoxaline-1-carbonyl)-pyridin-2-yloxy]-phenyl}-but-3-enoic acid,
4-{2,5-dichloro-4-[3-(4-cyclopropyl-3,4-dihydro-2H-quinoxaline-1-carbonyl)-pyridin-2-yloxy]-phenyl}-butyric acid,
(3-{2,5-dichloro-4-[3-(4-cyclopropyl-3,4-dihydro-2H-quinoxaline-1-carbonyl)-pyridin-2-yloxy]-phenyl}-propionylamino)-acetic acid,
[(3-{2,5-dichloro-4-[3-(4-cyclopropyl-3,4-dihydro-2H-quinoxaline-1-carbonyl)-pyridin-2-yloxy]phenyl}-propionyl)-methyl-amino]-acetic acid,
3-(3-{2,5-dichloro-4-[3-(4-cyclopropyl-3,4-dihydro-2H-quinoxaline-1-carbonyl)-pyridin-2-yloxy]-phenyl}-propionylamino)-propionic acid, 1-(3-{2,5-dichloro-4-[3-(4-cyclopropyl-3,4-dihydro-2H-quinoxaline-1-carbonyl)-pyridin-2-yloxy]-phenyl}-propionyl)-pyrrolidine-2-carboxylic acid,
3-(4-{2,5-dichloro-4-[3-(4-cyclopropyl-3,4-dihydro-2H-quinoxaline-1-carbonyl)-pyridin-2-yloxy]-phenyl}-butyrylamino)-propionic acid,
2,5-dichloro-4-[3-(4-cyclopropyl-3,4-dihydro-2H-quinoxaline-1-carbonyl)-pyridin-2-yloxy]-benzoic acid methyl ester,
{2,5-dichloro-4-[3-(4-cyclopropyl-3,4-dihydro-2H-quinoxaline-1-carbonyl)-pyridin-2-yloxy]-benzoylamino}-acetic acid methyl ester,
(4-cyclopropyl-3,4-dihydro-2H-quinoxalin-1-yl)-[2-(2,5-dichloro-phenoxy)-phenyl]methanone,
[3-(2,5-dichloro-phenoxy)-pyridin-4-yl]-(2,3-dihydro-benzo[1,4]oxazin-4-yl)-methanone,
or pharmaceutically acceptable salts thereof.

Particularly preferred compounds of formula I of the present invention are the following:
[2-(3-chloro-4-fluoro-phenoxy)-pyridin-3-yl]-(3,4-dihydro-2H-quinolin-1-yl)-methanone,
[2-(2,5-dichloro-phenoxy)-pyridin-3-yl]-(3,4-dihydro-2H-quinolin-1-yl)-methanone,
2-(2,5-dichloro-phenoxy)-N-ethyl-N-phenyl-nicotinamide,
[2-(2,5-dichloro-phenoxy)-pyridin-3-yl]-(7-fluoro-3,4-dihydro-2H-quinolin-1-yl)-methanone,
[2-(2,5-dichloro-phenoxy)-pyridin-3-yl]-(6-fluoro-3,4-dihydro-2H-quinolin-1-yl)-methanone,
[2-(2,5-dichloro-phenoxy)-pyridin-3-yl]-(6,7-difluoro-3,4-dihydro-2H-quinolin-1-yl)-methanone,
[2-(2,5-dichloro-phenoxy)-pyridin-3-yl]-(2,3-dihydro-benzo[1,4]thiazin-4-yl)-methanone,
2-(2,5-dichloro-phenoxy)-N-methyl-N-o-tolyl-nicotinamide,
2-(2,5-dichloro-phenoxy)-N-(2-methoxy-phenyl)-N-methyl-nicotinamide,
[2-(2,5-dichloro-phenoxy)-pyridin-3-yl]-(6,8-difluoro-3,4-dihydro-2H-quinolin-1-yl)-methanone,
N-(2-chloro-6-methyl-phenyl)-2-(2,5-dichloro-phenoxy)-N-methyl-nicotinamide,
2-(2,5-dichloro-phenoxy)-N-(5-fluoro-2-methoxy-phenyl)-N-methyl-nicotinamide,
[2-(2,5-dichloro-phenoxy)-5-fluoro-pyridin-3-yl]-(3,4-dihydro-2H-quinolin-1-yl)-methanone,
[3-(2,5-dichloro-phenoxy)-pyridin-4-yl]-(3,4-dihydro-2H-quinolin-1-yl)-methanone,
[3-(2,5-dichloro-phenoxy)-pyridin-4-yl]-(7-fluoro-3,4-dihydro-2H-quinolin-1-yl)-methanone,
[3-(2,5-dichloro-phenoxy)-pyridin-4-yl]-(6-fluoro-3,4-dihydro-2H-quinolin-1-yl)-methanone,
[3-(2,5-dichloro-phenoxy)-pyridin-4-yl]-(6,8-difluoro-3,4-dihydro-2H-quinolin-1-yl)-methanone,
3-(2,5-dichloro-phenoxy)-N-methyl-N-o-tolyl-isonicotinamide,
3-(2,5-dichloro-phenoxy)-N-(2-methoxy-phenyl)-N-methyl-isonicotinamide,
[2-(2,5-dichloro-phenoxy)-phenyl]-(3,4-dihydro-2H-quinolin-1-yl)-methanone,
[2-(2,5-dichloro-phenoxy)-pyridin-3-yl]-(3,4-dihydro-2H-quinoxalin-1-yl)-methanone,
[2-(2,5-dichloro-phenoxy)-pyridin-3-yl]-(4-methyl-3,4-dihydro-2H-quinoxalin-1-yl)-methanone,
(4-cyclopropyl-3,4-dihydro-2H-quinoxalin-1-yl)-[2-(2,5-dichloro-phenoxy)-pyridin-3-yl]-methanone,
(4-cyclobutyl-3,4-dihydro-2H-quinoxalin-1-yl)-[2-(2,5-dichloro-phenoxy)-pyridin-3-yl]-methanone,
[2-(2,5-dichloro-phenoxy)-pyridin-3-yl]-(4-oxetan-3-yl-3,4-dihydro-2H-quinoxalin-1-yl)-methanone,
[2-(2,5-dichloro-phenoxy)-pyridin-3-yl]-(4-methylene-3,4-dihydro-2H-quinolin-1-yl)-methanone,
2-(2,5-dichloro-phenoxy)-N-methyl-N-(2-methylsulfanyl-phenyl)-nicotinamide,
(4-cyclopropylmethyl-3,4-dihydro-2H-quinoxalin-1-yl)-[2-(2,5-dichloro-phenoxy)-pyridin-3-yl]-methanone,
[2-(2,5-dichloro-phenoxy)-5-fluoro-pyridin-3-yl]-(3,4-dihydro-2H-quinoxalin-1-yl)-methanone,
(4-cyclobutyl-3,4-dihydro-2H-quinoxalin-1-yl)-[2-(2,5-dichloro-phenoxy)-5-fluoro-pyridin-3-yl]-methanone,
{4-[2-(2,5-dichloro-phenoxy)-5-fluoro-pyridine-3-carbonyl]-3,4-dihydro-2H-quinoxalin-1-yl}-acetic acid ethyl ester,
[2-(4-bromo-2,5-dichloro-phenoxy)-pyridin-3-yl]-(4-cyclopropyl-3,4-dihydro-2H-quinoxalin-1-yl)-methanone,
(4-cyclopropyl-3,4-dihydro-2H-quinoxalin-1-yl)-{2-[2,5-dichloro-4-(3-hydroxy-prop-1-ynyl)-phenoxy]-pyridin-3-yl}-methanone,
4-(2-{2,5-dichloro-4-[3-(4-cyclopropyl-3,4-dihydro-2H-quinoxaline-1-carbonyl)-pyridin-2-yloxy]-phenyl}-ethyl)-benzoic acid,
3-{2,5-dichloro-4-[3-(4-cyclopropyl-3,4-dihydro-2H-quinoxaline-1-carbonyl)-pyridin-2-yloxy]-phenyl}-prop ionic acid,
4-{2,5-dichloro-4-[3-(4-cyclopropyl-3,4-dihydro-2H-quinoxaline-1-carbonyl)-pyridin-2-yloxy]-phenyl}-but-3-enoic acid methyl ester,
(3-{2,5-dichloro-4-[3-(4-cyclopropyl-3,4-dihydro-2H-quinoxaline-1-carbonyl)-pyridin-2-yloxy]-phenyl}-propionylamino)-acetic acid,
[(3-{2,5-dichloro-4-[3-(4-cyclopropyl-3,4-dihydro-2H-quinoxaline-1-carbonyl)-pyridin-2-yloxy]-phenyl}-propionyl)-methyl-amino]acetic acid,
3-(3-{2,5-dichloro-4-[3-(4-cyclopropyl-3,4-dihydro-2H-quinoxaline-1-carbonyl)-pyridin-2-yloxy]-phenyl}-propionylamino)-propionic acid,
1-(3-{2,5-dichloro-4-[3-(4-cyclopropyl-3,4-dihydro-2H-quinoxaline-1-carbonyl)-pyridin-2-yloxy]-phenyl}-propionyl)-pyrrolidine-2-carboxylic acid,
3-(4-{2,5-dichloro-4-[3-(4-cyclopropyl-3,4-dihydro-2H-quinoxaline-1-carbonyl)-pyridin-2-yloxy]-phenyl}-butyrylamino)-propionic acid,
(4-cyclopropyl-3,4-dihydro-2H-quinoxalin-1-yl)-[2-(2,5-dichloro-phenoxy)-phenyl]-methanone,
[3-(2,5-dichloro-phenoxy)-pyridin-4-yl]-(2,3-dihydro-benzo[1,4]oxazin-4-yl)-methanone,
or pharmaceutically acceptable salts thereof.

The pharmaceutically acceptable salts of the compounds of formula I also individually constitute preferred compounds of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a carboxylic acid of the formula II

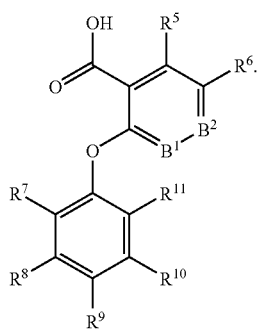

wherein $B^1$, $B^2$ and $R^5$ to $R^{11}$ are as defined above, with an amine of the formula III

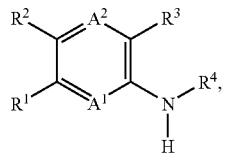

wherein $A^1$, $A^2$ and $R^1$ to $R^4$ are as defined above, in the presence of a coupling reagent under basic conditions to obtain a compound of the formula I

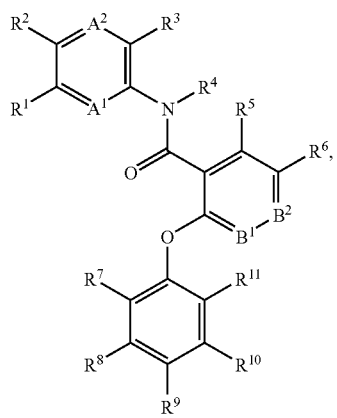

wherein $A^1$, $A^2$, $B^1$, $B^2$ and $R^1$ to $R^{11}$ are as defined above, and, if desired, converting the compound obtained into a pharmaceutically acceptable salt. or, alternatively, b) coupling a compound of the formula IV

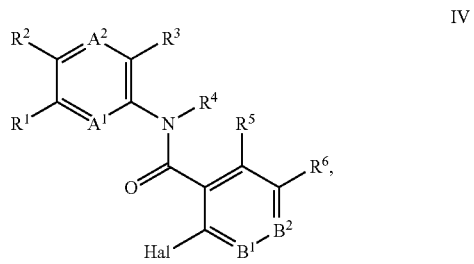

wherein $A^1$, $A^2$, $B^1$, $B^2$ and $R^1$ to $R^6$ are as defined above and Hal means a halogen atom or sulfonate, with a phenol of the formula V

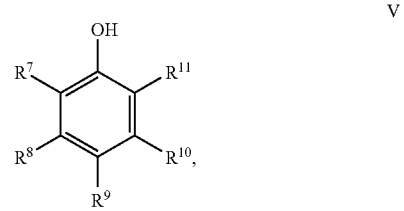

wherein $R^7$ to $R^{11}$ are as defined above, in the presence of a copper (I) source to obtain a compound of the formula I

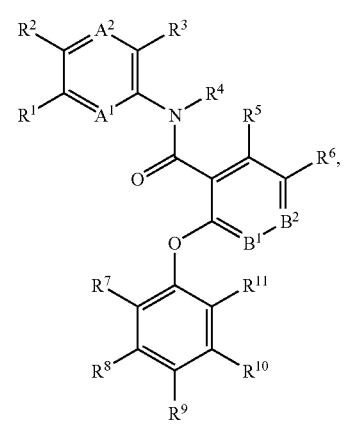

wherein $A^1$, $A^2$, $B^1$, $B^2$ and $R^1$ to $R^{11}$ are as defined above, and, if desired, converting the compound obtained into a pharmaceutically acceptable salt.

Appropriate coupling agents are for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), 2-chloro-1-methylpyridinium iodide or benzotriazol-1-yloxytris(dimethylamino)phosphonium hexafluorophoshate (BOP). "Under basic conditions" means the presence of a base such as diisopropylethylamine, triethylamine, N-methylmorpholine or 4-(dimethylamino)-pyridine. The reaction is carried out in a suitable solvent such as for example N,N-dimethylformamide (DMF), dimethylacetamide (DMAc), dichloromethane or dioxane, at temperatures between 0° C. and 100° C., whereby heating can be achieved by conventional heating or by microwave irradiation.

A copper (I) source means a copper (I) salt such as copper (I) bromide or copper (I) iodide or copper (I) complexes which typically are more soluble in organic solvents such as tetrakis(acetonitrile)copper(I) hexafluorophosphate. Additionally, the coupling can be conducted in the presence of copper metal powder. The coupling is preferably carried out under heating or microwave assisted heating (typically to a temperature between 100 and 200° C., or up to the boiling temperature of the solvent) in an aprotic solvent such as N,N-dimethylformamide (DMF), dimethylacetamide (DMAc), N-methylpyrrolidone (NMP), sulfolane, ethylene glycol, acetonitrile and THF or mixtures thereof. Optionally a tertiary amine such as triethylamine, N-ethyl diisopropylamine (Hünigs base) or pyridine is also present.

The invention further relates to compounds of formula I as defined above obtainable according to a process as defined above.

In more detail, compounds of formula I according to the present invention can be prepared by the methods and procedures given below. A typical procedure for the preparation of compounds of formula I is illustrated in Scheme 1.

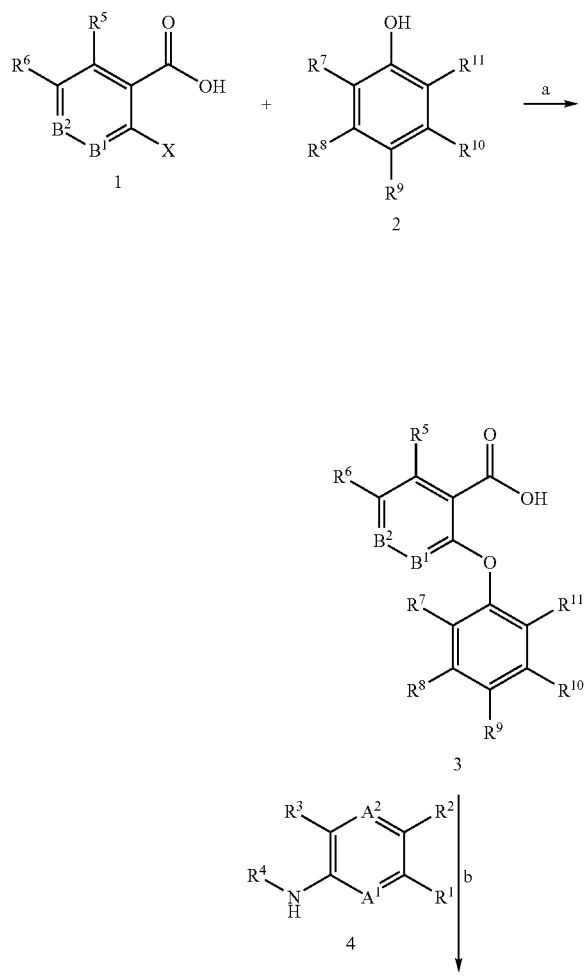

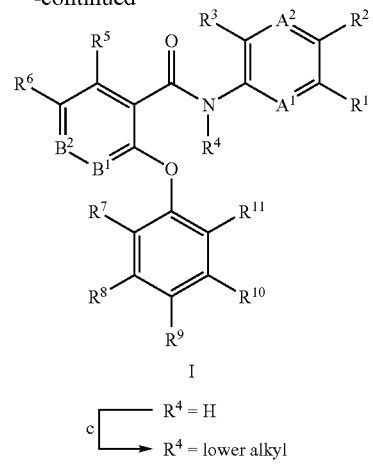

Copper-mediated C(aryl)-O coupling of halo aryl-carboxylic acids of the general structure 1 with phenols 2 (classical Ullmann and Goldberg reaction and variations thereof; for a review see: S. V. Ley and A. W. Thomas *Angew. Chem. Int. Ed.* 2003, 42, 5400-5449) at room or elevated temperatures provide diaryl ethers 3 (Scheme 1, Step a), whereby X is usually a halogene such as iodine, bromine or chlorine (in the case of the Chan-Evans-Lam reaction X might also be an aryl boronic acid derivative). In order to enhance the rate of conversion heating might be applied, whereby conventional heating or microwave assisted heating might be employed using a suitable microwave irradiation apparatus. Furthermore the reaction can be conducted in the presence of or without solvent (typically an aprotic polar solvent such as DMF (N,N-dimethylformamide), DMAc (dimethylacetamide), NMP (N-methylpyrrolidone), ethylene glycol, acetonitrile and THF or mixtures thereof; in some cases also a less polar solvent such as toluene might be appropriate) and in the presence of or without a tertiary amine base such as triethylamine, N-ethyl diisopropylamine (Hünigs base) or pyridine and in the presence with or without a copper(I) source such as copper(I) bromide or copper(I) iodide. In some cases it might be advisable to conduct the reaction in the presence of copper (I) complexes with higher solubility such as tetrakis(acetonitrile)copper(I) hexafluorophosphate (e.g., U.S. Ser. No. 06/028 7297 A1 (Johnson & Johnson)). Said reaction might be conducted with or without copper metal (e.g., copper(0) nanopowder). Alternatively the copper-mediated C(aryl)-O coupling reaction can be executed under basic conditions by using $K_2CO_3$, $Cs_2CO_3$, KOH, $NaOCH_3$, KOtert-Bu or NaH (nulceophilic aromatic substitution type reaction), whereby X is a suitable leaving group such as chlorine, bromine, iodine, $SO_2$alkyl, $SO_2$-fluoroalkyl, $SO_2$aryl, mesylate (methanesulfonate) or triflate (trifluoro-methanesulfonate). The starting materials of general structure 1 (e.g., 2-chloro-nicotinic acids, 2-bromo-nicotinic acids or 3-bromo-isonicotinic acids) are known compounds and are commercially available or can be prepared by numerous methods using conventional reaction procedures generally known in the art. For instance, the carboxylic acid function in aryls 1 might be prepared from the corresponding benzonitriles or from the corresponding carboxylic esters by applying standard reaction conditions used for such type of conversions known to a person skilled in the art such as by acid catalyzed hydrolysis (e.g., $H_2SO_4$, HCl) or by stirring with alkaline hydroxides (e.g., LiOH, NaOH, KOH) in a solvent mixture consisting typically of THF and water, optionally in the presence of alcohols such as methanol or ethanol) whereby conventional heating or heating by microwave irradiation might be applied. These reactions can take place over a wide range of temperatures ranging from ambient temperature to the reflux temperature of the solvent employed. The phenols of formula 2 are also known compounds and are commercially available or can be prepared by numerous methods using conventional reaction procedures generally known in the art.

Amide coupling of aryl ether intermediates 3 with optionally substituted cycloalkyl/aryl amines 4 (either commercially available or accessible by methods described in references or by methods known in the art) gives access to target structures of general structure (I) (Scheme 1, Step b). Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y. 1999) and can be accomplished by employing the usage of coupling reagents such as, e.g., N,N-carbonyldiimidazole (CDI), N,N-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-thazolo[4,5-b]pyridinium-3-oxide hexafluorophosphate (HATU), 1-hydroxy-1,2,3-benzotriazole (HOBT), O-benzotriazol-1-yl-N,N,N,N-tetramethyluronium tetrafluoroborate (TBTU) or 2-chloro-1-methylpyridinium iodide (Mukaiyama reagent; E. Bald, K. Saigo and T. Mukaiyama Chem. Lett. 1975, 4, 1163-1166) in a suitable solvent like, e.g., N,N-dimethylformamide (DMF), dimethylacetamide (DMAc), dichloromethane or dioxane, optionally in the presence of a base (e.g., triethylamine, diisopropylethylamine or 4-(dimethylamino)pyridine). Alternatively, target structures (I) can be obtained by converting intermediates 3 into their acid chlorides by treatment with, e.g., thionyl chloride, neat or optionally in a solvent such as, e.g., dichloromethane and reaction of the acid chloride with amines 4 in an appropriate solvent such as, e.g., dichloromethane or DMF (N,N-dimethylformamide) and a base such as, e.g., triethylamine, N-ethyl diisopropylamine (Hünigs base), pyridine diisopropylethylamine or 4-(dimethylamino)pyridine, whereby theses reactions can take place over a wide range of temperatures ranging from ambient temperature to the reflux temperature of the solvent employed. In cases where aniline 4 is a primary amine leading to secondary amides alkylation (e.g., methylation) of the amide bond can be achieved by reaction with alkyl halides (e.g., methyl iodide or methyl bromide) in the presence of a base such as sodium hydride in an appropriate solvent like DMF (N,N-dimethylformamide), THF or mixtures thereof, at rt to elevated temperatures (Scheme 1, Step c).

Target structures of formula I can also be accomplished employing an inverted reaction sequence, namely by first forming the amide bond between aryl carboxylic acids 1 and cycloalkyl/aryl amines 4 (Scheme 2, Step a), followed by copper-mediated C(aryl)-O coupling of the intermediate 5 with phenols 2 (Scheme 2, Step b). This provides then access to the target structures (I), which in case of a secondary amide eventually are further alkylated (Scheme 2, Step c). In cases where the amine moiety is the desired group of variation the strategy outlined in Scheme 1 is of particular interest. In contrary, the strategy depicted in Scheme 2 allows the phenol part of the structure to be varied in a rapid and parallel fashion.

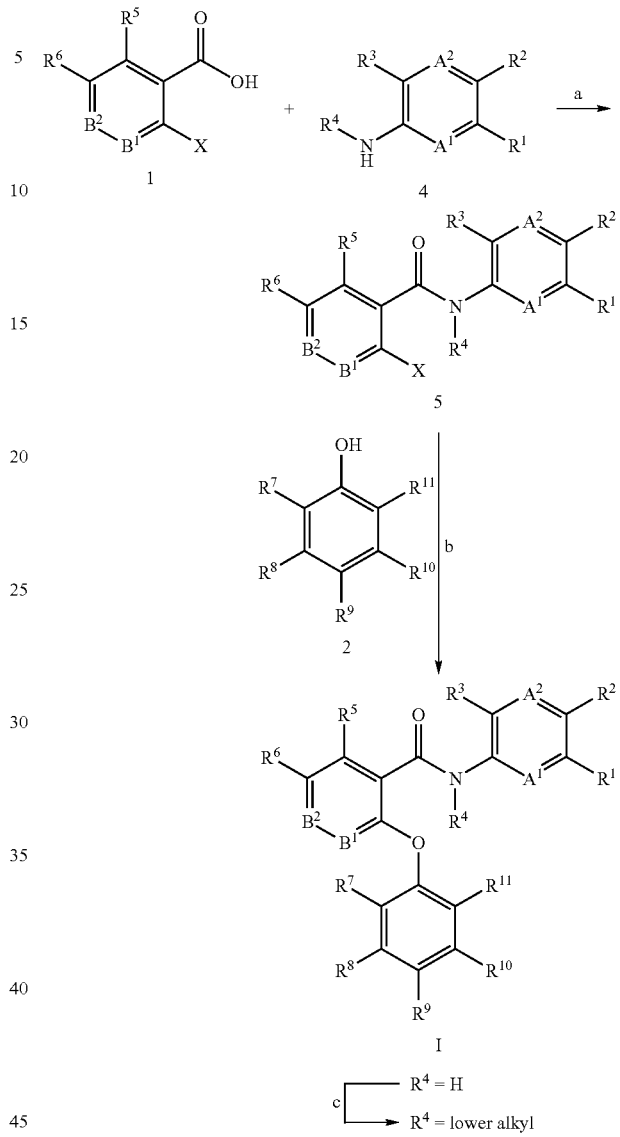

Scheme 2

As described herein before, the compounds of formula I of the present invention can be used as medicaments for the treatment of diseases which are associated with the modulation of GPBAR1 activity.

As compounds of formula I of the invention are agonists of the GPBAR1 receptor, the compounds will be useful for lowering glucose, lipids, and insulin resistance in diabetic patients and in non-diabetic patients who have impaired glucose tolerance or who are in a pre-diabetic condition. The compounds of formula I are further useful to ameliorate hyperinsulinemia, which often occurs in diabetic or pre-diabetic patients, by modulating the swings in the level of serum glucose that often occurs in these patients. The compounds of formula I are also useful in reducing the risks associated with metabolic syndrome, in reducing the risk of developing atherosclerosis or delaying the onset of atherosclerosis, and reducing the risk of angina, claudication, heart attack, stroke, and coronary artery disease. By keeping hyperglycemia under control, the compounds are useful to delay or for preventing vascular restenosis and diabetic retinopathy.

The compounds of formula I of the present invention are useful in improving or restoring β-cell function, so that they may be useful in treating type 1 diabetes or in delaying or preventing a patient with type 2 diabetes from needing insulin therapy. The compounds may be useful for reducing appetite and body weight in obese subjects and may therefore be useful in reducing the risk of co-morbidities associated with obesity such as hypertension, atherosclerosis, diabetes, and dyslipidemia. By elevating the levels of active GLP-1 in vivo, the compounds are useful in treating neurological disorders such as Alzheimer's disease, multiple sclerosis, and schizophrenia.

Thus, the expression "diseases which are associated with the modulation of GPBAR1 activity" means diseases such as metabolic, cardiovascular, and inflammatory diseases, for example diabetes, particularly type 2 diabetes or gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, rheumatoid arthritis, asthma, chronic obstructive pulmonary disease (COPD), psoriasis, ulcerative colitis, irritable bowel disease (IBS), allergy diseases, fatty liver, liver fibrosis, liver cirrhosis, liver colestasis, kidney fibrosis, anorexia nervosa, bulimia nervosa and neurological disorders such as Alzheimer's disease, multiple sclerosis, schizophrenia and impaired cognition.

In a preferable aspect, the expression 'diseases which are associated with the modulation of GPBAR1 activity' relates to diabetes, particularly type II diabetes, impaired fasting glucose, impaired glucose tolerance, hyperglycemia, metabolic syndrome, obesity, hypercholesterolemia and dyslipidemia. More preferably, the expression 'diseases which are associated with glucocorticoid receptor modulation' relates to diabetes, preferably type II diabetes, and hyperglycemia.

The invention also relates to pharmaceutical compositions comprising a compound as defined above and a pharmaceutically acceptable carrier and/or adjuvant. More specifically, the invention relates to pharmaceutical compositions useful for the treatment of diseases which are associated with the modulation of GPBAR1 activity.

Further, the invention relates to compounds of formula I as defined above for use as therapeutically active substances, particularly as therapeutically active substances for the treatment of diseases which are associated with the modulation of GPBAR1 activity. Especially preferred are compounds of formula I for use in diabetes, preferably type II diabetes, or hyperglycemia.

In another aspect, the invention relates to a method for the treatment a of diseases which are associated with the modulation of GPBAR1 activity, which method comprises administering a therapeutically active amount of a compound of formula I to a human being or animal. A method for the treatment of diabetes, preferably type II diabetes, or hyperglycemia is preferred.

The invention further relates to the use of compounds of formula I as defined above for the treatment of diseases which are associated with the modulation of GPBAR1 activity.

In addition, the invention relates to the use of compounds of formula I as defined above for the preparation of medicaments for the treatment of diseases which are associated with the modulation of GPBAR1 activity. The use of compounds of formula I as defined above for the preparation of medicaments for the treatment of diabetes, preferably type II diabetes, or hyperglycemia is especially preferred.

Also contemplated herein is a combination therapy using one or more compounds of formula I or compositions of the present invention, or a pharmaceutically acceptable salts thereof, in combination with one or more other pharmaceutically active compounds independently selected from the group consisting of the following:

(a) human peroxisome proliferator activated receptor (PPAR) gamma agonists (e.g., thiazolidinediones and glitazones, e.g., rosiglitazone, troglitazone, pioglitazone, englitazone, balaglitazone, and netoglitazone), (b) biguanides such as metformin, metformin hydrochloride, buformin and phenformin, (c) dipeptidyl peptidase IV (DPP-4) inhibitors, such as sitagliptin, sitagliptin phosphate, saxagliptin, vildagliptin, alogliptin, carmegliptin, denagliptin sitagliptin, saxagliptin, and SYR-322, (d) incretins such as glucagon-like peptide-1 (GLP-1) receptor agonists (e.g., Exenatide (Byetta™), NN2211 (Liraglutide), GLP-1 (7-36) amide and its analogs, GLP-1 (7-37) and its analogs, AVE-0010 (ZP-10), R1583 (taspoglutide), GSK-716155 (albiglutide, GSK/Human Genome Sciences), BRX-0585 (Pfizer/Biorexis) and CJC-1134-PC (Exendin-4: PC-DAC™) or glucose-dependent insulinotropic peptide (GIP), (e) insulin or insulin analogs such as LysPro insulin or inhaled formulations comprising insulin, (f) sulfonylureas such as tolazamide, chlorpropamide, glipizide, glimepiride, glyburide, glibenclamide, tolbutamide, acetohexamide or glypizide, (g) α-glucosidase inhibitors such as miglitol, acarbose, epalrestat, or voglibose, (h) cholesterol biosynthesis inhibitors such as HMG CoA reductase inhibitors, e.g., lovastatin, simvastatin, pravastatin, fluvastatin, atorvastatin, cerivastatin, itavastin, nisvastatin and rivastatin, or squalene epoxidase inhibitors, e.g., terbinafine, (i) plasma HDL-raising agents such as CETP inhibitors e.g., anacetrapib, torcetrapib and dalcetrapib, or PPAR alpha agonists, e.g., gemfibronzil, clofibrate, fenofibrate and bezafibrate, (j) PPAR dual alpha/gamma agonists such as muraglitazar, naveglitazar, aleglitazar, tesaglitazar, peliglitazar, farglitazar and JT-501, (k) bile acid sequestrants, e.g., anion exchange resins, or quaternary amines (e.g., cholestyramine or colestipol)), or ileal bile acid transporter inhibitors (BATi);

(l) nicotinyl alcohol, nicotinic acid, niacinamide or salts thereof, (m) cholesterol absorption inhibitors such as ezetimibe or acyl-Coenzyme A:cholesterol O-acyl transferase (ACAT) inhibitors such as avasimibe, (n) selective estrogen receptor modulators such as raloxifene or tamoxifen) or LXR alpha or beta agonists, antagonists or partial agonists (e.g., 22(R)-hydroxycholesterol, 24(S)-hydroxycholesterol, T0901317 or GW3965);

(O) microsomal triglyceride transfer protein (MTP) inhibitors, alpha2-antagonists and imidazolines (e.g., midaglizole, isaglidole, deriglidole, idazoxan, efaroxan, fluparoxan), (p) insulin secretagogues such as linogliride, nateglinide, repaglinide, mitiglinide calcium hydrate or meglitinide);

(q) SGLT-2 inhibitors (e.g., dapagliflozin, sergliflozin and AVE 2268), (s) glucokinase activators such as the compounds disclosed in e.g., WO 00/58293 A1;

(t) protein tyrosine phosphatase-1B (PTP-1B) inhibitors, (u) glucagon receptor antagonists,
(v) anti-obesity agents such as fenfluramine, dexfenfluramine, phentiramine, sibutramine, orlistat, neuropeptide Y1 or Y5 antagonists, neuropeptide Y2 agonists, MC4R (melanocortin 4 receptor) agonists, cannabinoid receptor 1 (CB-1) antagonists/inverse agonists, and β3 adrenergic receptor agonists (e.g., GW-320659), nerve growth factor agonist (e.g., axokine), growth hormone agonists (e.g., AOD-9604), 5-LIT (serotonin) reuptake/transporter inhibitors (e.g., Prozac), DA (dopamine) reuptake inhibitors (e.g., Buproprion), 5-HT, NA and DA reuptake blockers, steroidal plant extracts (e.g., P57), CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g., SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-2 (acetyl-CoA carboxylase-1) inhibitors, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, Topiramate, glucocorticoid antagonist, Exendin-4 agonists, 5-HT$_{2C}$ (serotonin receptor 2C) agonists (e.g., Lorcaserin), PDE (phosphodiesterase) inhibitors, fatty acid transporter inhibitors, dicarboxylate transporter inhibitors, glucose transporter inhibitors, (w) anti-inflammatory agents such as cyclooxygenase-2 (COX-2) inhibitors (e.g., rofecoxib and celecoxib); glucocorticoids, azulfidine, thrombin inhibitors (e.g., heparin, argatroban, melagatran, dabigatran) and platelet aggregation inhibitors (e.g., glycoprotein IIb/IIIa fibrinogen receptor antagonists or aspirin), and
(y) antihypertensives such as beta blockers (e.g., angiotensin II receptor antagonists such as losartan, eprosartan, irbesartan, tasosartan, telmisartan or valsartan; angiotensin converting enzyme inhibitors such as enalapril, captopril, cilazapril, ramapril, zofenopril, lisinopril and fosinopril; calcium channel blockers such as nifedipine and diltiazami and endothelian antagonists.

Such other pharmaceutically active compounds may be administered in an amount commonly used therefore, contemporaneously or sequentially with a compound of the formula I or a pharmaceutically acceptable salt thereof. In the treatment of patients who have type 2 diabetes, insulin resistance, obesity, metabolic syndrome, neurological disorders, and co-morbidities that accompany these diseases, more than one pharmaceutically active compound is commonly administered. The compounds of formula I of this invention may generally be administered to a patient who is already taking one or more other drugs for these conditions. When a compound of formula I is used contemporaneously with one or more other pharmaceutically active compounds, a pharmaceutical composition in an unit dosage form containing such other pharmaceutically active compounds and the compound of the formula I is preferred. Thus, the invention also relates to a pharmaceutical composition containing a compound of formula I in combination with one or more other pharmaceutically active compounds as defined above. When used in combination with one or more other active ingredients, the compound of formula I of the present invention and the other pharmaceutically active compounds may be used in lower doses than when each is used singly. These kinds of pharmaceutical compositions are also included in the invention.

However, the combination therapy also includes therapies in which the compound of formula I and one or more other pharmaceutically active compounds are administered in different dosage forms, but with overlapping schedules. The invention thus also relates to a method for the treatment a of diseases which are associated with the modulation of GPBAR1 activity, which method comprises administering a therapeutically active amount of a compound of formula I in combination with one or more other pharmaceutically active compounds to a human being or animal.

The following test was carried out in order to determine the activity of the compounds of formula I:

The cDNA of the human GPBAR1 receptor (Genbank: NM_170699 with the exception of a silent C:G mutation at position 339 from the start codon) was amplified by polymerase chain reaction (PCR) from human cDNA and inserted into pCineo (Promega) by standard methods (Current Protocols in Molecular Biology, Wiley Press, ed. Ausubel et al.). The final clone was verified by DNA sequence analysis. The plasmid was transfected into CHO cells deficient in dihydrofolate reductase activity (CHO-dhfr-) using Lipofectamine plus (Invitrogen). Clones were isolated in limited dilution conditions and identified by activities in the cAMP assay using lithocholic acid as agonist. A clonal cell line displaying the greatest activity in cAMP increases was selected and identified as giving consistently good responses for up to at least 20 passages.

cAMP Assay

CHO-dhfr(minus) cells expressing human GPBAR1 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 mM. Compounds were added to a final assay volume of 100 μl and incubated for 30 min at 30° C. The assay was stopped by the addition of 50 μl lysis reagent (Tris, NaCl, 1.5% Triton X100, 2.5% NP40, 10% $NaN_3$) and 50 μl detection solutions (20 μM mAb Alexa700-cAMP 1:1, and 48 μM Ruthenium-2-AHA-cAMP) and shaked for 2 h at room temperature. The time-resolved energy transfer is measured by a TRF reader (Evotec Technologies GmbH, Hamburg Germany), equipped with a ND:YAG laser as excitation source. The plate is measured twice with the excitation at 355 nm and at the emission with a delay of 100 ns and a gate of 100 ns, total exposure time 10s at 730 (bandwith 30 nm) or 645 nm (bandwith 75 nm), respectively. The measured signal at 730 nm has to be corrected for the ruthenium background, the direct excitation of Alexa and the buffer control. The FRET signal is calculated as follows: FRET=T730-Alexa730-P (T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

$EC_{50}$ values were determined using Activity Base analysis (ID Business Solution, Limited). The $EC_{50}$ values for a wide range of bile acids generated from this assay were in agreement with the values published in the scientific literature. Specificity for GPBAR1 was tested in non-transfected CHO cells in the same assay as above.

The compounds according to formula I have an activity in the above assay ($EC_{50}$) preferably of 0.5 nM to 10 μM, more preferably of 0.5 nM to 2 μM, more preferably of 0.5 nM to 1 μM and most preferably of 0.5 nM to 100 nM.

For example, the following compounds showed the following human $EC_{50}$ values in the functional cAMP assay described above:

| Example | human $EC_{50}$ [μM] |
|---|---|
| 1 | 0.396 |
| 2 | 0.989 |
| 3 | 0.192 |
| 4 | 1.398 |
| 5 | 0.649 |
| 6 | 0.996 |
| 7 | 0.575 |
| 8 | 0.644 |
| 9 | 1.014 |
| 10 | 0.053 |
| 11 | 0.153 |
| 12 | 1.152 |
| 13 | 0.149 |
| 14 | 0.236 |
| 15 | 1.692 |
| 16 | 1.923 |
| 17 | 0.176 |
| 18 | 0.322 |
| 19 | 0.625 |
| 20 | 0.473 |
| 21 | 0.345 |
| 22 | 0.651 |
| 23 | 0.232 |
| 24 | 0.010 |
| 25 | 0.128 |
| 26 | 0.106 |
| 27 | 0.145 |
| 28 | 1.976 |
| 29 | 0.144 |
| 30 | 0.436 |
| 31 | 0.138 |
| 32 | 0.070 |
| 33 | 0.203 |
| 34 | 0.058 |
| 35 | 0.283 |
| 36 | 0.135 |
| 37 | 0.028 |
| 38 | 0.057 |
| 39 | 0.029 |
| 40 | 0.103 |
| 41 | 0.033 |
| 42 | 0.020 |
| 43 | 0.496 |
| 44 | 0.044 |
| 45 | 0.092 |
| 46 | 0.905 |
| 47 | 1.247 |
| 48 | 0.066 |
| 49 | 0.173 |
| 50 | 0.631 |
| 51 | 0.059 |
| 52 | 0.116 |
| 53 | 0.321 |
| 54 | 0.035 |
| 55 | 0.641 |
| 56 | 1.393 |
| 57 | 0.385 |
| 58 | 0.758 |
| 59 | 1.554 |
| 60 | 1.551 |
| 61 | 1.979 |
| 62 | 0.820 |
| 63 | 0.170 |
| 64 | 0.155 |
| 65 | 0.357 |
| 66 | 0.518 |
| 67 | 1.691 |

-continued

| Example | human $EC_{50}$ [μM] |
|---|---|
| 68 | 0.837 |
| 69 | 0.566 |
| 70 | 0.561 |
| 71 | 0.436 |
| 72 | 0.163 |
| 73 | 0.418 |
| 74 | 1.532 |
| 75 | 1.577 |
| 76 | 1.956 |
| 77 | 0.765 |
| 78 | 0.128 |
| 79 | 0.127 |
| 80 | 0.630 |
| 81 | 0.078 |
| 82 | 1.267 |
| 83 | 0.013 |
| 84 | 0.686 |
| 85 | 0.231 |
| 86 | 0.096 |
| 87 | 0.075 |
| 88 | 0.950 |
| 89 | 0.007 |
| 90 | 0.019 |
| 91 | 0.015 |
| 92 | 0.007 |
| 93 | 0.057 |
| 94 | 0.157 |
| 95 | 0.028 |
| 96 | 0.328 |
| 97 | 0.028 |
| 98 | 0.217 |
| 99 | 0.388 |
| 100 | 1.055 |
| 101 | 0.150 |
| 102 | 0.703 |
| 103 | 0.299 |
| 104 | 0.173 |
| 105 | 0.138 |
| 106 | 0.425 |
| 107 | 0.662 |
| 108 | 0.122 |
| 109 | 0.562 |
| 110 | 0.029 |
| 111 | 0.102 |
| 112 | 1.714 |
| 113 | 0.149 |
| 114 | 0.946 |
| 115 | 0.920 |
| 116 | 1.160 |
| 117 | 0.572 |
| 118 | 0.771 |
| 119 | 0.165 |
| 120 | 1.654 |
| 121 | 0.231 |
| 122 | 0.062 |
| 123 | 0.002 |
| 124 | 0.607 |
| 125 | 0.004 |
| 126 | 0.010 |
| 127 | 0.014 |
| 128 | 0.918 |
| 129 | 0.024 |
| 130 | 1.829 |
| 131 | 0.321 |
| 132 | 0.066 |
| 133 | 1.974 |
| 134 | 1.652 |
| 135 | 0.473 |
| 136 | 0.246 |
| 137 | 0.201 |
| 138 | 0.035 |
| 139 | 0.926 |
| 140 | 0.259 |
| 141 | 0.324 |
| 142 | 0.307 |
| 143 | 0.745 |
| 144 | 0.286 |

-continued

| Example | human EC$_{50}$ [μM] |
|---|---|
| 145 | 0.029 |
| 146 | 1.967 |
| 147 | 0.015 |
| 148 | 1.964 |
| 149 | 0.155 |
| 150 | 0.058 |
| 151 | 1.071 |
| 152 | 0.689 |
| 153 | 0.565 |
| 154 | 0.053 |
| 155 | 0.788 |
| 156 | 0.841 |
| 157 | 1.676 |
| 158 | 0.384 |
| 159 | 0.395 |
| 160 | 0.724 |
| 161 | 0.104 |
| 162 | 1.164 |
| 163 | 0.054 |
| 164 | 0.036 |
| 165 | 0.340 |
| 166 | 0.148 |
| 167 | 0.211 |
| 168 | 1.436 |
| 169 | 0.127 |
| 170 | 0.069 |
| 171 | 0.102 |
| 172 | 0.132 |
| 173 | 0.047 |
| 174 | 0.029 |
| 175 | 0.843 |
| 176 | 0.114 |
| 177 | 0.063 |
| 178 | 0.096 |
| 179 | 0.041 |
| 180 | 0.071 |
| 181 | 0.091 |
| 182 | 0.181 |
| 183 | 0.341 |
| 184 | 0.022 |
| 185 | 0.092 |

The compounds of formula I and their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

Abbreviations

CAS RN=chemical abstracts registration number, Celite®=filtration aid, DMAc=dimethylacetamide, DMAP=4-dimethylaminopyridine, DMF=N,N-dimethylformamide, DMSO=dimethyl sulfoxide, EI=electron impact, h=hour, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, ISP=ion spray positive (mode), ISN=ion spray negative (mode), min=minutes, LiOH=lithium hydroxide, MgSO$_4$=magnesium sulfate, MPLC=medium performance liquid chromatography, MS=mass spectrum, NaHCO$_3$=sodium hydrogen carbonate, NaOH=sodium hydroxide, Na$_2$SO$_4$=sodium sulfate, NH$_4$Cl=ammonium chloride, NMR=nuclear magnetic resonance, KOH=potassium hydroxide, P=protecting group, R=any group, rt=room temperature, SiO$_2$=silica gel, THF=tetrahydrofuran, X=halogen.

Example 1

(3,4-Dihydro-2H-quinolin-1-yl)-[2-(3-trifluoromethyl-phenoxy)-pyridin-3-yl]-methanone

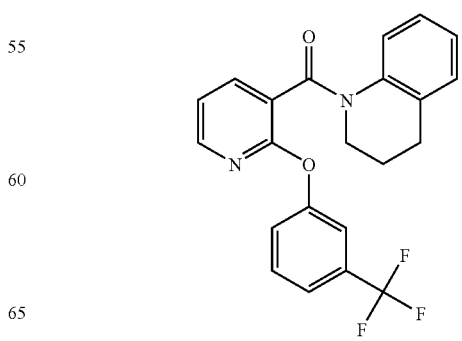

Step 1: 2-(3-Trifluoromethyl-phenoxy)-nicotinic acid

To a solution of 2-chloro-nicotinic acid (1.0 g, 6.35 mmol, 1.0 equiv; [CAS RN 2942-59-8]) and 3-trifluoromethyl-phenol (1.03 g, 6.35 mmol, 1.0 equiv; [CAS RN 98-17-9]) in anhydrous DMF (5 mL) was added potassium carbonate (1.75 g, 12.69 mmol, 2.0 equiv; [CAS RN 584-08-7]), copper (I) iodide (0.12 g, 0.64 mmol, 0.1 equiv; [CAS RN 7681-65-4]) and copper(0) nanopowder with an averaged particle size of 100 nm (0.12 g, 1.90 mmol, 0.3 equiv; [CAS RN 7440-50-8]). The reaction mixture was heated by microwave irradiation to 140° C. for 30 min. The solvent was evaporated under reduced pressure and the crude reaction product taken up in water (25 mL) and filtered. The solution was adjusted to pH 4 by addition of acetic acid and the formed white precipitate filtered, washed with little cold water and dried under high vacuum providing 0.53 g (28%) of the title compound. $^1$H NMR (300 MHz, DMSO): δ7.26-7.30 (m, 1H), 7.43-7.50 (m, 2H), 7.57-7.66 (m, 2H), 8.26-8.29 (m, 2H). $^{19}$F NMR (282 MHz, DMSO): δ−61.0. MS (ISN): 282.1 [M−H]$^-$.

Step 2

To a solution of 2-(3-trifluoromethyl-phenoxy)-nicotinic acid (200 mg, 0.71 mmol, 1.0 equiv) in anhydrous DMF (3 mL) was added 1,2,3,4-tetrahydro-quinoline (113 mg, 107 µL, 0.85 mmol, 1.2 equiv; [CAS RN 635-46-1]), N-ethyldiisopropylamine (457 mg, 617 µL, 3.53 mmol, 5.0 equiv; [CAS RN 7087-68-5]) and HATU (322 mg, 0.85 mmol, 1.2 equiv; [CAS RN 148893-10-1]). The reaction mixture was heated by microwave irradiation to 100° C. for 5 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 157 mg (56%) of the title compound. MS (ISP): 399.2 [M+H]$^+$.

Example 2

[2-(2-Chloro-phenoxy)-pyridin-3-yl]-(3,4-dihydro-2H-quinolin-1-yl)-methanone

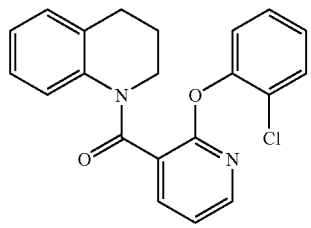

Step 1: 2-(2-Chloro-phenoxy)-nicotinic acid 2-(2-Chloro-phenoxy)-nicotinic acid was prepared in analogy to Example 1, Step 1, replacing 3-trifluoromethyl-phenol with 2-chloro-phenol ([CAS RN 95-57-8]). MS (ISN): 248.1 [M−H]$^-$.

Step 2

The title compound was prepared in analogy to Example 1, Step 2, replacing 2-(3-trifluoromethyl-phenoxy)-nicotinic acid with 2-(2-chloro-phenoxy)-nicotinic acid. MS (ISP): 365.1 [M+H]$^+$.

Example 3

[2-(3-Chloro-phenoxy)-pyridin-3-yl]-(3,4-dihydro-2H-quinolin-1-yl)-methanone

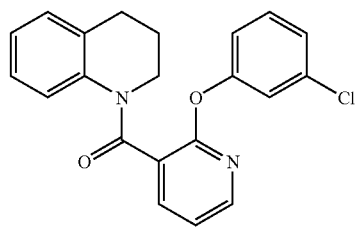

Step 1: 2-(3-Chloro-phenoxy)-nicotinic acid 2-(3-Chloro-phenoxy)-nicotinic acid was prepared in analogy to Example 1, Step 1, replacing 3-trifluoromethyl-phenol with 3-chloro-phenol ([CAS RN 108-43-0]). $^1$H NMR (300 MHz, DMSO): δ7.11 (d, J=9.0 Hz, 1H), 7.25-7.30 (m, 3H), 7.44 (t, J=7.5 Hz, 1H), 8.29-8.31 (m, 1H), 13.28 (br s, 1H). MS (ISN): 248.1 [M−H]$^-$.

Step 2

The title compound was prepared in analogy to Example 1, Step 2, replacing 2-(3-trifluoromethyl-phenoxy)-nicotinic acid with 2-(3-chloro-phenoxy)-nicotinic acid. MS (ISP): 365.1 [M+H]$^+$.

Example 4

(6-Methyl-3,4-dihydro-2H-quinolin-1-yl)-[2-(3-trifluoromethyl-phenoxy)-pyridin-3-yl]-methanone

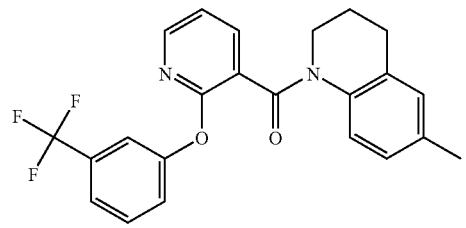

The title compound was prepared from 2-(3-trifluoromethyl-phenoxy)-nicotinic acid in analogy to Example 1, Step 2, by replacing 1,2,3,4-tetrahydro-quinoline with 6-methyl-1,2,3,4-tetrahydro-quinoline ([CAS RN 91-61-2]). MS (ISP): 413.2 [M+H]$^+$.

Example 5

[2-(3-Chloro-phenoxy)-pyridin-3-yl]-(6-methyl-3,4-dihydro-2H-quinolin-1-yl)-methanone

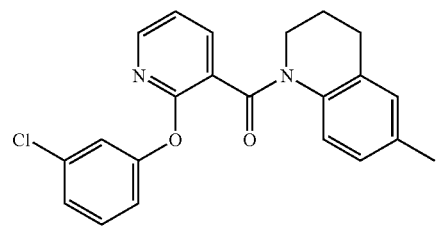

The title compound was prepared in analogy to Example 1, Step 2, replacing 2-(3-trifluoromethyl-phenoxy)-nicotinic acid with 2-(3-chloro-phenoxy)-nicotinic acid (Example 3, Step 1) and 1,2,3,4-tetrahydro-quinoline with 6-methyl-1,2,3,4-tetrahydro-quinoline ([CAS RN 91-61-2]). MS (ISP): 379.1 [M+H]+.

Example 6

[2-(3,4-Dichloro-phenoxy)-pyridin-3-yl]-(3,4-dihydro-2H-quinolin-1-yl)-methanone

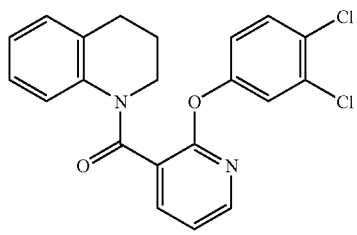

Step 1: (2-Chloro-pyridin-3-yl)-(3,4-dihydro-2H-quinolin-1-yl)-methanone

To a solution of 2-chloro-nicotinic acid (1.0 g, 6.35 mmol, 1.0 equiv; [CAS RN 2942-59-8]) in dichloromethane (40 mL) was added 1,2,3,4-tetrahydro-quinoline (0.93 g, 0.88 mL, 6.98 mmol, 1.1 equiv; [CAS RN 635-46-1]), triethylamine (1.28 g, 1.77 mL, 12.69 mmol, 2.0 equiv; [CAS RN 121-44-8]) and 2-chloro-1-methylpyridinium iodide (1.96 g, 6.98 mmol, 1.1 equiv; [CAS RN 14338-32-0]). The reaction mixture was stirred at rt for 2 h. To the residue was added a sat. solution of NaHCO$_3$ (100 mL) and the solution extracted with dichloromethane (3×50 mL). The combined organic phases were dried over Na$_2$SO$_4$ and the product purified by silica column chromatography using a MPLC system (CombiFlash Companion, Isco Inc.) eluting with a gradient of heptane/ethyl acetate affording 1.52 g (88%) of the title compound as a light yellow solid. $^1$H NMR (400 MHz, CDCl$_3$): δ2.07 (quint, J=6.6 Hz, 2H), 2.86 (t, J=6.6 Hz, 2H), 3.90 (t, J=6.4 Hz, 2H), 6.64 (br s, 1H), 6.93 (br t, J=4.0 Hz, 1H), 7.04 (br d, J=4.0 Hz, 1H), 7.08 (t, J=7.6 Hz, 1H), 7.19 (d, J=7.6 Hz, 1H), 7.30 (s, 1H), 8.31 (d, J=7.6 Hz, 1H). MS (ISP): 273.1 [M+H]+.

Step 2

To a solution of (2-chloro-pyridin-3-yl)-(3,4-dihydro-2H-quinolin-1-yl)-methanone (50 mg, 0.18 mmol, 1.0 equiv) and 3,4-dichloro-phenol (29.9 mg, 0.18 mmol, 1.0 equiv; [CAS RN 95-77-2]) in anhydrous DMF (1 mL) was added potassium carbonate (50.7 mg, 0.37 mmol, 2.0 equiv; [CAS RN 584-08-7]), copper(I) iodide (3.5 mg, 0.018 mmol, 0.1 equiv; [CAS RN 7681-65-4]) and copper(0) nanopowder with an averaged particle size of 100 nm (3.5 mg, 0.055 mmol, 0.3 equiv; [CAS RN 7440-50-8]). The reaction mixture was heated by microwave irradiation to 200° C. for 30 min. Purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 2.2 mg (3%) of the title compound. MS (ISP): 399.2 [M+H]+.

Example 7

3-[3-(3,4-Dihydro-2H-quinoline-1-carbonyl)-pyridin-2-yloxy]-benzonitrile

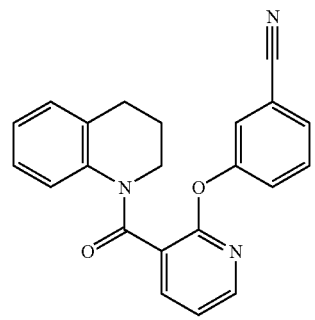

The title compound was prepared in analogy to Example 6, Step 2, replacing 3,4-dichloro-phenol with 3-hydroxy-benzonitrile ([CAS RN 873-62-1]). MS (ISP): 356.1 [M+H]+.

Example 8

(3,4-Dihydro-2H-quinolin-1-yl)-(2-m-tolyloxy-pyridin-3-yl)-methanone

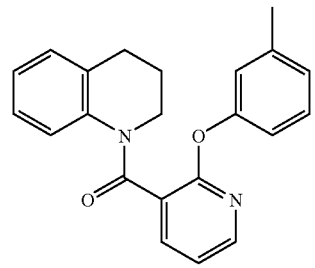

The title compound was prepared in analogy to Example 6, Step 2, replacing 3,4-dichloro-phenol with 3-methyl-phenol ([CAS RN 108-39-4]). MS (ISP): 345.4 [M+H]+.

Example 9

[2-(3-Chloro-4-methyl-phenoxy)-pyridin-3-yl]-(3,4-dihydro-2H-quinolin-1-yl)-methanone

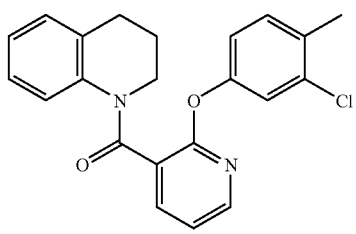

The title compound was prepared in analogy to Example 6, Step 2, replacing 3,4-dichloro-phenol with 3-chloro-4-methyl-phenol ([CAS RN 615-62-3]). MS (ISP): 379.3 [M+H]+.

Example 10

[2-(3-Chloro-4-fluoro-phenoxy)-pyridin-3-yl]-(3,4-dihydro-2H-quinolin-1-yl)-methanone

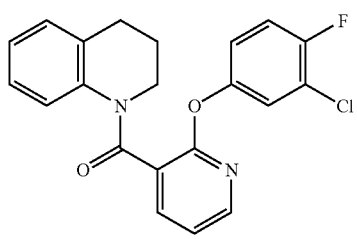

The title compound was prepared in analogy to Example 6, Step 2, replacing 3,4-dichloro-phenol with 3-chloro-4-fluoro-phenol ([CAS RN 2613-23-2]). MS (ISP): 383.3 [M+H]+.

Example 11

[2-(5-Chloro-2-methyl-phenoxy)-pyridin-3-yl]-(3,4-dihydro-2H-quinolin-1-yl)-methanone

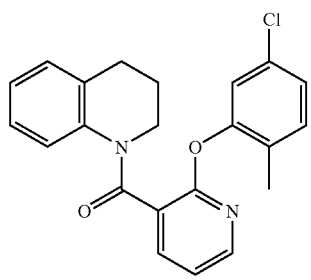

The title compound was prepared in analogy to Example 6, Step 2, replacing 3,4-dichloro-phenol with 5-chloro-2-methyl-phenol ([CAS RN 5306-98-9]). MS (ISP): 379.3 [M+H]+.

Example 12

[2-(2,3-Dichloro-phenoxy)-pyridin-3-yl]-(3,4-dihydro-2H-quinolin-1-yl)-methanone

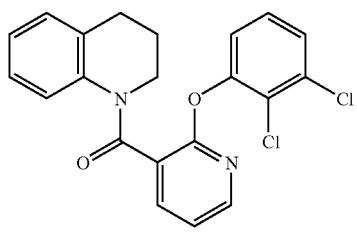

The title compound was prepared in analogy to Example 6, Step 2, replacing 3,4-dichloro-phenol with 2,3-dichloro-phenol ([CAS RN 576-24-9]). MS (ISP): 399.2 [M+H]+.

Example 13

[2-(3-Chloro-5-fluoro-phenoxy)-pyridin-3-yl]-(3,4-dihydro-2H-quinolin-1-yl)-methanone

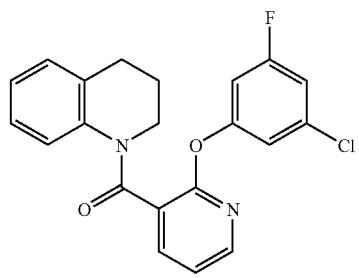

The title compound was prepared in analogy to Example 6, Step 2, replacing 3,4-dichloro-phenol with 3-chloro-5-fluoro-phenol ([CAS RN 202982-70-5]). MS (ISP): 383.3 [M+H]+.

Example 14

(3,4-Dihydro-2H-quinolin-1-yl)-[2-(2,4,5-trichloro-phenoxy)-pyridin-3-yl]-methanone

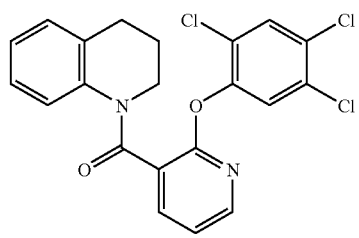

The title compound was prepared in analogy to Example 6, Step 2, replacing 3,4-dichloro-phenol with 2,4,5-trichloro-phenol ([CAS RN 95-95-4]). MS (ISP): 435.1 [M+H]+.

Example 15

[2-(3-Benzoyl-phenoxy)-pyridin-3-yl]-(3,4-dihydro-2H-quinolin-1-yl)-methanone

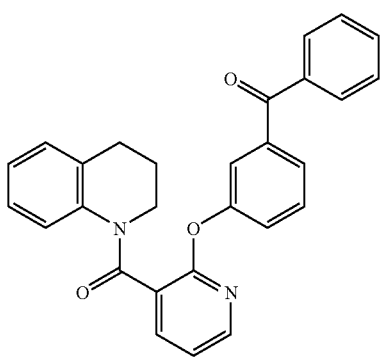

The title compound was prepared in analogy to Example 6, Step 2, replacing 3,4-dichloro-phenol with (3-hydroxy-phenyl)-phenyl-methanone ([CAS RN 13020-57-0]). MS (ISP): 435.2 [M+H]+.

Example 16

(3,4-Dihydro-2H-quinolin-1-yl)-[2-(3-trifluoromethoxy-phenoxy)-pyridin-3-yl]-methanone

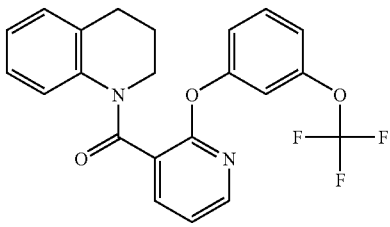

The title compound was prepared in analogy to Example 6, Step 2, replacing 3,4-dichloro-phenol with 3-trifluoromethoxy-phenol ([CAS RN 827-99-6]). MS (ISP): 415.3 [M+H]+.

Example 17

[2-(3,5-Dichloro-phenoxy)-pyridin-3-yl]-(3,4-dihydro-2H-quinolin-1-yl)-methanone

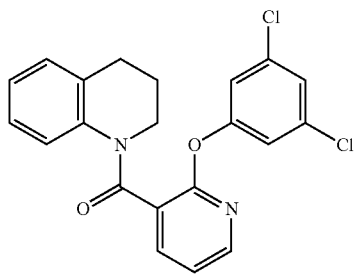

The title compound was prepared in analogy to Example 6, Step 2, replacing 3,4-dichloro-phenol with 3,5-dichloro-phenol ([CAS RN 591-35-5]). MS (ISP): 399.2 [M+H]+.

Example 18

(3,4-Dihydro-2H-quinolin-1-yl)-[2-(3-fluoro-phenoxy)-pyridin-3-yl]-methanone

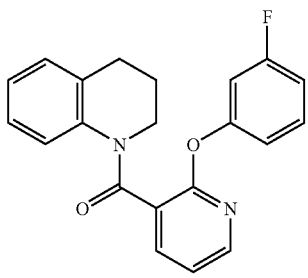

The title compound was prepared in analogy to Example 6, Step 2, replacing 3,4-dichloro-phenol with 3-fluoro-phenol ([CAS RN 372-20-3]). MS (ISP): 349.3 [M+H]+.

Example 19

(3,4-Dihydro-2H-quinolin-1-yl)-[2-(3-isopropyl-phenoxy)-pyridin-3-yl]-methanone

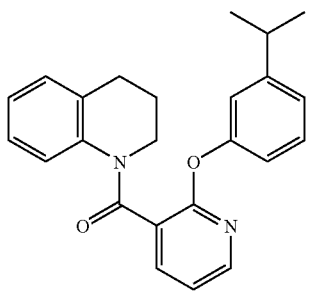

The title compound was prepared in analogy to Example 6, Step 2, replacing 3,4-dichloro-phenol with 3-isopropyl-phenol ([CAS RN 618-45-1]). MS (ISP): 373.4 [M+H]+.

Example 20

(3,4-Dihydro-2H-quinolin-1-yl)-[2-(3-ethyl-phenoxy)-pyridin-3-yl]-methanone

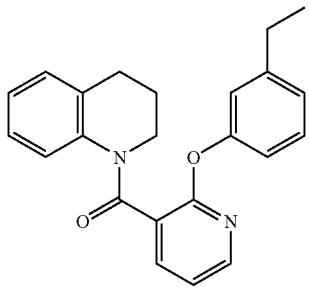

The title compound was prepared in analogy to Example 6, Step 2, replacing 3,4-dichloro-phenol with 3-ethyl-phenol ([CAS RN 620-17-7]). MS (ISP): 359.2 [M+H]+.

Example 21

(3,4-Dihydro-2H-quinolin-1-yl)-[2-(3-iodo-phenoxy)-pyridin-3-yl]-methanone

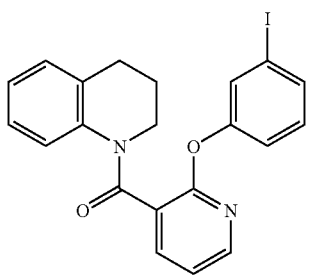

The title compound was prepared in analogy to Example 6, Step 2, replacing 3,4-dichloro-phenol with 3-iodo-phenol ([CAS RN 626-02-02-8]). MS (ISP): 457.1 [M+H]⁺.

Example 22

[2-(3-Chloro-2-fluoro-5-trifluoromethyl-phenoxy)-pyridin-3-yl]-(3,4-dihydro-2H-quinolin-1-yl)-methanone

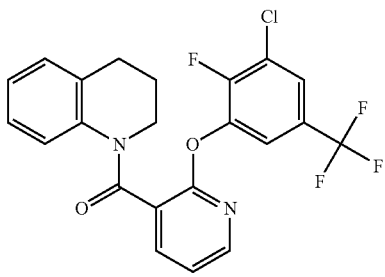

The title compound was prepared in analogy to Example 6, Step 2, replacing 3,4-dichloro-phenol with 3-chloro-2-fluoro-5-trifluoromethyl-phenol ([CAS RN 261763-12-6]). MS (ISP): 451.2 [M+H]⁺.

Example 23

[2-(3-Bromo-phenoxy)-pyridin-3-yl]-(3,4-dihydro-2H-quinolin-1-yl)-methanone

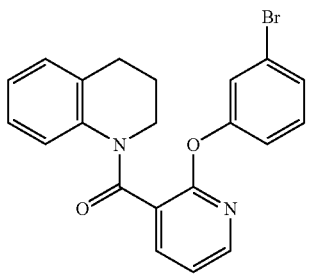

The title compound was prepared in analogy to Example 6, Step 2, replacing 3,4-dichloro-phenol with 3-bromo-phenol ([CAS RN 591-20-8]). MS (ISP): 409.2 [M+H]⁺.

Example 24

[2-(2,5-Dichloro-phenoxy)-pyridin-3-yl]-(3,4-dihydro-2H-quinolin-1-yl)-methanone

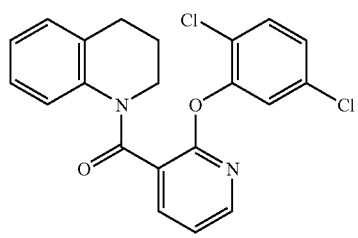

The title compound was prepared in analogy to Example 6, Step 2, replacing 3,4-dichloro-phenol with 2,5-dichloro-phenol ([CAS RN 583-78-8]). MS (ISP): 399.2 [M+H]⁺.

Example 25

[2-(3-Chloro-phenoxy)-5-fluoro-pyridin-3-yl]-(3,4-dihydro-2H-quinolin-1-yl)-methanone

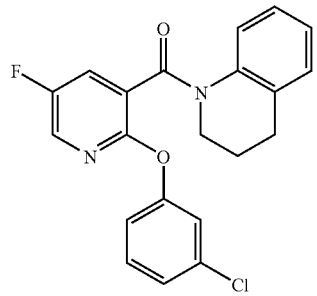

Step 1: (2-Chloro-5-fluoro-pyridin-3-yl)-(3,4-dihydro-2H-quinolin-1-yl)-methanone To a solution of 2-chloro-5-fluoro-nicotinic acid (0.60 g, 3.42 mmol, 1.0 equiv; [CAS RN 38186-88-8]) in anhydrous DMF (5 mL) was added 1,2,3,4-tetrahydro-quinoline (0.55 g, 0.52 mL, 4.10 mmol, 1.2 equiv; [CAS RN 635-46-1]), N-ethyldiisopropylamine (2.21 g, 2.91 mL, 17.09 mmol, 5.0 equiv; [CAS RN 7087-68-5]) and HATU (1.56 g, 4.10 mmol, 1.2 equiv; [CAS RN 148893-10-1]). The reaction mixture was heated by microwave irradiation to 100° C. for 10 min. To the residue was added a sat. solution of NaHCO₃ (50 mL) and the solution extracted with ethyl acetate (3×50 mL). The combined organic phases were dried over Na₂SO₄ and the product purified by silica column chromatography using a MPLC system (CombiFlash Companion, Isco Inc.) eluting with a gradient of heptane/ethyl acetate affording 0.51 g (52%) of the title compound as a light yellow solid. MS (ISP): 291.1 [M+H]⁺.

Step 2

To a solution of (2-chloro-5-fluoro-pyridin-3-yl)-(3,4-dihydro-2H-quinolin-1-yl)-methanone (53.2 mg, 0.18 mmol, 1.0 equiv) and 3-chloro-phenol (23.5 mg, 0.18 mmol, 1.0 equiv; [CAS RN 108-43-0]) in acetonitrile (1 mL) was added potassium carbonate (50.7 mg, 0.37 mmol, 2.0 equiv; [CAS RN 584-08-7]), copper(I) iodide (3.5 mg, 0.018 mmol, 0.1 equiv; [CAS RN 7681-65-4]) and copper(0) nanopowder with an averaged particle size of 100 nm (3.5 mg, 0.055 mmol, 0.3 equiv; [CAS RN 7440-50-8]). The reaction mixture was heated by microwave irradiation to 200° C. for 90 min. Removal of the solvent under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 4.3 mg (6%) of the title compound. MS (ISP): 383.2 [M+H]+.

Example 26

[2-(2,5-Difluoro-phenoxy)-5-fluoro-pyridin-3-yl]-(3,4-dihydro-2H-quinolin-1-yl)-methanone

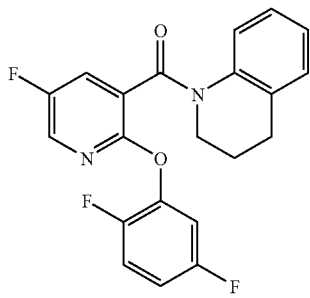

The title compound was prepared in analogy to Example 25, Step 2, replacing 3-chloro-phenol with 2,5-difluoro-phenol ([CAS RN 2713-31-7]). MS (ISP): 385.3 [M+H]+.

Example 27

[5-Chloro-2-(2,5-dichloro-phenoxy)-pyridin-3-yl]-(3,4-dihydro-2H-quinolin-1-yl)-methanone

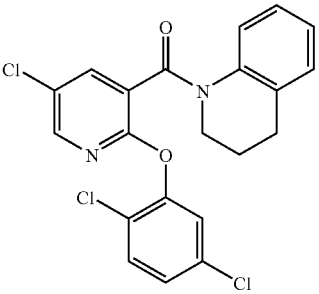

Step 1: (2,5-Dichloro-pyridin-3-yl)-(3,4-dihydro-2H-quinolin-1-yl)-methanone (2,5-Dichloro-pyridin-3-yl)-(3,4-dihydro-2H-quinolin-1-yl)-methanone was prepared in analogy to Example 25, Step 1, replacing 2-chloro-5-fluoro-nicotinic acid with 2,5-dichloro-nicotinic acid ([CAS RN 59782-85-3]). MS (ISP): 307.2 [M+H]+.

Step 2

The title compound was prepared in analogy to Example 25, Step 2, replacing (2-chloro-5-fluoro-pyridin-3-yl)-(3,4-dihydro-2H-quinolin-1-yl)-methanon with (2,5-dichloro-pyridin-3-yl)-(3,4-dihydro-2H-quinolin-1-yl)-methanone and 3-chloro-phenol with 2,5-dichloro-phenol ([CAS RN 583-78-8]). MS (ISP): 433.2 [M+H]+.

Example 28

[5-Chloro-2-(2,5-difluoro-phenoxy)-pyridin-3-yl]-(3,4-dihydro-2H-quinolin-1-yl)-methanone

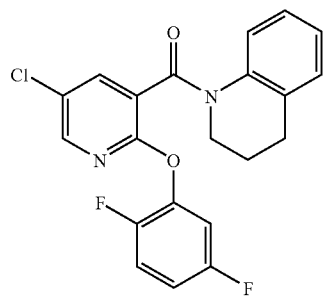

The title compound was prepared in analogy to Example 27, Step 2, replacing 2,5-dichloro-phenol with 2,5-difluoro-phenol ([CAS RN 2713-31-7]). MS (ISP): 401.3 [M+H]+.

Example 29

[2-(2,5-Dichloro-phenoxy)-6-trifluoromethyl-pyridin-3-yl]-(3,4-dihydro-2H-quinolin-1-yl)-methanone

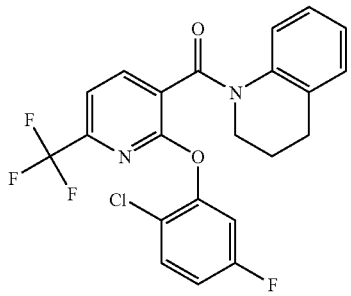

Step 1: (2-Chloro-6-trifluoromethyl-pyridin-3-yl)-(3,4-dihydro-2H-quinolin-1-yl)-methanone (2-Chloro-6-trifluoromethyl-pyridin-3-yl)-(3,4-dihydro-2H-quinolin-1-yl)-methanone was prepared in analogy to Example 25, Step 1, replacing 2-chloro-5-fluoro-nicotinic acid with 2-chloro-6-trifluoromethyl-nicotinic acid ([CAS RN 280566-45-2]). MS (ISP): 341.1 [M+H]+.

Step 2

The title compound was prepared in analogy to Example 25, Step 2, replacing (2-chloro-5-fluoro-pyridin-3-yl)-(3,4-dihydro-2H-quinolin-1-yl)-methanone with (2-chloro-6-trifluoromethyl-pyridin-3-yl)-(3,4-dihydro-2H-quinolin-1-yl)- methanone and 3-chloro-phenol with 2,5-dichloro-phenol ([CAS RN 583-78-8]). MS (ISP): 467.1 [M+H]+.

Example 30

[2-(3-Chloro-phenoxy)-pyridin-3-yl]-(2,3-dihydro-benzo[1,4]oxazin-4-yl)-methanone

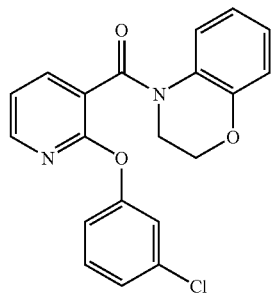

The title compound was prepared in analogy to Example 3, Step 2, replacing 1,2,3,4-tetrahydro-quinoline with 3,4-dihydro-2H-benzo[1,4]oxazine ([CAS RN 5735-53-5]). MS (ISP): 367.2 [M+H]+.

Example 31

[2-(2,5-Dichloro-phenoxy)-pyridin-3-yl]-(6-methyl-3,4-dihydro-2H-quinolin-1-yl)-methanone

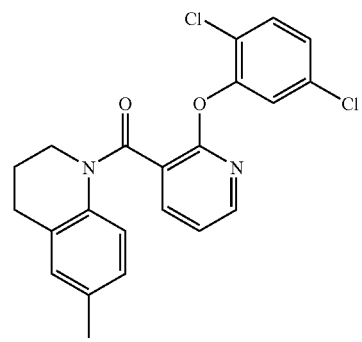

Step 1: 2-(2,5-Dichloro-phenoxy)-nicotinic acid 2-(2,5-Dichloro-phenoxy)-nicotinic acid was prepared in analogy to Example 1, Step 1, replacing 3-trifluoromethyl-phenol with 2,5-dichloro-phenol ([CAS RN 583-78-8]). MS (ISP): 284.0 [M+H]+.

Step 2

To a solution of 2-(2,5-dichloro-phenoxy)-nicotinic acid (42.6 mg, 0.15 mmol, 1.0 equiv) in anhydrous DMF (1 mL) was added 6-methyl-1,2,3,4-tetrahydro-quinoline (26.5 mg, 0.18 mmol, 1.2 equiv; [CAS RN 91-61-2]), N-ethyldiisopropylamine (97.0 mg, 131 µL, 0.75 mmol, 5.0 equiv; [CAS RN 7087-68-5]) and HATU (68.4 mg, 0.18 mmol, 1.2 equiv; [CAS RN 148893-10-1]). The reaction mixture was heated by microwave irradiation to 100° C. for 10 min. Removal of the solvent mixture under reduced pressure and purification by preparative (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) on reversed phase eluting with a gradient of acetonitrile/water provided 30 mg (49%) of the title compound. MS (ISP): 413.2 [M+H]+.

Example 32

2-(2,5-Dichloro-phenoxy)-N-ethyl-N-phenyl-nicotinamide

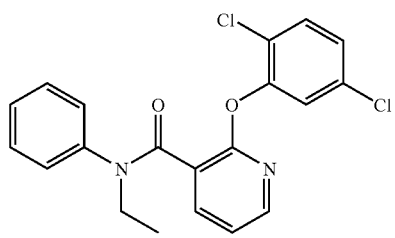

The title compound was prepared in analogy to Example 31, Step 2, replacing 6-methyl-1,2,3,4-tetrahydro-quinoline with ethyl-phenyl-amine ([CAS RN 103-69-5]). MS (ISP): 387.2 [M+H]+.

Example 33

(7-Chloro-3,4-dihydro-2H-quinolin-1-yl)-[2-(2,5-dichloro-phenoxy)-pyridin-3-yl]-methanone

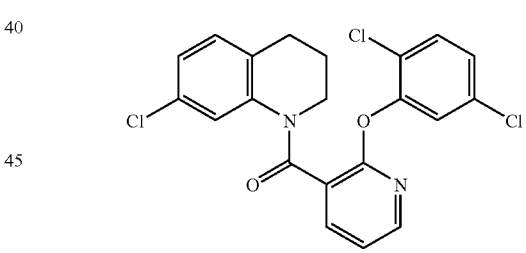

To a solution of 2-(2,5-dichloro-phenoxy)-nicotinic acid (42.6 mg, 0.15 mmol, 1.0 equiv; Example 31, Step 1) in anhydrous DMF (1.5 mL) was added 7-chloro-1,2,3,4-tetrahydro-quinoline hydrochloride (33.7 mg, 0.17 mmol, 1.1 equiv; [CAS RN 90562-34-8]), triethylamine (30.4 mg, 42 µL, 0.3 mmol, 2.0 equiv; [CAS RN 121-44-8]) and HATU (62.7 mg, 0.17 mmol, 1.1 equiv; [CAS RN 148893-10-1]). The reaction mixture was heated by microwave irradiation to 110° C. for 30 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 6 mg (10%) of the title compound. MS (ISP): 435.0 [M+H]+.

Example 34

[2-(2,5-Dichloro-phenoxy)-pyridin-3-yl]-(7-fluoro-3,4-dihydro-2H-quinolin-1-yl)-methanone

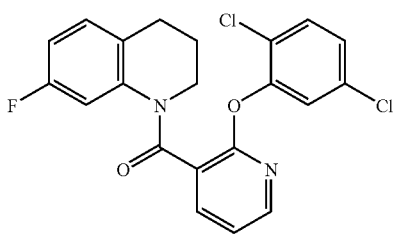

The title compound was prepared in analogy to Example 33 replacing 7-chloro-1,2,3,4-tetrahydro-quinoline hydrochloride with 7-fluoro-1,2,3,4-tetrahydro-quinoline hydrochloride (commercially available from Zannan Pharma Ltd). MS (ISP): 417.0 [M+H]+.

Example 35

2-(2,5-Dichloro-phenoxy)-N-methyl-N-phenyl-nicotinamide

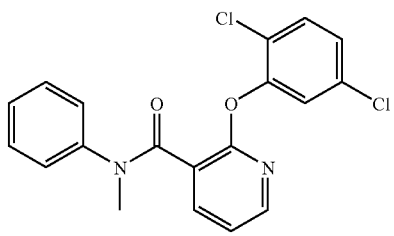

The title compound was prepared in analogy to Example 33 replacing 7-chloro-1,2,3,4-tetrahydro-quinoline hydrochloride with methyl-phenyl-amine ([CAS RN 100-61-8]). MS (ISP): 373.0 [M+H]+.

Example 36

[2-(2,5-Dichloro-phenoxy)-pyridin-3-yl]-(2,3-dihydro-benzo[1,4]oxazin-4-yl)-methanone

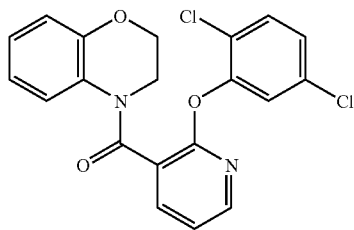

To a solution of 2-(2,5-dichloro-phenoxy)-nicotinic acid (42.6 mg, 0.15 mmol, 1.0 equiv; Example 31, Step 1) in dichloromethane (1.5 mL) was added 3,4-dihydro-2H-benzo[1,4]oxazine (22.9 mg, 0.17 mmol, 1.1 equiv; [CAS RN 5735-53-5]), triethylamine (30.4 mg, 42 μL, 0.3 mmol, 2.0 equiv; [CAS RN 121-44-8]) and 2-chloro-1-methylpyridinium iodide (42.2 mg, 0.17 mmol, 1.1 equiv; [CAS RN 14338-32-0]). The reaction mixture was stirred at rt over night. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 11 mg (18%) of the title compound. MS (ISP): 401.0 [M+H]+.

Example 37

[2-(2,5-Dichloro-phenoxy)-pyridin-3-yl]-(6-fluoro-3,4-dihydro-2H-quinolin-1-yl)-methanone

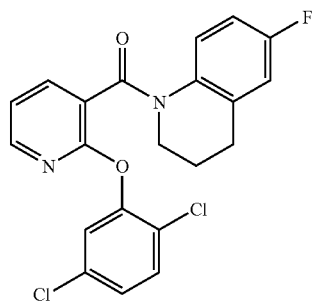

To a solution of 2-(2,5-dichloro-phenoxy)-nicotinic acid (59.7 mg, 0.21 mmol, 1.0 equiv; Example 31, Step 1) in dichloromethane (2 mL) was added 6-fluoro-1,2,3,4-tetrahydro-quinoline (34.9 mg, 0.23 mmol, 1.1 equiv; [CAS RN 59611-52-8]), triethylamine (42.5 mg, 59 μL, 0.42 mmol, 2.0 equiv; [CAS RN 121-44-8]) and 2-chloro-1-methylpyridinium iodide (59.0 mg, 0.23 mmol, 1.1 equiv; [CAS RN 14338-32-0]). The reaction mixture was stirred at 40° C. over night. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 27 mg (31%) of the title compound. MS (ISP): 417.4 [M+H]+.

Example 38

[2-(2,5-Dichloro-phenoxy)-pyridin-3-yl]-(6,7-difluoro-3,4-dihydro-2H-quinolin-1-yl)-methanone

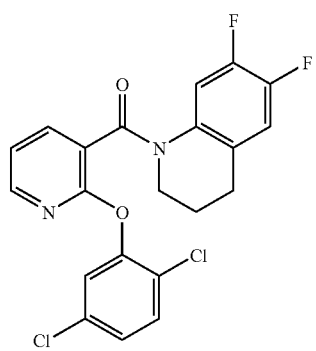

The title compound was prepared in analogy to Example 37 replacing 6-fluoro-1,2,3,4-tetrahydro-quinoline with 6,7-difluoro-1,2,3,4-tetrahydro-quinoline ([CAS RN 953717-64-1]). MS (ISP): 435.1 [M+H]+.

Example 39
[2-(2,5-Dichloro-phenoxy)-pyridin-3-yl]-(2,3-dihydro-benzo[1,4]thiazin-4-yl)-methanone

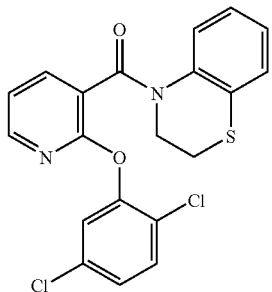

The title compound was prepared in analogy to Example 37 replacing 6-fluoro-1,2,3,4-tetrahydro-quinoline with 3,4-dihydro-2H-benzo[1,4]thiazine ([CAS RN 3080-99-7]). MS (ISP): 417.1 [M+H]+.

Example 40
N-(2-Chloro-phenyl)-2-(2,5-dichloro-phenoxy)-N-methyl-nicotinamide

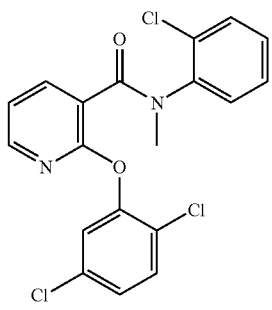

The title compound was prepared in analogy to Example 37 replacing 6-fluoro-1,2,3,4-tetrahydro-quinoline with (2-chloro-phenyl)-methyl-amine ([CAS RN 932-32-1]). MS (ISP): 407.1 [M+H]+.

Example 41
2-(2,5-Dichloro-phenoxy)-N-methyl-N-o-tolyl-nicotinamide

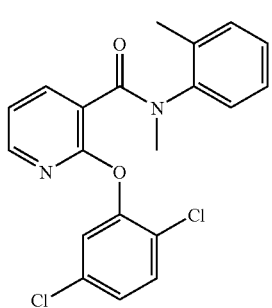

The title compound was prepared in analogy to Example 37 replacing 6-fluoro-1,2,3,4-tetrahydro-quinoline with methyl-o-tolyl-amine ([CAS RN 611-21-2]). MS (ISP): 387.1 [M+H]+.

Example 42
2-(2,5-Dichloro-phenoxy)-N-(2-methoxy-phenyl)-N-methyl-nicotinamide

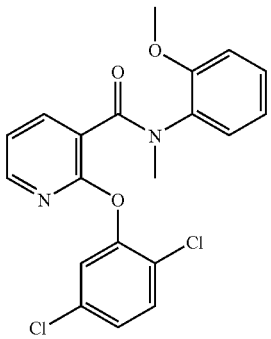

The title compound was prepared in analogy to Example 37 replacing 6-fluoro-1,2,3,4-tetrahydro-quinoline with (2-methoxy-phenyl)-methyl-amine ([CAS RN 10541-78-3]). MS (ISP): 403.1 [M+H]+.

Example 43
N-Biphenyl-2-yl-2-(2,5-dichloro-phenoxy)-N-methyl-nicotinamide

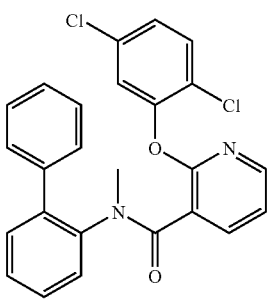

The title compound was prepared in analogy to Example 37 replacing 6-fluoro-1,2,3,4-tetrahydro-quinoline with biphenyl-2-yl-methyl-amine ([CAS RN 14925-09-8]). MS (ISP): 448.9 [M+H]+.

Example 44
[2-(2,5-Dichloro-phenoxy)-pyridin-3-yl]-(6,8-difluoro-3,4-dihydro-2H-quinolin-1-yl)-methanone

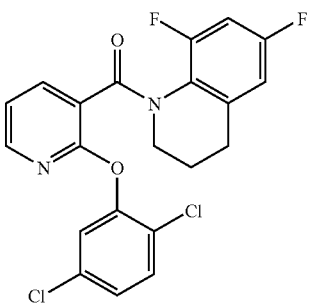

The title compound was prepared in analogy to Example 36 replacing 3,4-dihydro-2H-benzo[1,4]oxazine with 6,8-difluoro-1,2,3,4-tetrahydro-quinoline ([CAS RN 926218-72-6]). MS (ISP): 434.9 [M+H]⁺.

Example 45

2-(2,5-Dichloro-phenoxy)-N-(2-ethyl-phenyl)-N-methyl-nicotinamide

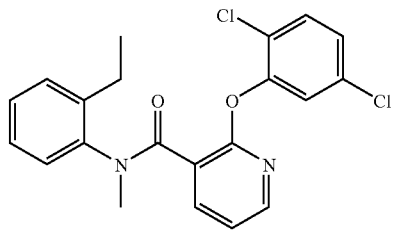

To a solution of 2-(2,5-dichloro-phenoxy)-nicotinic acid (59.7 mg, 0.21 mmol, 1.0 equiv; Example 31, Step 1) in dichloromethane (2.0 mL) was added 2-ethyl-phenylamine (27.9 mg, 0.23 mmol, 1.1 equiv; [CAS RN 578-54-1]), triethylamine (42.5 mg, 59 μL, 0.42 mmol, 2.0 equiv; [CAS RN 121-44-8]) and 2-chloro-1-methylpyridinium iodide (59.0 mg, 0.23 mmol, 1.1 equiv; [CAS RN 14338-32-0]) and the reaction mixture stirred at 40° C. over night. The solvent was removed by evaporation under reduced pressure and the crude reaction mixture redissolved in DMF (1 mL). To this solution was added sodium hydride (13.8 mg, 0.32 mmol, 1.5 equiv; 55% free-flowing powder moistened with oil; [CAS RN 7646-69-7]) and iodomethane (59.6 mg, 26 μL, 0.42 mmol, 2.0 equiv; [CAS RN 74-88-4]) and the reaction mixture stirred at 35° C. for 1 h. Purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 6.9 mg (8%) of the title compound. MS (ISP): 401.2 [M+H]⁺.

Example 46

N-(3-Chloro-pyridin-2-yl)-2-(2,5-dichloro-phenoxy)-N-methyl-nicotinamide

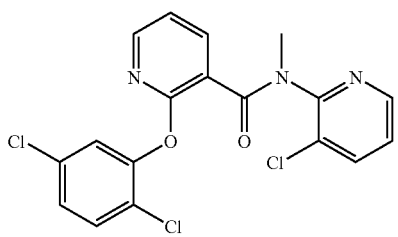

The title compound was prepared in analogy to Example 45 replacing 2-ethyl-phenylamine with 3-chloro-pyridin-2-ylamine ([CAS RN 39620-04-7]). MS (ISP): 407.8 [M+H]⁺.

Example 47

N-(4-Chloro-pyridin-3-yl)-2-(2,5-dichloro-phenoxy)-N-methyl-nicotinamide

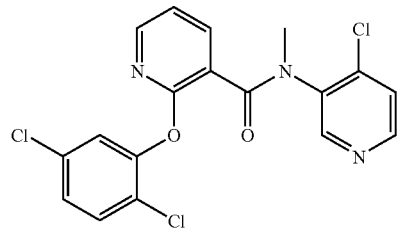

The title compound was prepared in analogy to Example 45 replacing 2-ethyl-phenylamine with 4-chloro-pyridin-3-ylamine ([CAS RN 20511-15-3]). MS (ISP): 409.4 [M+H]⁺.

Example 48

2-(2,5-Dichloro-phenoxy)-N-(2-methoxy-pyridin-3-yl)-N-methyl-nicotinamide

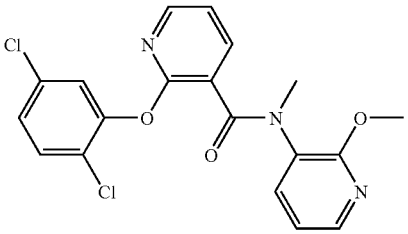

The title compound was prepared in analogy to Example 45 replacing 2-ethyl-phenylamine with 2-methoxy-pyridin-3-ylamine ([CAS RN 20265-38-7]). MS (ISP): 403.6 [M+H]⁺.

Example 49

N-(3-Chloro-2-methyl-phenyl)-2-(2,5-dichloro-phenoxy)-N-methyl-nicotinamide

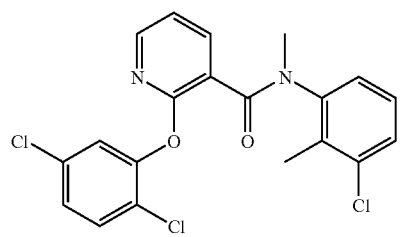

61

The title compound was prepared in analogy to Example 45 replacing 2-ethyl-phenylamine with 3-chloro-2-methyl-phenylamine ([CAS RN 20265-38-7]). MS (ISP): 420.8 [M+H]+.

Example 50

N-(5-Chloro-2-methyl-phenyl)-2-(2,5-dichloro-phenoxy)-N-methyl-nicotinamide

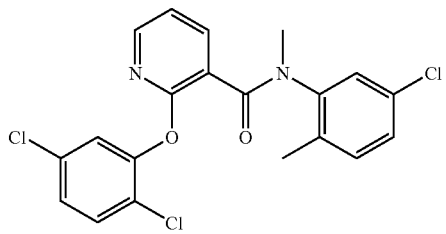

The title compound was prepared in analogy to Example 45 replacing 2-ethyl-phenylamine with 5-chloro-2-methyl-phenylamine ([CAS RN 95-79-4]). MS (ISP): 420.8 [M+H]+.

Example 51

N-(2-Chloro-6-methyl-phenyl)-2-(2,5-dichloro-phenoxy)-N-methyl-nicotinamide

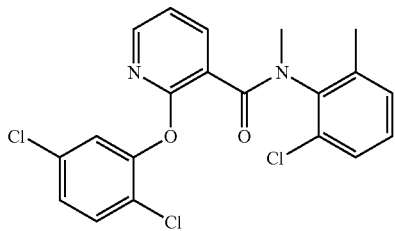

The title compound was prepared in analogy to Example 45 replacing 2-ethyl-phenylamine with 2-chloro-6-methyl-phenylamine ([CAS RN 87-63-8]). MS (ISP): 420.8 [M+H]+.

Example 52

2-(2,5-Dichloro-phenoxy)-N-(2,6-dimethyl-phenyl)-N-methyl-nicotinamide

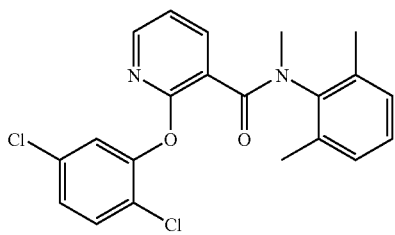

62

The title compound was prepared in analogy to Example 45 replacing 2-ethyl-phenylamine with 2,6-dimethyl-phenylamine ([CAS RN 87-62-7]). MS (ISP): 401.1 [M+H]+.

Example 53

2-(2,5-Dichloro-phenoxy)-N-(2-methoxy-6-methyl-phenyl)-N-methyl-nicotinamide

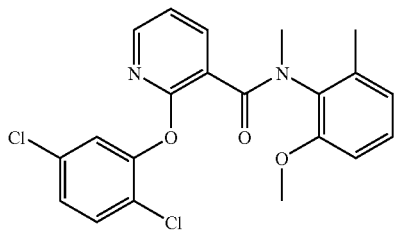

The title compound was prepared in analogy to Example 45 replacing 2-ethyl-phenylamine with 2-methoxy-6-methyl-phenylamine ([CAS RN 50868-73-0]). MS (ISP): 417.1 [M+H]+.

Example 54

2-(2,5-Dichloro-phenoxy)-N-(5-fluoro-2-methoxy-phenyl)-N-methyl-nicotinamide

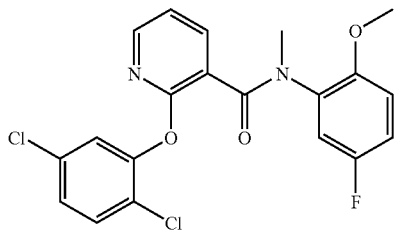

The title compound was prepared in analogy to Example 45 replacing 2-ethyl-phenylamine with 5-fluoro-2-methoxy-phenylamine ([CAS RN 437-83-2]). MS (ISP): 420.9 [M+H]+.

Example 55

N-(5-Chloro-2-methoxy-phenyl)-2-(2,5-dichloro-phenoxy)-N-methyl-nicotinamide

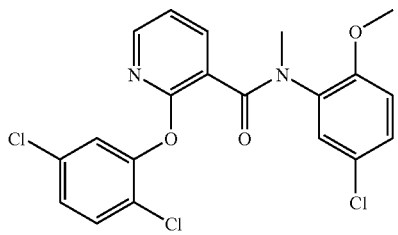

The title compound was prepared in analogy to Example 45 replacing 2-ethyl-phenylamine with 5-chloro-2-methoxy-phenylamine ([CAS RN 95-03-4]). MS (ISP): 436.8 [M+H]⁺.

Example 56

N-(4-Chloro-2-methyl-phenyl)-2-(2,5-dichloro-phenoxy)-N-methyl-nicotinamide

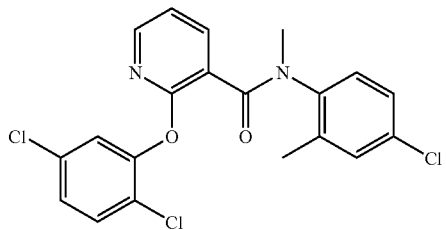

The title compound was prepared in analogy to Example 45 replacing 2-ethyl-phenylamine with 4-chloro-2-methyl-phenylamine ([CAS RN 95-69-2]). MS (ISP): 420.9 [M+H]⁺.

Example 57

2-(2,5-Dichloro-phenoxy)-N-(2,3-dimethyl-phenyl)-N-methyl-nicotinamide

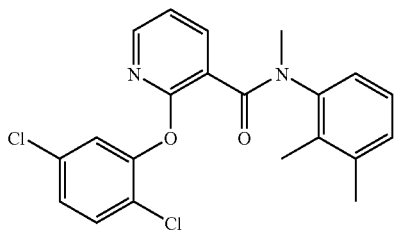

The title compound was prepared in analogy to Example 45 replacing 2-ethyl-phenylamine with 2,3-dimethyl-phenylamine ([CAS RN 87-59-2]). MS (ISP): 402.6 [M+H]⁺.

Example 58

2-(2,5-Dichloro-phenoxy)-N-(2,4-dimethyl-phenyl)-N-methyl-nicotinamide

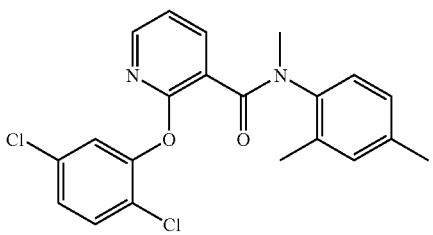

The title compound was prepared in analogy to Example 45 replacing 2-ethyl-phenylamine with 2,4-dimethyl-phenylamine ([CAS RN 95-68-1]). MS (ISP): 401.0 [M+H]⁺.

Example 59

2-(2,5-Dichloro-phenoxy)-N-(2-methoxy-5-methyl-phenyl)-N-methyl-nicotinamide

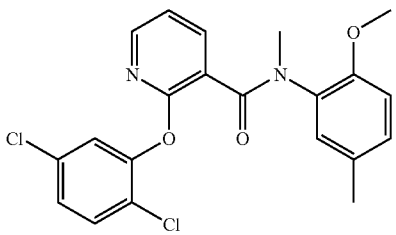

The title compound was prepared in analogy to Example 45 replacing 2-ethyl-phenylamine with 2-methoxy-5-methyl-phenylamine ([CAS RN 120-71-8]). MS (ISP): 416.7 [M+H]⁺.

Example 60

2-(2,5-Dichloro-phenoxy)-N-(2,6-dimethoxy-phenyl)-N-methyl-nicotinamide

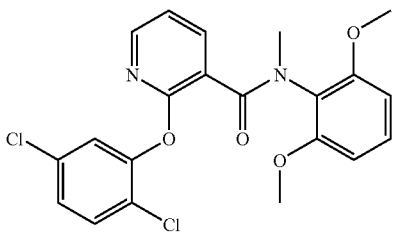

The title compound was prepared in analogy to Example 45 replacing 2-ethyl-phenylamine with 2,6-dimethoxy-phenylamine ([CAS RN 2734-70-5]). MS (ISP): 433.1 [M+H]⁺.

Example 61

N-(6-Chloro-4-methyl-pyridin-3-yl)-2-(2,5-dichloro-phenoxy)-N-methyl-nicotinamide

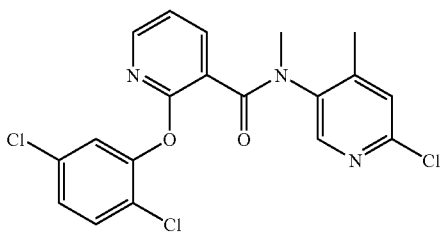

The title compound was prepared in analogy to Example 45 replacing 2-ethyl-phenylamine with 6-chloro-4-methyl-pyridin-3-ylamine ([CAS RN 66909-38-4]). MS (ISP): 422.1 [M+H]⁺.

Example 62

N-(2-Cyano-phenyl)-2-(2,5-dichloro-phenoxy)-N-methyl-nicotinamide

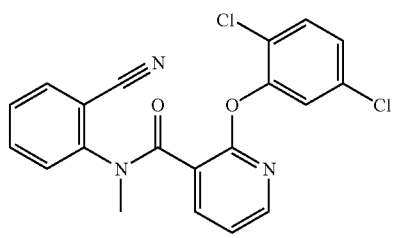

The title compound was prepared in analogy to Example 45 replacing 2-ethyl-phenylamine with 2-amino-benzonitrile ([CAS RN 1885-29-6]). MS (ISP): 398.1 [M+H]⁺.

Example 63

2-(2,5-Dichloro-phenoxy)-N-(2-fluoro-phenyl)-N-methyl-nicotinamide

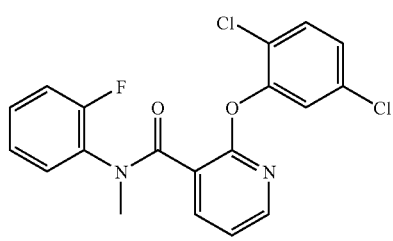

The title compound was prepared in analogy to Example 45 replacing 2-ethyl-phenylamine with 2-fluoro-phenylamine ([CAS RN 348-54-9]). MS (ISP): 391.1 [M+H]⁺.

Example 64

2-(2,5-Dichloro-phenoxy)-N-(2,6-difluoro-phenyl)-N-methyl-nicotinamide

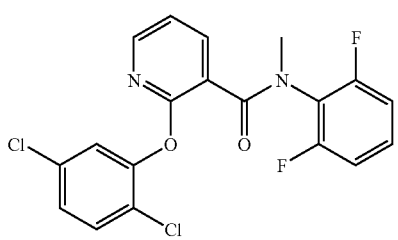

The title compound was prepared in analogy to Example 45 replacing 2-ethyl-phenylamine with 2,6-difluoro-phenylamine ([CAS RN 5509-65-9]). MS (ISP): 409.1 [M+H]⁺.

Example 65

2-(2,5-Dichloro-phenoxy)-N-methyl-N-(2-pyrrol-1-yl-phenyl)-nicotinamide

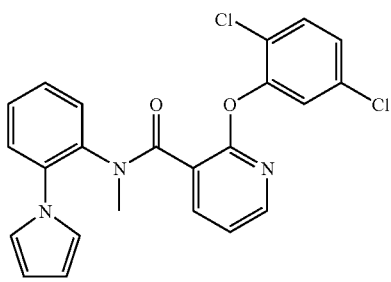

The title compound was prepared in analogy to Example 45 replacing 2-ethyl-phenylamine with 2-pyrrol-1-yl-phenylamine ([CAS RN 6025-60-1]). MS (ISP): 438.2 [M+H]⁺.

Example 66

2-(2,5-Dichloro-phenoxy)-N-(2,4-difluoro-phenyl)-N-methyl-nicotinamide

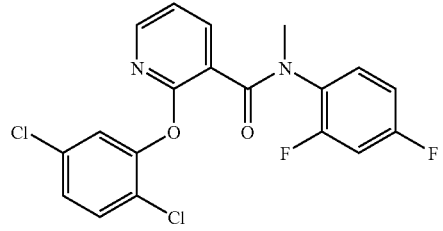

The title compound was prepared in analogy to Example 45 replacing 2-ethyl-phenylamine with 2,4-difluoro-phenylamine ([CAS RN 367-25-9]). MS (ISP): 409.1 [M+H]⁺.

Example 67

[2-(2,5-Dichloro-phenoxy)-pyridin-3-yl]-(2-methyl-3,4-dihydro-2H-quinolin-1-yl)-methanone

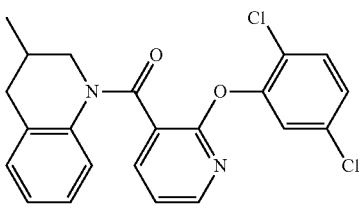

A solution of 2-(2,5-dichloro-phenoxy)-nicotinic acid (34.1 mg, 0.12 mmol, 1.0 equiv; Example 31, Step 1) in thionyl chloride (492 mg, 300 μL, 4.14 mmol, 34.5 equiv;

[CAS RN 7719-09-7]) was heated to 100° C. over night. The reaction mixture was concentrated under reduced pressure, remaining thionyl chloride removed by azotropic distillation with toluene and the residue dissolved in anhydrous DMF (1 mL). To this solution was added N-ethyldiisopropylamine (155 mg, 204 μL, 1.20 mmol, 10.0 equiv; [CAS RN 7087-68-5]) and 2-methyl-1,2,3,4-tetrahydro-quinoline (22.1 mg, 0.15 mmol, 1.25 equiv; [CAS RN 1780-19-4]) and the reaction mixture heated by microwave irradiation to 100° C. for 15 min. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 9 mg (18%) of the title compound. MS (ISP): 412.9 [M+H]$^+$.

Example 68

[2-(2,5-Dichloro-phenoxy)-pyridin-3-yl]-(8-fluoro-6-methyl-3,4-dihydro-2H-quinolin-1-yl)-methanone

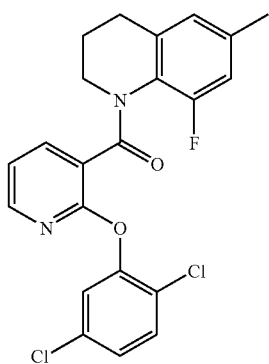

The title compound was prepared in analogy to Example 36 replacing 3,4-dihydro-2H-benzo[1,4]oxazine with 8-fluoro-6-methyl-1,2,3,4-tetrahydro-quinoline ([CAS RN 954260-80-1]). MS (ISP): 431.2 [M+H]$^+$.

Example 69

N-(2-Chloro-4-methyl-pyridin-3-yl)-2-(2,5-dichloro-phenoxy)-N-methyl-nicotinamide

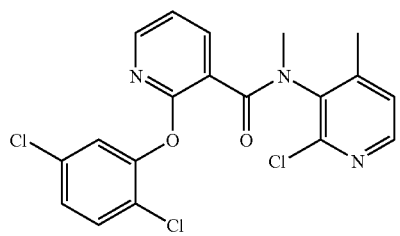

To a solution of 2-(2,5-dichloro-phenoxy)-nicotinic acid (56.6 mg, 0.2 mmol, 1.0 equiv; Example 31, Step 1) in anhydrous DMF (1 mL) was added 2-chloro-4-methyl-pyridin-3-ylamine (34.2 mg, 0.24 mmol, 1.2 equiv; [CAS RN 133627-45-9]), N-ethyldiisopropylamine (129.0 mg, 175 μL, 1.0 mmol, 5.0 equiv; [CAS RN 7087-68-5]) and HATU (91.2 mg, 0.24 mmol, 1.2 equiv; [CAS RN 148893-10-1]) and the reaction mixture stirred at rt. After 18 h, sodium hydride (13.0 mg, 0.3 mmol, 1.5 equiv; 55% free-flowing powder moistened with oil; [CAS RN 7646-69-7]) and iodomethane (56.8 mg, 25 μL, 0.4 mmol, 2.0 equiv; [CAS RN 74-88-4]) were added and stirring continued at 40° C. for 2 h. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 2.9 mg (3%) of the title compound. MS (ISP): 424.1 [M+H]$^+$.

Example 70

[2-(2,5-Dichloro-phenoxy)-pyridin-3-yl]-(8-methoxy-3,4-dihydro-2H-quinolin-1-yl)-methanone

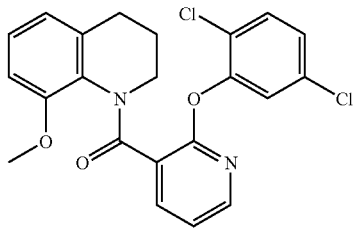

To a solution of 2-(2,5-dichloro-phenoxy)-nicotinic acid (56.6 mg, 0.2 mmol, 1.0 equiv; Example 31, Step 1) in anhydrous DMF (1 mL) was added 8-methoxy-1,2,3,4-tetrahydro-quinoline (39.2 mg, 0.24 mmol, 1.2 equiv; [CAS RN 53899-17-5]), N-ethyldiisopropylamine (129.0 mg, 175 μL, 1.0 mmol, 5.0 equiv; [CAS RN 7087-68-5]) and HATU (91.2 mg, 0.24 mmol, 1.2 equiv; [CAS RN 148893-10-1]) and the reaction mixture stirred at 50° C. over night. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 10.6 mg (12%) of the title compound. MS (ISP): 429.3 [M+H]$^+$.

Example 71

(6-Chloro-3,4-dihydro-2H-quinolin-1-yl)-[2-(2,5-dichloro-phenoxy)-pyridin-3-yl]-methanone

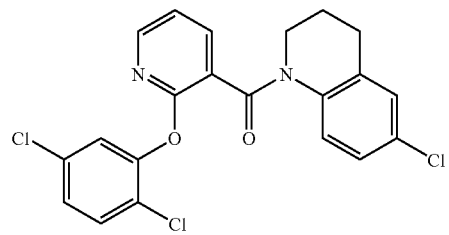

The title compound was prepared in analogy to Example 70 replacing 8-methoxy-1,2,3,4-tetrahydro-quinoline with 6-chloro-1,2,3,4-tetrahydro-quinoline ([CAS RN 49716-18-9]). MS (ISP): 435.0 [M+H]$^+$.

Example 72

[2-(2,5-Dichloro-phenoxy)-pyridin-3-yl]-(6-fluoro-2,3-dihydro-benzo[1,4]oxazin-4-yl)-methanone

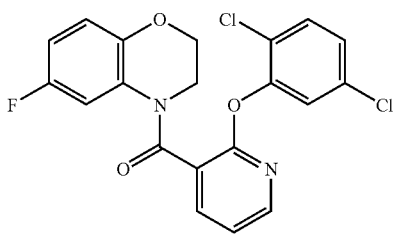

The title compound was prepared in analogy to Example 70 replacing 8-methoxy-1,2,3,4-tetrahydro-quinoline with 6-fluoro-3,4-dihydro-2H-benzo[1,4]oxazine hydrochloride ([CAS RN 105655-00-3]). MS (ISP): 419.3 [M+H]+.

Example 73

[2-(2,5-Dichloro-phenoxy)-pyridin-3-yl]-(6,8-difluoro-2,3-dihydro-benzo[1,4]oxazin-4-yl)-methanone

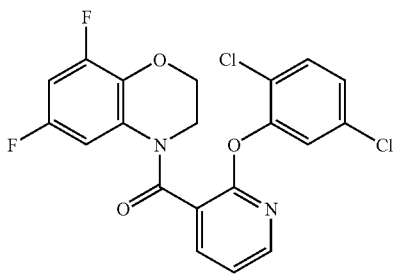

The title compound was prepared in analogy to Example 70 replacing 8-methoxy-1,2,3,4-tetrahydro-quinoline with 6,8-difluoro-3,4-dihydro-2H-benzo[1,4]oxazine ([CAS RN 939759-10-1]). MS (ISP): 437.0 [M+H]+.

Example 74

[2-(2,5-Dichloro-phenoxy)-pyridin-3-yl]-(4-phenyl-3,4-dihydro-2H-quinoxalin-1-yl)-methanone

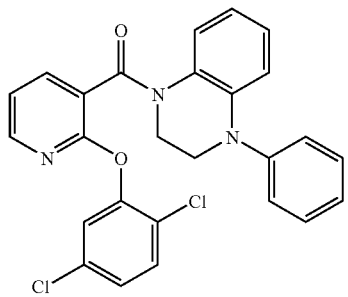

Step 1: 1-Phenyl-1,2,3,4-tetrahydro-quinoxaline

To a suspension of lithium aluminium hydride (3.99 g, 105.0 mmol, 5.0 equiv) in THF (30 mL) was added slowly a solution of 1-phenyl-1,4-dihydro-quinoxaline-2,3-dione (5.00 g, 21.0 mmol, 1.0 equiv; prepared as described by S.-K. Lin *Molecules* 1996, 1, 37-40) in THF (50 mL). After heating the reaction mixture to reflux for 16 h, a solution of 1 M NaOH (100 mL) was added. The reaction mixture was stirred for a few minutes, MgSO4 added and then filtered over Celite. Extraction of the filter cake with ethyl acetate (3×100 mL) and evaporation of the solvent under reduced pressure provided the crude reaction product which was purified by silica column chromatography eluting with a gradient of heptane/ethyl acetate to afford 3.23 g (73%) of the title compound as an orange solid. MS (ED: 210.0 [M]+.

Step 2

The title compound was prepared in analogy to Example 70 replacing 8-methoxy-1,2,3,4-tetrahydro-quinoline with 1-phenyl-1,2,3,4-tetrahydro-quinoxaline. MS (ISP): 476.0 [M+H]+.

Example 75

2-(2,5-Dichloro-phenoxy)-N-(4-methoxy-pyridin-3-yl)-N-methyl-nicotinamide

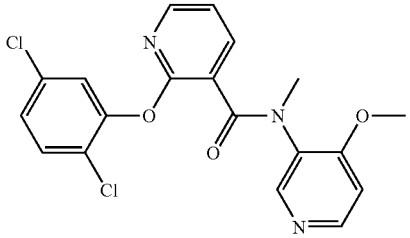

The title compound was prepared in analogy to Example 69 replacing 2-chloro-4-methyl-pyridin-3-ylamine with 4-methoxy-pyridin-3-ylamine ([CAS RN 33631-09-3]). MS (ISP): 405.9 [M+H]+.

Example 76

[2-(2,4-Dichloro-phenoxy)-pyridin-3-yl]-(3,4-dihydro-2H-quinolin-1-yl)-methanone

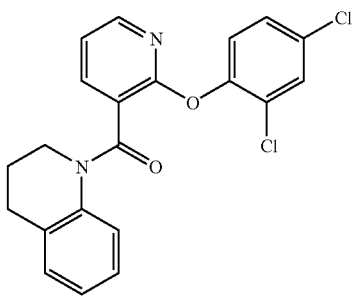

Step 1: 2-(2,4-Dichloro-phenoxy)-nicotinic acid

To a solution of 2-chloro-nicotinic acid (2.15 g, 13.65 mmol, 1.0 equiv; [CAS RN 2942-59-8]) and 2,4-dichlorophenol (2.22 g, 13.65 mmol, 1.0 equiv; [CAS RN 120-83-2]) in toluene (40 mL) was added caesium carbonate (8.89 g, 27.29 mmol, 2.0 equiv; [CAS RN 534-17-8]) and tetrakis(acetonitrile)copper(I) hexafluorophosphate (1.02 g, 2.73 mmol, 0.2 equiv; [CAS RN 64443-05-6]). The reaction mixture was heated to reflux over night. The solvent was evaporated under reduced pressure and the crude reaction product taken up in water (100 mL) acidified to pH 1 by addition of a solution of 1 M HCl and extracted with ethyl acetate (3×100 mL). The combined organic phases were dried over MgSO$_4$ and the product purified by silica column chromatography using a MPLC system (CombiFlash Companion, Isco Inc.) eluting with a gradient of dichloromethane/methanol affording 1.69 g (44%) of the title compound as an off-white solid. $^1$H NMR (400 MHz, DMSO): δ7.26 (dd, J=7.6 Hz, J=4.8 Hz, 1H), 7.36 (d, J=8.7 Hz, 1H), 7.49 (dd, J=8.7 Hz, J=2.6 Hz, 1H), 7.76 (d, J=2.4 Hz, 1H), 8.25 (dd, J=4.8 Hz, J=2.2 Hz, 1H), 8.30 (dd, J=7.5 Hz, J=2.2 Hz, 1H), 13.33 (s, 1H). MS (ISN): 282.3 [M−H]$^-$.

Step 2

The title compound was prepared in analogy to Example 37 replacing 2-(2,5-dichloro-phenoxy)-nicotinic acid with 2-(2,4-dichloro-phenoxy)-nicotinic acid and 6-fluoro-1,2,3,4-tetrahydro-quinoline with 1,2,3,4-tetrahydro-quinoline ([CAS RN 635-46-1]). MS (ISP): 399.0 [M+H]$^+$.

Example 77

[2-(3-Chloro-4-fluoro-phenoxy)-pyridin-3-yl]-(6-methyl-3,4-dihydro-2H-quinolin-1-yl)-methanone

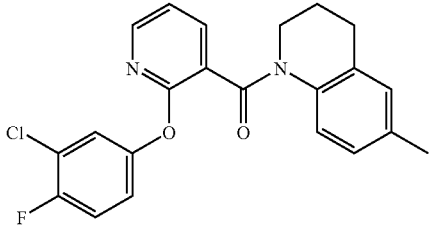

Step 1: 2-(3-Chloro-4-fluoro-phenoxy)-nicotinic acid 2-(3-Chloro-4-fluoro-phenoxy)-nicotinic acid was prepared in analogy to Example 1, Step 1, replacing 3-trifluoromethyl-phenol with 3-chloro-4-fluoro-phenol ([CAS RN 2613-23-2]). MS (ISN): 265.9 [M−H]$^-$.

Step 2

A solution of 2-(3-chloro-4-fluoro-phenoxy)-nicotinic acid (32.1 mg, 0.12 mmol, 1.0 equiv) in thionyl chloride (57 mg, 35 pt, 0.48 mmol, 4.0 equiv; [CAS RN 7719-09-7]) was stirred at rt for 1 h. The reaction mixture was concentrated under reduced pressure, remaining thionyl chloride removed by azotropic distillation with toluene and the residue dissolved in anhydrous DMF (1 mL). To this solution was added N-ethyldiisopropylamine (77.6 mg, 102 μL, 0.60 mmol, 5.0 equiv; [CAS RN 7087-68-5]) and 6-methyl-1,2,3,4-tetrahydro-quinoline (21.2 mg, 0.14 mmol, 1.2 equiv; [CAS RN 91-61-2]) and the reaction mixture heated by microwave irradiation to 140° C. for 15 min. Removal of the solvent mixture under reduced pressure and purification by preparative HPLC on reversed phase (Xterra® PrepMSC 18, 5 μm, 19×50 mm column equipped with a Gilson Liquid Handler 215 auto sampler, two Rainin Dynamax® SD-300 pumps, a Sedex ELSD 75 lightscatter and a Dionex UVD 340S UV detector) eluting with a gradient of acetonitrile/water provided 3.7 mg (8%) of the title compound. MS (ISP): 397.0 [M+H]$^+$.

Example 78

[2-(3-Chloro-4-fluoro-phenoxy)-pyridin-3-yl]-(3,4-dihydro-2H-[1,5]naphthyridin-1-yl)-methanone

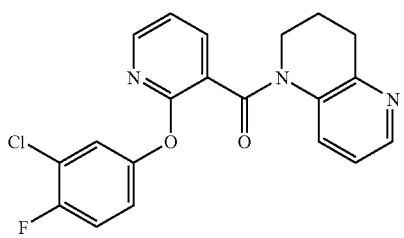

The title compound was prepared in analogy to Example 67 replacing 2-(2,5-dichloro-phenoxy)-nicotinic acid with 2-(3-chloro-4-fluoro-phenoxy)-nicotinic acid (Example 77, Step 1) and 2-methyl-1,2,3,4-tetrahydro-quinoline with 1,2,3,4-tetrahydro-[1,5]naphthyridine ([CAS RN 13993-61-8]). MS (ISN): 383.9 [M+H]$^+$.

Example 79

[2-(3-Chloro-4-fluoro-phenoxy)-pyridin-3-yl]-(6,7-difluoro-3,4-dihydro-2H-quinolin-1-yl)-methanone

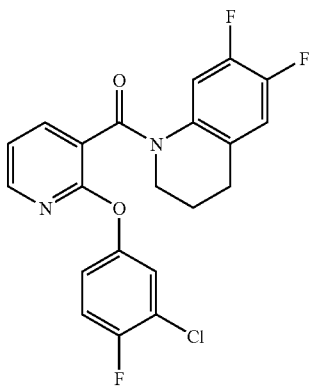

To a solution of 2-(3-chloro-4-fluoro-phenoxy)-nicotinic acid (32.1 mg, 0.12 mmol, 1.0 equiv; Example 77, Step 1) in dichloromethane (1 mL) was added 6,7-difluoro-1,2,3,4-tetrahydro-quinoline (24.4 mg, 0.14 mmol, 1.2 equiv; [CAS RN 953717-64-1]), tri-n-butylamine (111.2 mg, 143 μL, 0.60 mmol, 5.0 equiv; [CAS RN 102-82-9]) and 2-chloro-1-methylpyridinium iodide (36.8 mg, 0.14 mmol, 1.2 equiv; [CAS RN 14338-32-0]). The reaction mixture was heated by microwave irradiation to 60° C. for 15 min. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 4.7 mg (9%) of the title compound. MS (ISP): 419.0 [M+H]+.

Example 80

[2-(2,5-Dichloro-phenoxy)-5-fluoro-pyridin-3-yl]-(2-methyl-3,4-dihydro-2H-quinolin-1-yl)-methanone

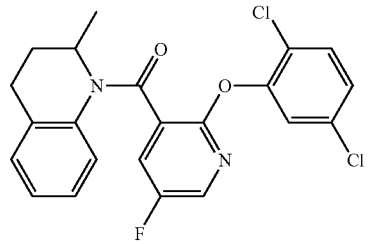

Step 1: 2-(2,5-Dichloro-phenoxy)-5-fluoro-nicotinic acid 2-(2,5-Dichloro-phenoxy)-5-fluoro-nicotinic acid was prepared in analogy to Example 1, Step 1, replacing 2-chloro-nicotinic acid with 2-chloro-5-fluoro-nicotinic acid ([CAS RN 38186-88-8]) and 3-trifluoromethyl-phenol with 2,5-dichloro-phenol ([CAS RN 583-78-8]). ¹H NMR (400 MHz, DMSO): δ7.38 (dd, J=8.4 Hz, J=2.4 Hz, 1H), 7.51 (d, J=2.4 Hz, 1H), 7.62 (d, J=8.4 Hz, 1H), 8.23 (dd, J=8.1 Hz, J=3.2 Hz, 1H), 8.34 (d, J=3.2 Hz, 1H), 13.65 (s, 1H). ¹⁹F NMR (376.5 MHz, DMSO): −134.6. MS (ISN): 302.0 [M−H]−.

Step 2

A solution of 2-(2,5-dichloro-phenoxy)-5-fluoro-nicotinic acid (36.3 mg, 0.12 mmol, 1.0 equiv) in thionyl chloride (492 mg, 300 μL, 4.14 mmol, 34.5 equiv; [CAS RN 7719-09-7]) was heated to 100° C. over night. The reaction mixture was concentrated under reduced pressure, remaining thionyl chloride removed by azotropic distillation with toluene and the residue dissolved in anhydrous DMF (1 mL). To this solution was added N-ethyldiisopropylamine (155 mg, 204 μL, 1.20 mmol, 10.0 equiv; [CAS RN 7087-68-5]) and 2-methyl-1,2,3,4-tetrahydro-quinoline (22.1 mg, 0.15 mmol, 1.25 equiv; [CAS RN 1780-19-4]) and the reaction mixture heated by microwave irradiation to 120° C. for 15 min. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 11.5 mg (22%) of the title compound. MS (ISP): 430.8 [M+H]+.

Example 81

[2-(2,5-Dichloro-phenoxy)-5-fluoro-pyridin-3-yl]-(2,3-dihydro-benzo[1,4]oxazin-4-yl)-methanone

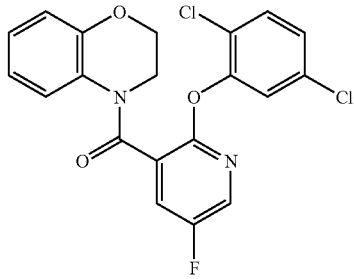

The title compound was prepared in analogy to Example 80, Step 2, replacing 2-methyl-1,2,3,4-tetrahydro-quinoline with 3,4-dihydro-2H-benzo[1,4]oxazine ([CAS RN 5735-53-5]). MS (ISN): 419.3 [M+H]+.

Example 82

1-[2-(2,5-Dichloro-phenoxy)-5-fluoro-pyridine-3-carbonyl]-1,2,3,4-tetrahydro-benzo[b]azepin-5-one

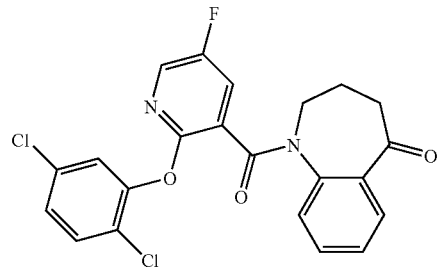

The title compound was prepared in analogy to Example 80, Step 2, replacing 2-methyl-1,2,3,4-tetrahydro-quinoline with 1,2,3,4-tetrahydro-benzo[b]azepin-5-one ([CAS RN 1127-74-8]). MS (ISN): 444.7 [M+H]+.

Example 83

[2-(2,5-Dichloro-phenoxy)-5-fluoro-pyridin-3-yl]-(3,4-dihydro-2H-quinolin-1-yl)-methanone

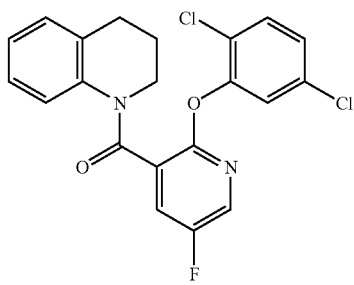

The title compound was prepared in analogy to Example 31, Step 2, replacing 2-(2,5-dichloro-phenoxy)-nicotinic acid with 2-(2,5-dichloro-phenoxy)-5-fluoro-nicotinic acid (Example 80, Step 1) and 6-methyl-1,2,3,4-tetrahydro-quinoline with 1,2,3,4-tetrahydro-quinoline ([CAS RN 635-46-1]). MS (ISP): 417.0 [M+H]$^+$.

Example 84

2-(2,5-Dichloro-phenoxy)-N-ethyl-5-fluoro-N-phenyl-nicotinamide

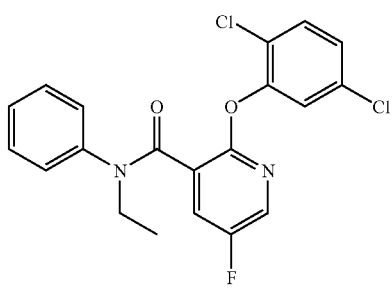

The title compound was prepared in analogy to Example 31, Step 2, replacing 2-(2,5-dichloro-phenoxy)-nicotinic acid with 2-(2,5-dichloro-phenoxy)-5-fluoro-nicotinic acid (Example 80, Step 1) and 6-methyl-1,2,3,4-tetrahydro-quinoline with ethyl-phenyl-amine ([CAS RN 103-69-5]). MS (ISP): 405.0 [M+H]$^+$.

Example 85

[2-(3-Chloro-phenoxy)-5-fluoro-pyridin-3-yl]-(6,7-difluoro-3,4-dihydro-2H-quinolin-1-yl)-methanone

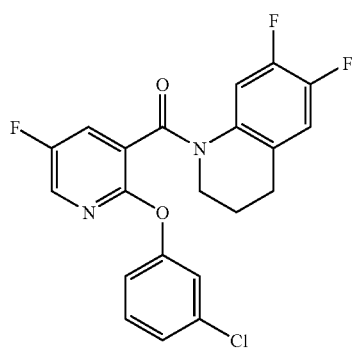

Step 1: 2-(3-Chloro-phenoxy)-5-fluoro-nicotinic acid 2-(3-Chloro-phenoxy)-5-fluoro-nicotinic acid was prepared in analogy to Example 1, Step 1, replacing 2-chloro-nicotinic acid with 2-chloro-5-fluoro-nicotinic acid ([CAS RN 38186-88-8]) and 3-trifluoromethyl-phenol with 3-chloro-phenol ([CAS RN 108-43-0]). $^1$H NMR (400 MHz, DMSO): δ7.09 (dd, J=8.4 Hz, J=1.6 Hz, 1H), 7.24-7.25 (m, 2H), 7.44 (t, J=8.4 Hz, 1H), 8.19 (dd, J=8.1 Hz, J=3.2 Hz, 1H), 8.37 (d, J=3.2 Hz, 1H), 13.60 (s, 1H). $^{19}$F NMR (376.5 MHz, DMSO): −134.4. MS (ISN): 266.0 [M−H]$^-$.

Step 2

The title compound was prepared in analogy to Example 79 replacing 2-(3-chloro-4-fluoro-phenoxy)-nicotinic acid with 2-(3-chloro-phenoxy)-5-fluoro-nicotinic acid. MS (ISP): 419.3 [M+H]$^+$.

Example 86

[2-(3-Chloro-4-fluoro-phenoxy)-5-fluoro-pyridin-3-yl]-(3,4-dihydro-2H-quinolin-1-yl)-methanone

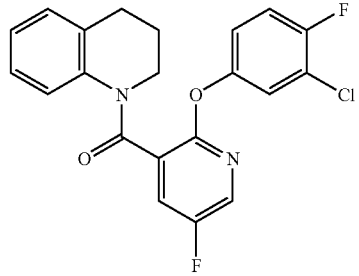

Step 1: 2-(3-Chloro-4-fluoro-phenoxy)-5-fluoro-nicotinic acid 2-(3-Chloro-4-fluoro-phenoxy)-5-fluoro-nicotinic acid was prepared in analogy to Example 1, Step 1, replacing 2-chloro-nicotinic acid with 2-chloro-5-fluoro-nicotinic acid ([CAS RN 38186-88-8]) and 3-trifluoromethyl-phenol with 3-chloro-4-fluoro-phenol ([CAS RN 2613-23-2]). $^1$H NMR (400 MHz, DMSO): δ7.16-7.19 (m, 1H), 7.44-7.48 (m, 2H), 8.19 (dd, J=8.1 Hz, J=3.2 Hz, 1H), 8.35 (d, J=3.2 Hz, 1H), 13.60 (s, 1H). $^{19}$F NMR (376.5 MHz, DMSO): −121.6, −134.8. MS (ISN): 283.8 [M−H]$^-$.

Step 2

The title compound was prepared in analogy to Example 31, Step 2, replacing 2-(2,5-dichloro-phenoxy)-nicotinic acid with 2-(3-chloro-4-fluoro-phenoxy)-5-fluoro-nicotinic acid and 6-methyl-1,2,3,4-tetrahydro-quinoline with 1,2,3,4-tetrahydro-quinoline ([CAS RN 635-46-1]). MS (ISP): 401.0 [M+H]$^+$.

Example 87

[2-(3-Chloro-4-fluoro-phenoxy)-5-fluoro-pyridin-3-yl]-(6,7-difluoro-3,4-dihydro-2H-quinolin-1-yl)-methanone

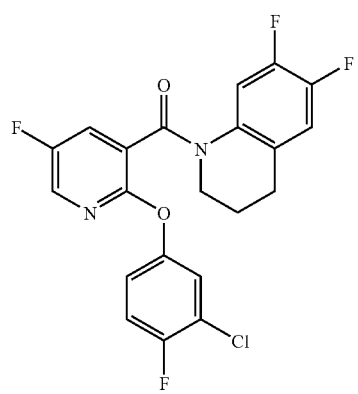

The title compound was prepared in analogy to Example 79 replacing 2-(3-chloro-4-fluoro-phenoxy)-nicotinic acid with 2-(3-chloro-4-fluoro-phenoxy)-5-fluoro-nicotinic acid (Example 86, Step 1). MS (ISP): 437.0 [M+H]+.

Example 88

[2-(3-Chloro-4-fluoro-phenoxy)-5-fluoro-pyridin-3-yl]-(8-methyl-3,4-dihydro-2H-quinolin-1-yl)-methanone

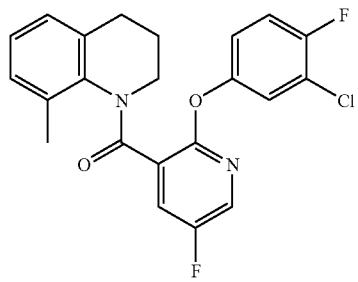

A solution of 2-(3-chloro-4-fluoro-phenoxy)-5-fluoro-nicotinic acid (34.3 mg, 0.12 mmol, 1.0 equiv; Example 86, Step 1) in thionyl chloride (492 mg, 300 µL, 4.14 mmol, 34.5 equiv; [CAS RN 7719-09-7]) was heated to 100° C. over night. The reaction mixture was concentrated under reduced pressure, remaining thionyl chloride removed by azotropic distillation with toluene and the residue dissolved in anhydrous DMF (1 mL). To this solution was added N-ethyldiisopropylamine (155 mg, 204 µL, 1.20 mmol, 10.0 equiv; [CAS RN 7087-68-5]) and 2-methyl-1,2,3,4-tetrahydro-quinoline (22.1 mg, 0.15 mmol, 1.25 equiv; [CAS RN 1780-19-4]) and the reaction mixture heated by microwave irradiation to 100° C. for 20 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 10.6 mg (21%) of the title compound. MS (ISP): 414.9 [M+H]+.

Example 89

[3-(2,5-Dichloro-phenoxy)-pyridin-4-yl]-(3,4-dihydro-2H-quinolin-1-yl)-methanone

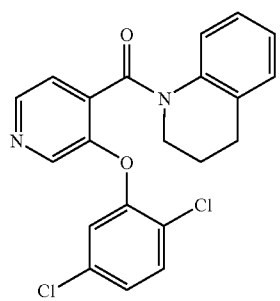

Step 1: (3-Bromo-pyridin-4-yl)-(3,4-dihydro-2H-quinolin-1-yl)-methanone (3-Bromo-pyridin-4-yl)-(3,4-dihydro-2H-quinolin-1-yl)-methanone was prepared in analogy to Example 6, Step 1, replacing 2-chloro-nicotinic acid with 3-bromo-isonicotinic acid ([CAS RN 13959-02-9]). MS (ISP): 319.1 [M+H]+.

Step 2

To a solution of (3-bromo-pyridin-4-yl)-(3,4-dihydro-2H-quinolin-1-yl)-methanone (41.2 mg, 0.13 mmol, 1.0 equiv) and 2,5-dichloro-phenol (21.2 mg, 0.13 mmol, 1.0 equiv; [CAS RN 583-78-8]) in DMAc (1 mL) was added potassium carbonate (35.9 mg, 0.26 mmol, 2.0 equiv; [CAS RN 584-08-7]) and copper(I) iodide (5.0 mg, 0.026 mmol, 0.2 equiv; [CAS RN 7681-65-4]). The reaction mixture was heated by microwave irradiation to 180° C. for 8 h. Purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 5 mg (10%) of the title compound. MS (ISP): 399.1 [M+H]+.

Example 90

[3-(2,5-Dichloro-phenoxy)-pyridin-4-yl]-(7-fluoro-3,4-dihydro-2H-quinolin-1-yl)-methanone

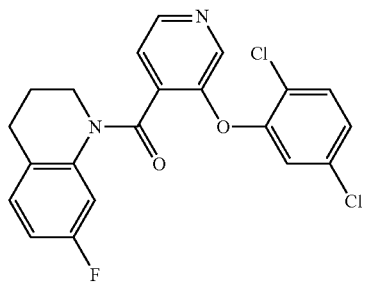

The title compound was prepared in analogy to Example 89, Step 1, replacing 1,2,3,4-tetrahydro-quinoline with 7-fluoro-1,2,3,4-tetrahydro-quinoline hydrochloride (commercially available from Zannan Pharma Ltd). Microwave heating in step 2 was conducted at 180° C. for 1 h followed by 150° C. for 3 h. MS (ISP): 416.7 [M+H]+.

Example 91

[3-(2,5-Dichloro-phenoxy)-pyridin-4-yl]-(6-fluoro-3,4-dihydro-2H-quinolin-1-yl)-methanone

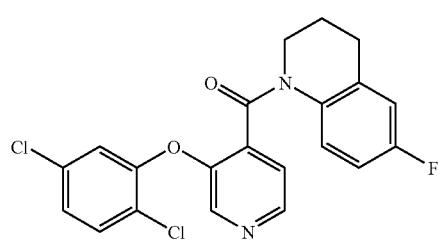

The title compound was prepared in analogy to Example 89, Step 1, replacing 1,2,3,4-tetrahydro-quinoline with 6-fluoro-1,2,3,4-tetrahydro-quinoline ([CAS RN 59611-52-8]). Microwave heating in step 2 was conducted at 180° C. for 1 h followed by 150° C. for 3 h. MS (ISP): 416.8 [M+H]+.

Example 92

[3-(2,5-Dichloro-phenoxy)-pyridin-4-yl]-(6,8-difluoro-3,4-dihydro-2H-quinolin-1-yl)-methanone

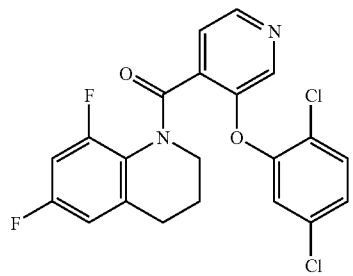

The title compound was prepared in analogy to Example 89, Step 1, replacing 1,2,3,4-tetrahydro-quinoline with 6,8-difluoro-1,2,3,4-tetrahydro-quinoline ([CAS RN 926218-72-6]). Microwave heating in step 2 was conducted at 180° C. for 1 h followed by 150° C. for 3 h. MS (ISP): 434.8 [M+H]+.

Example 93

3-(2,5-Dichloro-phenoxy)-N-methyl-N-o-tolyl-isonicotinamide

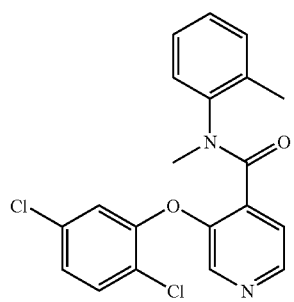

The title compound was prepared in analogy to Example 89, Step 1, replacing 1,2,3,4-tetrahydro-quinoline with methyl-o-tolyl-amine ([CAS RN 611-21-2]). Microwave heating in step 2 was conducted at 180° C. for 2 h followed by 150° C. for 8 h. MS (ISP): 387.2 [M+H]+.

Example 94

N-(2-Chloro-phenyl)-3-(2,5-dichloro-phenoxy)-N-methyl-isonicotinamide

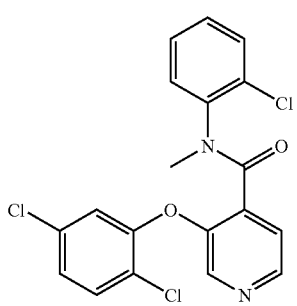

The title compound was prepared in analogy to Example 89, Step 1, replacing 1,2,3,4-tetrahydro-quinoline with (2-chloro-phenyl)-methyl-amine ([CAS RN 932-32-1]). Microwave heating in step 2 was conducted at 180° C. for 1 h followed by 150° C. for 3 h. MS (ISP): 408.6 [M+H]+.

Example 95

3-(2,5-Dichloro-phenoxy)-N-(2-methoxy-phenyl)-N-methyl-isonicotinamide

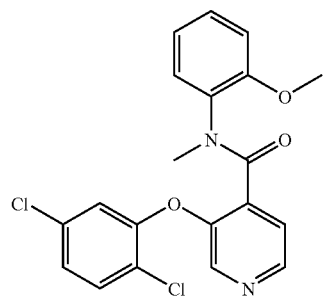

The title compound was prepared in analogy to Example 89, Step 1, replacing 1,2,3,4-tetrahydro-quinoline with (2-methoxy-phenyl)-methyl-amine ([CAS RN 10541-78-3]). Microwave heating in step 2 was conducted at 180° C. for 11 h followed by 150° C. for 1 h. MS (ISP): 403.2 [M+H]+.

Example 96

[3-(2,4-Dichloro-phenoxy)-pyridin-4-yl]-(7-fluoro-3,4-dihydro-2H-quinolin-1-yl)-methanone

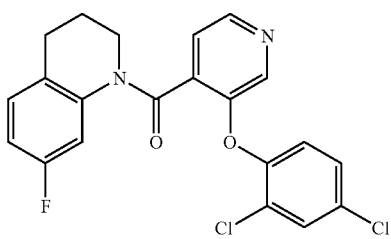

The title compound was prepared in analogy to Example 89, Step 1, replacing 1,2,3,4-tetrahydro-quinoline with 7-fluoro-1,2,3,4-tetrahydro-quinoline hydrochloride (commercially available from Zannan Pharma Ltd). Step 2 was performed by replacing 2,5-dichloro-phenol with 2,4-dichloro-phenol ([CAS RN 120-83-2]) and conducting microwave heating at 180° C. for 1 h followed by 150° C. for 3 h. MS (ISP): 416.8 [M+H]⁺.

Example 97

[3-(2,4-Dichloro-phenoxy)-pyridin-4-yl]-(7-fluoro-3,4-dihydro-2H-quinolin-1-yl)-methanone

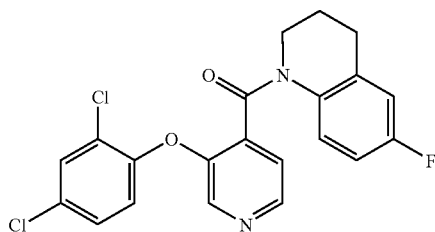

The title compound was prepared in analogy to Example 89, Step 1, replacing 1,2,3,4-tetrahydro-quinoline with 6-fluoro-1,2,3,4-tetrahydro-quinoline ([CAS RN 59611-52-8]). Step 2 was performed by replacing 2,5-dichloro-phenol with 2,4-dichloro-phenol ([CAS RN 120-83-2]) and conducting microwave heating at 180° C. for 1 h followed by 150° C. for 3 h. MS (ISP): 416.7 [M+H]⁺.

Example 98

[3-(2,4-Dichloro-phenoxy)-pyridin-4-yl]-(6,8-difluoro-3,4-dihydro-2H-quinolin-1-yl)-methanone

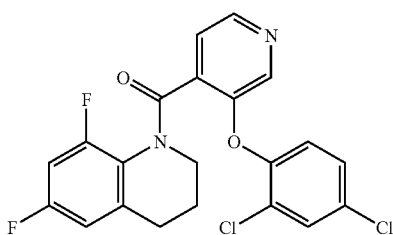

The title compound was prepared in analogy to Example 89, Step 1, replacing 1,2,3,4-tetrahydro-quinoline with 6,8-difluoro-1,2,3,4-tetrahydro-quinoline ([CAS RN 926218-72-6]). Step 2 was performed by replacing 2,5-dichloro-phenol with 2,4-dichloro-phenol ([CAS RN 120-83-2]) and conducting microwave heating at 180° C. for 1 h. MS (ISP): 435.1 [M+H]⁺.

Example 99

3-(2,4-Dichloro-phenoxy)-N-methyl-N-o-tolyl-isonicotinamide

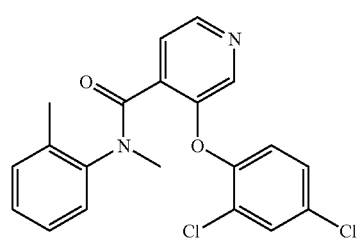

The title compound was prepared in analogy to Example 89, Step 1, replacing 1,2,3,4-tetrahydro-quinoline with methyl-o-tolyl-amine ([CAS RN 611-21-2]). Step 2 was performed by replacing 2,5-dichloro-phenol with 2,4-dichloro-phenol ([CAS RN 120-83-2]) and conducting microwave heating at 180° C. for 1 h followed by 150° C. for 3 h. MS (ISP): 386.7 [M+H]⁺.

Example 100

N-(2-Chloro-phenyl)-3-(2,4-dichloro-phenoxy)-N-methyl-isonicotinamide

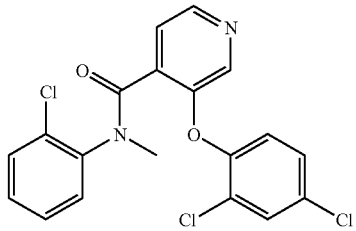

The title compound was prepared in analogy to Example 89, Step 1, replacing 1,2,3,4-tetrahydro-quinoline with (2-chloro-phenyl)-methyl-amine ([CAS RN 932-32-1]). Step 2 was performed by replacing 2,5-dichloro-phenol with 2,4-dichloro-phenol ([CAS RN 120-83-2]) and conducting microwave heating at 180° C. for 1 h followed by 150° C. for 3 h. MS (ISP): 408.6 [M+H]⁺.

Example 101

3-(2,4-Dichloro-phenoxy)-N-(2-methoxy-phenyl)-N-methyl-isonicotinamide

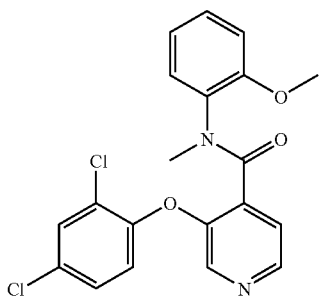

The title compound was prepared in analogy to Example 89, Step 1, replacing 1,2,3,4-tetrahydro-quinoline with (2-methoxy-phenyl)-methyl-amine ([CAS RN 10541-78-3]). Step 2 was performed by replacing 2,5-dichloro-phenol with 2,4-dichloro-phenol ([CAS RN 120-83-2]) and conducting

Example 102

3-(2,4-Dichloro-phenoxy)-N-(2-methoxy-pyridin-3-yl)-N-methyl-isonicotinamide

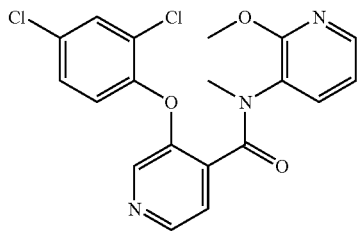

The title compound was prepared in analogy to Example 89, Step 1, replacing 1,2,3,4-tetrahydro-quinoline with 2-methoxy-pyridin-3-ylamine ([CAS RN 20265-38-7]). Step 2 was performed by replacing 2,5-dichloro-phenol with 2,4-dichloro-phenol ([CAS RN 120-83-2]) and conducting microwave heating at 180° C. for 2 h followed by 150° C. for 8 h. MS (ISP): 403.8 [M+H]⁺.

Example 103

[3-(3-Chloro-4-fluoro-phenoxy)-pyridin-4-yl]-(7-fluoro-3,4-dihydro-2H-quinolin-1-yl)-methanone

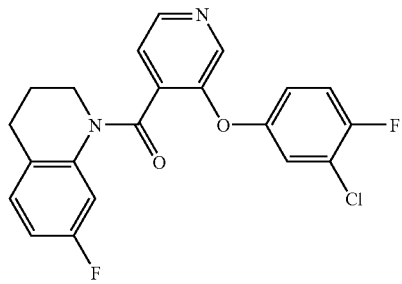

The title compound was prepared in analogy to Example 89, Step 1, replacing 1,2,3,4-tetrahydro-quinoline with 7-fluoro-1,2,3,4-tetrahydro-quinoline hydrochloride (commercially available from Zannan Pharma Ltd). Step 2 was performed by replacing 2,5-dichloro-phenol with 3-chloro-4-fluoro-phenol ([CAS RN 2613-23-2]) and conducting microwave heating at 180° C. for 1 h followed by 150° C. for 3 h. MS (ISP): 400.7 [M+H]⁺.

Example 104

[3-(3-Chloro-4-fluoro-phenoxy)-pyridin-4-yl]-(6-fluoro-3,4-dihydro-2H-quinolin-1-yl)-methanone

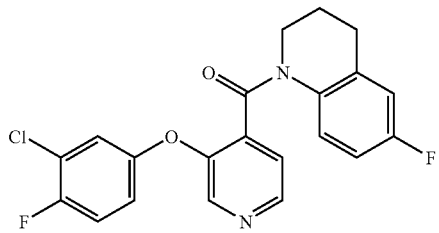

The title compound was prepared in analogy to Example 89, Step 1, replacing 1,2,3,4-tetrahydro-quinoline with 6-fluoro-1,2,3,4-tetrahydro-quinoline ([CAS RN 59611-52-8]). Step 2 was performed by replacing 2,5-dichloro-phenol with 3-chloro-4-fluoro-phenol ([CAS RN 2613-23-2]) and conducting microwave heating at 180° C. for 1 h followed by 150° C. for 3 h. MS (ISP): 400.7 [M+H]⁺.

Example 105

[3-(3-Chloro-4-fluoro-phenoxy)-pyridin-4-yl]-(6,8-difluoro-3,4-dihydro-2H-quinolin-1-yl)-methanone

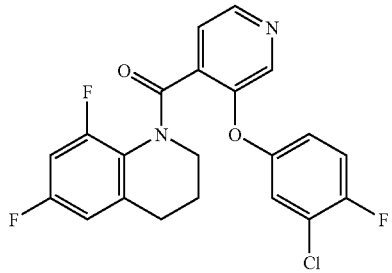

The title compound was prepared in analogy to Example 89, Step 1, replacing 1,2,3,4-tetrahydro-quinoline with 6,8-difluoro-1,2,3,4-tetrahydro-quinoline ([CAS RN 926218-72-6]). Step 2 was performed by replacing 2,5-dichloro-phenol with 3-chloro-4-fluoro-phenol ([CAS RN 2613-23-2]) and conducting microwave heating at 180° C. for 1 h followed by 150° C. for 3 h. MS (ISP): 418.7 [M+H]⁺.

Example 106

3-(3-Chloro-4-fluoro-phenoxy)-N-methyl-N-o-tolyl-isonicotinamide

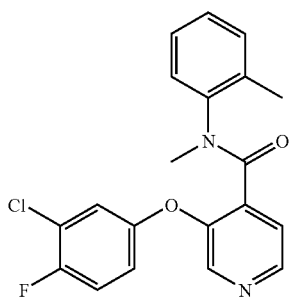

The title compound was prepared in analogy to Example 89, Step 1, replacing 1,2,3,4-tetrahydro-quinoline with methyl-o-tolyl-amine ([CAS RN 611-21-2]). Step 2 was performed by replacing 2,5-dichloro-phenol with 3-chloro-4- fluoro-phenol ([CAS RN 2613-23-2]) and conducting microwave heating at 180° C. for 1 h followed by 150° C. for 3 h. MS (ISP): 370.8 [M+H]+.

Example 107

3-(3-Chloro-4-fluoro-phenoxy)-N-(2-chloro-phenyl)-N-methyl-isonicotinamide

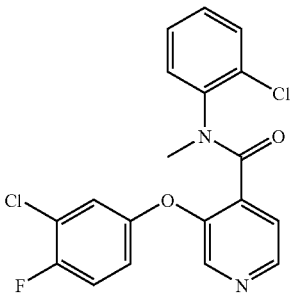

The title compound was prepared in analogy to Example 89, Step 1, replacing 1,2,3,4-tetrahydro-quinoline with (2-chloro-phenyl)-methyl-amine ([CAS RN 932-32-1]). Step 2 was performed by replacing 2,5-dichloro-phenol with 3-chloro-4-fluoro-phenol ([CAS RN 2613-23-2]) and conducting microwave heating at 180° C. for 1 h followed by 150° C. for 3 h. MS (ISP): 390.7 [M+H]+.

Example 108

3-(3-Chloro-4-fluoro-phenoxy)-N-(2-methoxy-phenyl)-N-methyl-isonicotinamide

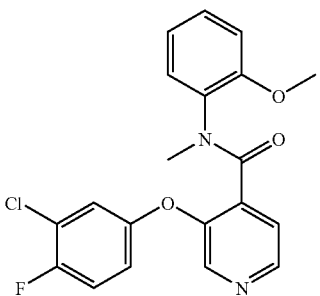

The title compound was prepared in analogy to Example 89, Step 1, replacing 1,2,3,4-tetrahydro-quinoline with (2-methoxy-phenyl)-methyl-amine ([CAS RN 10541-78-3]). Step 2 was performed by replacing 2,5-dichloro-phenol with 3-chloro-4-fluoro-phenol ([CAS RN 2613-23-2]) and conducting microwave heating at 180° C. for 1 h followed by 150° C. for 3 h. MS (ISP): 386.7 [M+H]+.

Example 109

3-(3-Chloro-4-fluoro-phenoxy)-N-(2-methoxy-pyridin-3-yl)-N-methyl-isonicotinamide

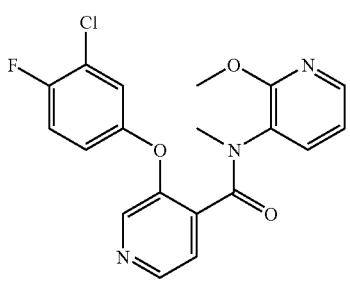

The title compound was prepared in analogy to Example 89, Step 1, replacing 1,2,3,4-tetrahydro-quinoline with 2-methoxy-pyridin-3-ylamine ([CAS RN 20265-38-7]). Step 2 was performed by replacing 2,5-dichloro-phenol with 3-chloro-4-fluoro-phenol ([CAS RN 2613-23-2]) and conducting microwave heating at 180° C. for 1 h followed by 150° C. for 3 h. MS (ISP): 387.7 [M+H]+.

Example 110

[2-(2,5-Dichloro-phenoxy)-phenyl]-(3,4-dihydro-2H-quinolin-1-yl)-methanone

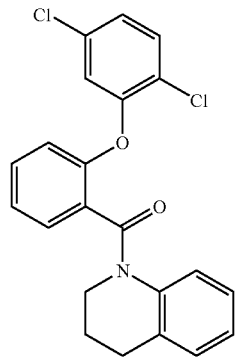

Step 1: 2-(2,5-Dichloro-phenoxy)-benzoic acid

To a solution of 2-iodo-benzoic acid (3.0 g, 12.10 mmol, 1.0 equiv; [CAS RN 88-67-5]) and 2,5-dichloro-phenol (1.97 g, 12.10 mmol, 1.0 equiv; [CAS RN 583-78-8]) in toluene (50 mL) was added caesium carbonate (7.88 g, 24.20 mmol, 2.0 equiv; [CAS RN 534-17-8]) and tetrakis(acetonitrile)copper (I) hexafluorophosphate (1.13 g, 3.02 mmol, 0.25 equiv; [CAS RN 64443-05-6]). The reaction mixture was heated to reflux over night. The solvent was evaporated under reduced pressure and the crude reaction product taken up in water (100 mL), acidified to pH 1 by addition of a solution of 1 M HCl and extracted with ethyl acetate (3×100 mL). The combined organic phases were dried over MgSO4 and the product purified by silica column chromatography using a MPLC system (CombiFlash Companion, Isco Inc.) eluting with a gradient of heptane (+1% acetic acid)/ethyl acetate affording 2.78 g (81%) of the title compound as a white solid. MS (ISN): 281.1 [M−H]−.

Step 2

To a solution of 2-(2,5-dichloro-phenoxy)-benzoic acid (50.0 mg, 0.177 mmol, 1.0 equiv) in anhydrous DMF (1 mL) was added N-ethyldiisopropylamine (114.4 mg, 151 μL, 0.89 mmol, 5.0 equiv; [CAS RN 7087-68-5]) and HATU (80.8 mg, 0.21 mmol, 1.2 equiv; [CAS RN 148893-10-1]). After stirring of the reaction mixture at 50° C. for 1 h, 1,2,3,4-tetrahydro-quinoline (28.3 mg, 27 μL, 0.21 mmol, 1.2 equiv; [CAS RN 635-46-1]) was added and stirring at 50° C. continued over night. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 12.9 mg (18%) of the title compound. MS (ISP): 398.2 [M+H]+.

Example 111

[2-(2,5-Dichloro-phenoxy)-phenyl]-(6,7-difluoro-3,4-dihydro-2H-quinolin-1-yl)-methanone

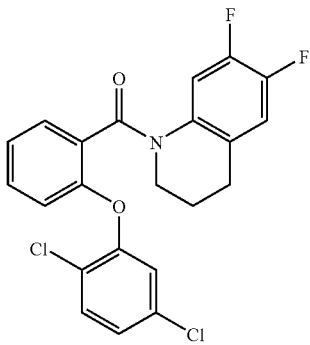

The title compound was prepared in analogy to Example 79 replacing 2-(3-chloro-4-fluoro-phenoxy)-nicotinic acid with 2-(2,5-dichloro-phenoxy)-benzoic acid (Example 110, Step 1). MS (ISP): 434.1 [M+H]$^+$.

Example 112

[2-(2,5-Dichloro-phenoxy)-phenyl]-(2-methyl-2,3-dihydro-indol-1-yl)-methanone

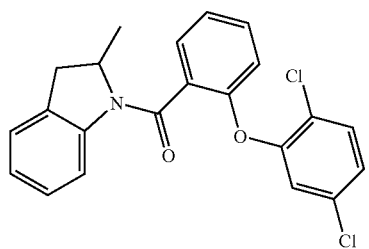

The title compound was prepared in analogy to Example 31, Step 2, replacing 2-(2,5-dichloro-phenoxy)-nicotinic acid with 2-(2,5-dichloro-phenoxy)-benzoic acid (Example 110, Step 1) and 6-methyl-1,2,3,4-tetrahydro-quinoline with 2-methyl-2,3-dihydro-1H-indole ([CAS RN 6872-06-6]). MS (ISP): 398.2 [M+H]$^+$.

Example 113

[2-(2,5-Dichloro-phenoxy)-5-fluoro-phenyl]-(3,4-dihydro-2H-quinolin-1-yl)-methanone

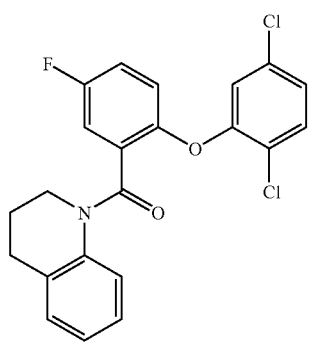

Step 1: 2-(2,5-Dichloro-phenoxy)-5-fluoro-benzoic acid 2-(2,5-Dichloro-phenoxy)-5-fluoro-benzoic acid was prepared in analogy to Example 76, Step 1, replacing 2-chloro-nicotinic acid with 2-bromo-5-fluoro-benzoic acid ([CAS RN 394-28-5]). MS (ISN): 299.0 [M−H]$^−$.

Step 2

The title compound was prepared in analogy to Example 110, Step 2, replacing 2-(2,5-dichloro-phenoxy)-benzoic acid (Example 110, Step 1) with 2-(2,5-dichloro-phenoxy)-5-fluoro-benzoic acid and 6-fluoro-1,2,3,4-tetrahydro-quinoline with 1,2,3,4-tetrahydro-quinoline ([CAS RN 635-46-1]). MS (ISP): 416.1 [M+H]$^+$.

Example 114

[2-(2,5-Dichloro-phenoxy)-5-fluoro-phenyl]-(2-methyl-3,4-dihydro-2H-quinolin-1-yl)-methanone

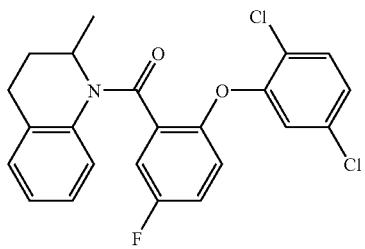

To a solution of 2-(2,5-dichloro-phenoxy)-5-fluoro-benzoic acid (36.1 mg, 0.12 mmol, 1.0 equiv; Example 113, Step 1) in dichloromethane (1 mL) was added 2-methyl-1,2,3,4-tetrahydro-quinoline (21.2 mg, 0.14 mmol, 1.2 equiv; [CAS RN 1780-19-4]), tri-n-butylamine (111.2 mg, 143 µL, 0.60 mmol, 5.0 equiv; [CAS RN 102-82-9]) and 2-chloro-1-methylpyridinium iodide (36.8 mg, 0.14 mmol, 1.2 equiv; [CAS RN 14338-32-0]). The reaction mixture was heated to 40° C. over night. Removal of the solvent mixture under reduced pressure and purification by preparative HPLC on reversed phase (Xterra® PrepMSC 18, 5 µM, 19×50 mm column equipped with a Gilson Liquid Handler 215 autosampler, two Rainin Dynamax® SD-300 pumps, a Sedex ELSD 75 light-scatter and a Dionex UVD 340S UV detector) eluting with a gradient of acetonitrile/water provided 7.8 mg (15%) of the title compound. MS (ISP): 430.1 [M+H]$^+$.

Example 115

[2-(2,5-Dichloro-phenoxy)-5-fluoro-phenyl]-(8-methyl-3,4-dihydro-2H-quinolin-1-yl)-methanone

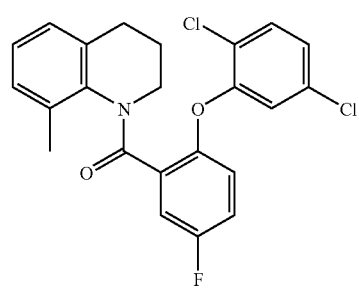

The title compound was prepared in analogy to Example 114 replacing 2-methyl-1,2,3,4-tetrahydro-quinoline with 8-methyl-1,2,3,4-tetrahydro-quinoline ([CAS RN 52601-70-4]). MS (ISP): 430.0 [M+H]⁺.

Example 116

[2-(2,5-Dichloro-phenoxy)-5-fluoro-phenyl]-(6-methyl-3,4-dihydro-2H-quinolin-1-yl)-methanone

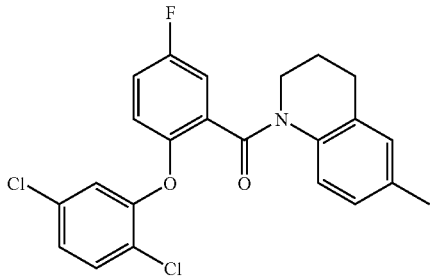

The title compound was prepared in analogy to Example 114 replacing 2-methyl-1,2,3,4-tetrahydro-quinoline with 6-methyl-1,2,3,4-tetrahydro-quinoline ([CAS RN 91-61-2]). MS (ISP): 430.1 [M+H]⁺.

Example 117

[2-(2,5-Dichloro-phenoxy)-5-fluoro-phenyl]-(2,3-dihydro-benzo[1,4]oxazin-4-yl)-methanone

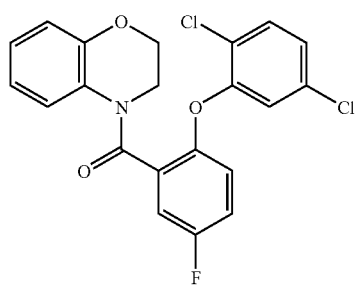

The title compound was prepared in analogy to Example 114 replacing 2-methyl-1,2,3,4-tetrahydro-quinoline with 3,4-dihydro-2H-benzo[1,4]oxazine ([CAS RN 5735-53-5]). MS (ISP): 418.0 [M+H]⁺.

Example 118

2-(2,5-Dichloro-phenoxy)-5-fluoro-N-methyl-N-phenyl-benzamide

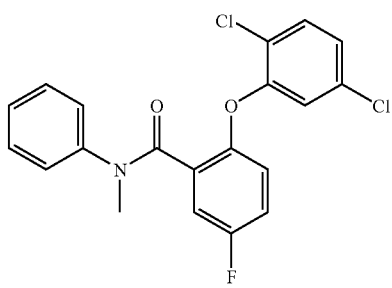

The title compound was prepared in analogy to Example 114 replacing 2-methyl-1,2,3,4-tetrahydro-quinoline with methyl-phenyl-amine ([CAS RN 100-61-8]). MS (ISP): 390.0 [M+H]⁺.

Example 119

4-(2,5-Dichloro-phenoxy)-3-(3,4-dihydro-2H-quinoline-1-carbonyl)-benzo nitrile

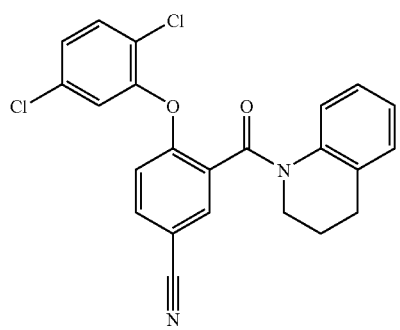

Step 1: 4-Bromo-3-(3,4-dihydro-2H-quinoline-1-carbonyl)-benzonitrile

To a solution of 2-bromo-5-cyano-benzoic acid (0.50 g, 2.12 mmol, 1.0 equiv; [CAS RN 845616-12-8]) in dichloromethane (5 mL) was added 1,2,3,4-tetrahydro-quinoline (0.35 g, 330 μL, 2.66 mmol, 1.2 equiv; [CAS RN 635-46-1]), N-ethyldiisopropylamine (1.43 g, 1.88 mL, 11.06 mmol, 5.0 equiv; [CAS RN 7087-68-5]) and 2-chloro-1-methylpyridinium iodide (0.68 g, 2.66 mmol, 1.2 equiv; [CAS RN 14338-32-0]). The reaction mixture was stirred at rt over the weekend. To the residue was added a sat. solution of NaHCO₃ (100 mL) and the solution extracted with dichloromethane (3×50 mL). The combined organic phases were dried over Na₂SO₄ and the product purified by silica column chromatography using a MPLC system (CombiFlash Companion, Isco Inc.) eluting with a gradient of toluene/acetone affording 0.35 g (46%) of the title compound as a light yellow solid. MS (ISP): 341.1 [M+H]⁺.

Step 2

To a solution of 4-bromo-3-(3,4-dihydro-2H-quinoline-1-carbonyl)-benzonitrile (100 mg, 0.44 mmol, 1.0 equiv) and 2,4-dichloro-phenol (72 mg, 0.44 mmol, 1.0 equiv; [CAS RN 120-83-2]) in toluene (1 mL) was added caesium carbonate (289 mg, 0.89 mmol, 2.0 equiv; [CAS RN 534-17-8]) and tetrakis(acetonitrile)copper(I) hexafluorophosphate (41 mg, 0.11 mmol, 0.25 equiv; [CAS RN 64443-05-6]). The reaction mixture was heated by microwave irradiation to 120° C. for 3 h. Removal of the solvent under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient

Example 120

[2-(2,5-Dichloro-phenoxy)-phenyl]-(8-fluoro-6-methyl-3,4-dihydro-2H-quinolin-1-yl)-methanone

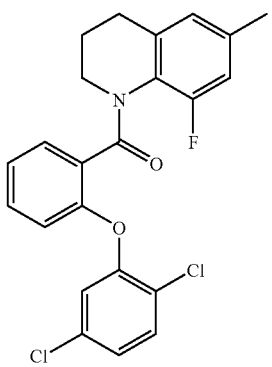

To a solution of 2-(2,5-dichloro-phenoxy)-benzoic acid (51.0 mg, 0.18 mmol, 1.0 equiv; Example 110, Step 1) in dichloromethane (2 mL) was added 8-fluoro-6-methyl-1,2,3,4-tetrahydro-quinoline (35.7 mg, 0.22 mmol, 1.2 equiv; [CAS RN 954260-80-1]), triethylamine (36.5 mg, 50 μL, 0.36 mmol, 2.0 equiv; [CAS RN 121-44-8]) and 2-chloro-1-methylpyridinium iodide (57.8 mg, 0.22 mmol, 1.2 equiv; [CAS RN 14338-32-0]). The reaction mixture was stirred at rt for 2 h. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 20.7 mg (27%) of the title compound. MS (ISP): 430.2 [M+H]$^+$.

Example 121

[2-(2,5-Dichloro-phenoxy)-phenyl]-(6,8-difluoro-3,4-dihydro-2H-quinolin-1-yl)-methanone

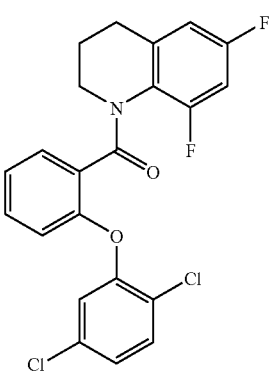

The title compound was prepared in analogy to Example 120 replacing 8-fluoro-6-methyl-1,2,3,4-tetrahydro-quinoline with 6,8-difluoro-1,2,3,4-tetrahydro-quinoline ([CAS RN 926218-72-6]). MS (ISP): 434.2 [M+H]$^+$.

Example 122

[2-(2,5-Dichloro-phenoxy)-pyridin-3-yl]-(3,4-dihydro-2H-quinoxalin-1-yl)-methanone

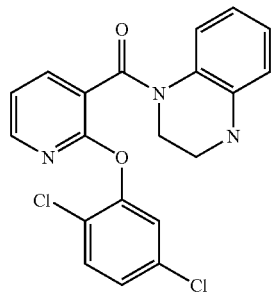

A solution of 2-(2,5-dichloro-phenoxy)-nicotinic acid (100 mg, 0.35 mmol, 1.0 equiv; Example 31, Step 1) in thionyl chloride (3.28 g, 2 ml, 27.6 mmol, 230 equiv; [CAS RN 7719-09-7]) was heated to 100° C. for 1 h. The reaction mixture was concentrated under reduced pressure, remaining thionyl chloride removed by azotropic distillation with toluene and the residue dissolved in anhydrous DMF (1 mL). To this solution was added N-ethyldiisopropylamine (452 mg, 595 μL, 3.5 mmol, 10.0 equiv; [CAS RN 7087-68-5]) and 1,2,3,4-tetrahydro-quinoxaline (56 mg, 0.42 mmol, 1.2 equiv; [CAS RN 3476-89-9]) and the reaction mixture was stirred at rt for 2 h. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 17.3 mg (12%) of the title compound. MS (ISP): 400.0 [M+H]$^+$.

Example 123

[2-(2,5-Dichloro-phenoxy)-pyridin-3-yl]-(4-methyl-3,4-dihydro-2H-quinoxalin-1-yl)-methanone

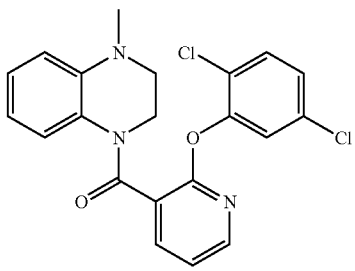

To a solution of 2-(2,5-dichloro-phenoxy)-nicotinic acid (42.6 mg, 0.15 mmol, 1.0 equiv; Example 31, Step 1) in anhydrous DMF (1 mL) was added 1-methyl-1,2,3,4-tetrahydro-quinoxaline (26.7 mg, 0.18 mmol, 1.2 equiv; [CAS RN 36438-97-8]), N-ethyldiisopropylamine (97 mg, 131 μL, 0.75 mmol, 5.0 equiv; [CAS RN 7087-68-5]) and HATU (68 mg, 0.18 mmol, 1.2 equiv; [CAS RN 148893-10-1]). The reaction mixture was heated by microwave irradiation to 100° C. for 30 min. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 15.6 mg (25%) of the title compound. MS (ISP): 413.9 [M+H]+.

Example 124

[2-(2,5-Dichloro-phenoxy)-pyridin-3-yl]-(4-isopropyl-3,4-dihydro-2H-quinoxalin-1-yl)-methanone

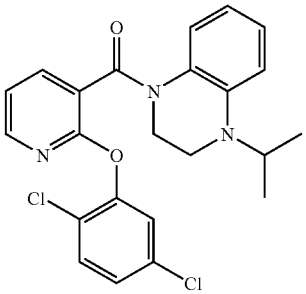

The title compound was prepared in analogy to Example 70 replacing 8-methoxy-1,2,3,4-tetrahydro-quinoline with 1-isopropyl-1,2,3,4-tetrahydro-quinoxaline oxalate (commercially available from Zannan Pharma Ltd). MS (ISP): 442.0 [M+H]+.

Example 125

(4-Cyclopropyl-3,4-dihydro-2H-quinoxalin-1-yl)-[2-(2,5-dichloro-phenoxy)-pyridin-3-yl]-methanone

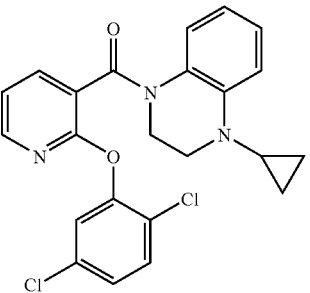

Step 1: Cyclopropyl-(2-nitro-phenyl)-amine

To cyclopropylamine (27.3 g, 33.1 mL, 0.48 mol, 2.25 equiv; [CAS RN 765-30-0]) was added dropwise 2-fluoronitrobenzene (30.0 g, 0.21 mol, 1.0 equiv; [CAS RN 1493-27-2]) over 1 h at 30° C. and stirring of the reaction mixture continued at rt for 18 h. The reaction mixture was extraction from a sat. solution of NaHCO$_3$ (500 mL) with ethyl acetate (3×300 mL) and the combined organic phases dried over MgSO$_4$. Purification by silica column chromatography using a MPLC system (CombiFlash Companion, Isco Inc.) eluting with a mixture of heptane/ethylacetate (9:1) afforded 32.4 g (86%) of the title compound as a yellow oil. MS (ISP): 178.0 [M+H]+.

Step 2: N-Cyclopropyl-N-(2-nitro-phenyl)-oxalamic acid methyl ester

To a solution of cyclopropyl-(2-nitro-phenyl)-amine (32.0 g, 0.18 mol, 1.0 equiv) in dichloromethane (320 mL) was added triethylamine (18.2 g, 25.0 mL, 0.18 mol, 1.0 equiv; [CAS RN 121-44-8]) and methyl oxalyl chloride (22.0 g, 16.5 mL, 0.18 mol, 1.0 equiv; [CAS RN 5781-53-3]) slowly at 0° C. After the addition was completed the reaction mixture was stirred at rt for 72 h. The reaction mixture was extraction from a sat. solution of NaHCO$_3$ (300 mL) with dichloromethane (3×200 mL) and the combined organic phases dried over MgSO$_4$. Purification by silica column chromatography using a MPLC system (CombiFlash Companion, Isco Inc.) eluting with a mixture of heptane/ethyl acetate (2:1) afforded 45.2 g (95%) of the title compound as a white solid. MS (ISP): 265.1 [M+H]+.

Step 3: 1-Cyclopropyl-4-hydroxy-1,4-dihydro-quinoxaline-2,3-dione

To a solution of N-cyclopropyl-N-(2-nitro-phenyl)-oxalamic acid methyl ester (45.0 g, 0.17 mol, 1.0 equiv) in methanol (400 mL) was added palladium on carbon (4.52 g, 0.0043 mol, 0.025 equiv; 10% Pd/C; [CAS RN 7440-05-3]) and the reaction mixture stirred under an atmosphere of hydrogen (1.2 bar) at rt for 2 h. The reaction mixture was diluted with ethyl acetate (400 mL), filtered over Celite® and the solvent mixture removed by evaporation under reduced pressure to give 31.2 g (84%) of the title compound as a light yellow solid. MS (ISN): 219.1 [M+H]+.

Step 4: 1-Cyclopropyl-1,4-dihydro-quinoxaline-2,3-dione

To a solution of 1-cyclopropyl-4-hydroxy-1,4-dihydroquinoxaline-2,3-dione (31.0 g, 0.14 mol, 1.0 equiv) in DMF (250 mL) was added triphenylphosphine (55.9 g, 0.21 mol, 1.5 equiv; [CAS RN 603-35-0]) and the reaction mixture stirred at 135° C. for 4 h. The reaction mixture was cooled down to 0° C. and dichloromethane (400 mL) was added. The suspension was stirred for 30 min, filtered and washed with dichloromethane (200 mL) providing 23.8 g (83%) of the title compound as a white solid. MS (ISN): 203.1 [M+H]+.

Step 5: 1-Cyclopropyl-1,2,3,4-tetrahydro-quinoxaline

To a stirred suspension of 1-cyclopropyl-1,4-dihydro-quinoxaline-2,3-dione (10.0 g, 49.45 mmol, 1.0 equiv) in THF (500 mL) was added dropwise a 1 M solution of borane-tetrahydrofurane complex (108.8 mL, 108.8 mmol, 2.2 equiv; [CAS RN 14044-65-6]) and the reaction mixture stirred at rt over night. The solvent was removed by evaporation under reduced pressure and the crude reaction mixture extracted from a sat. solution of NaHCO$_3$ (100 mL) with ethyl acetate (3×100 mL). The combined organic phases were dried over Na$_2$SO$_4$ and purified by silica column chromatography using a MPLC system (CombiFlash Companion, Isco Inc.) eluting with a gradient of heptane/ethyl acetate to give 4.2 g (49%) of the title compound as a light yellow solid. MS (ISP): 175.4 [M+H]+.

Step 6

To a solution of 2-(2,5-dichloro-phenoxy)-nicotinic acid (70 mg, 0.25 mmol, 1.0 equiv; Example 31, Step 1) in anhydrous DMF (1.4 mL) was added N-ethyldiisopropylamine (96 mg, 126 µL, 0.74 mmol, 3.0 equiv; [CAS RN 7087-68-5]) and HATU (112 mg, 0.30 mmol, 1.2 equiv; [CAS RN 148893-10-1]) and the reaction mixture stirred at rt. After 15 min, 1-cyclopropyl-1,2,3,4-tetrahydro-quinoxaline (52 mg, 0.30 mmol, 1.2 equiv) was added and stirring at rt continued over night. Purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 38 mg (35%) of the title compound. MS (ISP): 440.1 [M+H]+.

Example 126

(4-Cyclobutyl-3,4-dihydro-2H-quinoxalin-1-yl)-[2-(2,5-dichloro-phenoxy)-pyridin-3-yl]-methanone

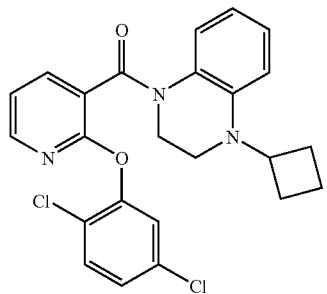

To a solution of [2-(2,5-dichloro-phenoxy)-pyridin-3-yl]-(3,4-dihydro-2H-quinoxalin-1-yl)-methanone (50 mg, 0.125 mmol, 1.0 equiv; Example 122) in cyclobutanone (469 mg, 0.5 mL, 6.69 mmol, 53.5 equiv; [CAS RN 1191-95-3]) was added acetic acid (28 mg, 27 µL, 0.5 mmol, 4.0 equiv; [CAS RN 64-19-7]) and the reaction mixture stirred at rt. After 90 min, sodium cyanoborohydride (15.7 mg, 0.25 mmol, 2.0 equiv; [CAS RN 25895-60-7]) was added and stirring at rt continued for 2 h. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 12.5 mg (22%) of the title compound. MS (ISP): 454.2 [M+H]+.

Example 127

[2-(2,5-Dichloro-phenoxy)-pyridin-3-yl]-(4-oxetan-3-yl-3,4-dihydro-2H-quinoxalin-1-yl)-methanone

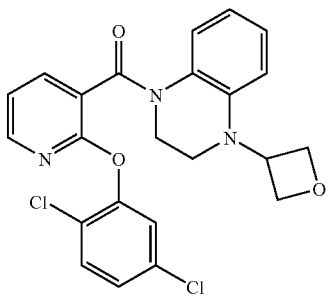

The title compound was prepared in analogy to Example 126 replacing cyclobutanone with oxetan-3-one ([CAS RN 6704-31-0]). MS (ISP): 456.2 [M+H]+.

Example 128

1-[2-(2,5-Dichloro-phenoxy)-pyridine-3-carbonyl]-2,3-dihydro-1H-quinolin-4-one

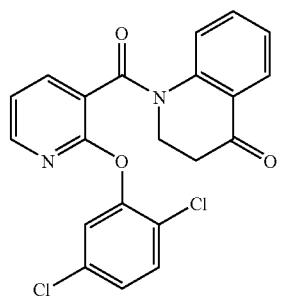

To a solution of [2-(2,5-dichloro-phenoxy)-pyridin-3-yl]-(3,4-dihydro-2H-quinolin-1-yl)-methanone (100 mg, 0.25 mmol, 1.0 equiv; Example 24) in anhydrous 1,2-dichloroethane (2 mL) was added sodium hydrogen carbonate (11 mg, 0.125 mmol, 0.5 equiv; [CAS RN 144-55-8]), tert-butyl hydroperoxide (189 mg, 227 µL, 1.25 mmol, 5.0 equiv, 5.5 M solution in decane; [CAS RN 75-91-2], TBHP) and dirhodium caprolactamate (1.7 mg, 0.0025 mmol, 0.01 equiv; [CAS RN 138984-26-6]; prepared according to M. P. Doyle, L. J. Westrum, W. N. E. Wolthuis, M. M. See, W. P. Boone, V. Bagheri, M. M. Pearson, *J. Am. Chem. Soc.* 1993, 115, 958-964). The reaction mixture was stirred at rt over night. Removal of the solvent mixture under reduced pressure and purification by silica column chromatography using a MPLC system (CombiFlash Companion, Isco Inc.) eluting with a gradient of heptane/ethyl acetate followed by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 59 mg (57%) of the title compound as a white solid. MS (ISP): 413.1 [M+H]+.

Example 129

[2-(2,5-Dichloro-phenoxy)-pyridin-3-yl]-(4-methylene-3,4-dihydro-2H-quinolin-1-yl)-methanone

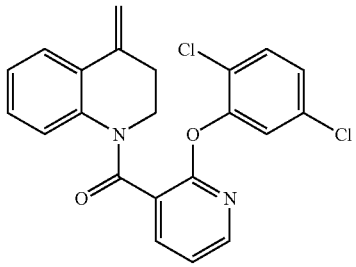

Step 1:
4-Methylene-3,4-dihydro-2H-quinoline-1-carboxylic acid tert-butyl ester A solution of methyltriphenylphosphonium bromide (1.92 g, 5.38 mmol, 1.1 equiv; [CAS RN 1779-49-3]) and potassium tert-butoxide (0.60 g, 5.38 mmol, 1.1 equiv; [CAS RN 865-47-4]) in toluene (20 mL) were heated to reflux. After 1 h, 4-oxo-3,4-dihydro-2H-quinoline-1-carboxylic acid tert-butyl ester (1.21 g, 4.89 mmol, 1.0 equiv; [CAS RN 179898-00-1]), dissolved in toluene (10 mL), was added and heating continued for one additional hour. The reaction mixture was extraction from a sat. solution of NH$_4$Cl (100 mL) with ethyl acetate (3×50 mL) and the combined organic phases dried over MgSO$_4$. Purification by silica column chromatography using a MPLC system (CombiFlash Companion, Isco Inc.) eluting with a gradient of heptane/ethyl acetate afforded 0.87 g (73%) of the title compound as a colorless oil. MS (ISP): 246.4 [M+H]$^+$.

Step 2

A solution of 4-methylene-3,4-dihydro-2H-quinoline-1-carboxylic acid tert-butyl ester (44.2 mg, 0.18 mmol, 1.2 equiv) in 4 M HCl in dioxane (4 mL) was stirred at rt for 2 h. The solvent was removed under reduced pressure and the crude product redissolved in anhydrous DMF (1 mL). To this solution was added 2-(2,5-dichloro-phenoxy)-nicotinic acid (42.6 mg, 0.15 mmol, 1.0 equiv; Example 31, Step 1), N-ethyldiisopropylamine (97 mg, 131 µL, 0.75 mmol, 5.0 equiv; [CAS RN 7087-68-5]) and HATU (68 mg, 0.18 mmol, 1.2 equiv; [CAS RN 148893-10-1]) and the reaction mixture heated by microwave irradiation to 100° C. for 30 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 4.1 mg (7%) of the title compound. MS (ISP): 410.7 [M+H]$^+$.

Example 130

[2-(2,5-Dichloro-phenoxy)-pyridin-3-yl]-[4-(3,3-difluoro-azetidin-1-yl)-3,4-dihydro-2H-quinolin-1-yl]-methanone

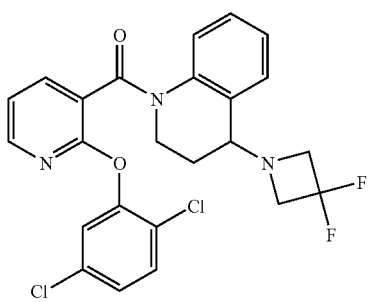

To a suspension of 1-[2-(2,5-dichloro-phenoxy)-pyridine-3-carbonyl]-2,3-dihydro-1H-quinolin-4-one (50 mg, 0.12 mmol, 1.0 equiv; Example 128) in ethanol (1.2 mL) was added 3,3-difluoroazetidine hydrochloride (31 mg, 0.24 mmol, 2.0 equiv; [CAS RN 288315-03-7]), acetic acid (27 mg, 26 µL, 0.48 mmol, 4.0 equiv; [CAS RN 64-19-7]) and N-ethyldiisopropylamine (31 mg, 42 µL, 0.24 mmol, 2.0 equiv; [CAS RN 7087-68-5]). The reaction mixture was heated by microwave irradiation to 100° C. for 10 min. Sodium triacetoxyborohydride (33 mg, 0.16 mmol, 1.3 equiv; [CAS RN 56553-60-7]) was added and heating at 100° C. continued for 15 min. The reaction mixture was extraction from a sat. solution of NaHCO$_3$ (50 mL) with ethyl acetate (3×50 mL) and the combined organic phases dried over MgSO$_4$. Purification by silica column chromatography using a MPLC system (CombiFlash Companion, Isco Inc.) eluting with a gradient of heptane/ethyl acetate afforded 0.04 g (7%) of the title compound as a light yellow solid. MS (ISP): 490.0 [M+H]$^+$.

Example 131

N-(2-Cyclopropyl-phenyl)-2-(2,5-dichloro-phenoxy)-N-methyl-nicotinamide

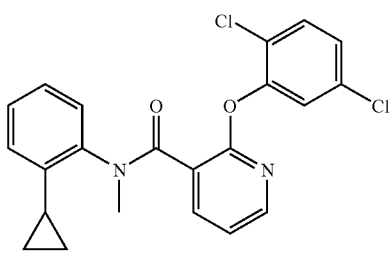

To a solution of 2-(2,5-dichloro-phenoxy)-nicotinic acid (42.6 mg, 0.15 mmol, 1.0 equiv; Example 31, Step 1) in anhydrous DMF (1 mL) was added N-ethyldiisopropylamine (97 mg, 128 µL, 0.75 mmol, 5.0 equiv; [CAS RN 7087-68-5]) and HATU (67 mg, 0.18 mmol, 1.2 equiv; [CAS RN 148893-10-1]) and the reaction mixture stirred at rt for 30 min. After addition of 2-cyclopropyl-phenylamine (24 mg, 0.18 mmol, 1.2 equiv; [CAS RN 3158-73-4]) the reaction mixture was heated by microwave irradiation to 100° C. After 30 min, sodium hydride (8.6 mg, 0.2 mmol, 2.0 equiv; 55% free-flowing powder moistened with oil; [CAS RN 7646-69-7]) and iodomethane (28.4 mg, 12 µL, 0.2 mmol, 2.0 equiv; [CAS RN 74-88-4]) were added and stirring of the reaction mixture at rt continued for 2 h. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 12.6 mg (20%) of the title compound. MS (ISP): 412.9 [M+H]$^+$.

Example 132

2-(2,5-Dichloro-phenoxy)-N-methyl-N-(2-methylsulfanyl-phenyl)-nicotinamide

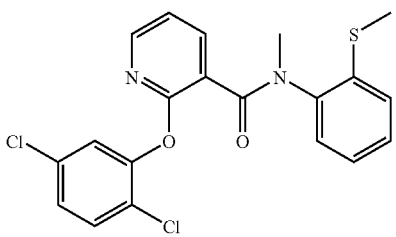

The title compound was prepared in analogy to Example 131 replacing 2-cyclopropyl-phenylamine with 2-methylsulfanyl-phenylamine ([CAS RN 2987-53-3]). MS (ISP): 418.9 [M+H]$^+$.

Example 133

2-(2,5-Dichloro-phenoxy)-N-methyl-N-[2-(2-methyl-2H-pyrazol-3-yl)-phenyl]-nicotinamide

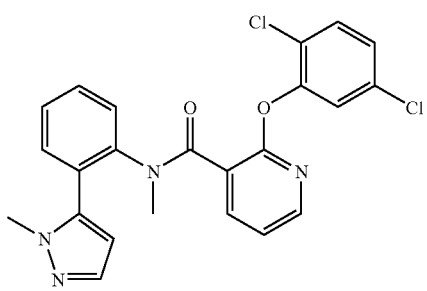

A solution of 2-(2,5-dichloro-phenoxy)-nicotinic acid (28.4 mg, 0.1 mmol, 1.0 equiv; Example 31, Step 1) in thionyl chloride (984 mg, 800 μL, 11.0 mmol, 110 equiv; [CAS RN 7719-09-7]) was heated to 100° C. for 1 h. The reaction mixture was concentrated under reduced pressure, remaining thionyl chloride removed by azotropic distillation with toluene and the residue dissolved in anhydrous DMF (1 mL). To this solution was added N-ethyldiisopropylamine (129 mg, 170 μL, 1.0 mmol, 10.0 equiv; [CAS RN 7087-68-5]) and 2-(2H-pyrazol-3-yl)-phenylamine (19 mg, 0.12 mmol, 1.2 equiv; [CAS RN 111562-32-4]) and the reaction mixture was stirred at rt for 18 h. To this solution was added sodium hydride (8.6 mg, 0.2 mmol, 2.0 equiv; 55% free-flowing powder moistened with oil; [CAS RN 7646-69-7]) and iodomethane (28.4 mg, 12 μL, 0.2 mmol, 2.0 equiv; [CAS RN 74-88-4]) and stirring of the reaction mixture at rt continued for 2 h. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 1.0 mg (2%) of the title compound. MS (ISP): 453.1 [M+H]⁺.

Example 134

N-(2-Amino-phenyl)-2-(2,5-dichloro-phenoxy)-N-methyl-nicotinamide

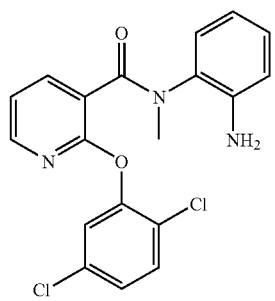

To a solution of 2-(2,5-dichloro-phenoxy)-nicotinic acid (50 mg, 0.18 mmol, 1.0 equiv; Example 31, Step 1) in anhydrous DMF (2 mL) was added N-ethyldiisopropylamine (116 mg, 154 μL, 0.90 mmol, 5.0 equiv; [CAS RN 7087-68-5]) and HATU (82 mg, 0.22 mmol, 1.2 equiv; [CAS RN 148893-10-1]) and the reaction mixture stirred at rt for 30 min. After addition of N-methyl-benzene-1,2-diamine (26.9 mg, 0.22 mmol, 1.2 equiv; [CAS RN 4760-34-3]) stirring was continued at rt for 90 min. Removal of the solvent under reduced pressure and purification by silica column chromatography using a MPLC system (CombiFlash Companion, Isco Inc.) eluting with a gradient of heptane/ethyl acetate afforded 33 mg (47%) of the title compound as a white solid. MS (ISP): 388.0 [M+H]⁺.

Example 135

2-(2,5-Dichloro-phenoxy)-N-(2,5-dichloro-phenyl)-N-methyl-nicotinamide

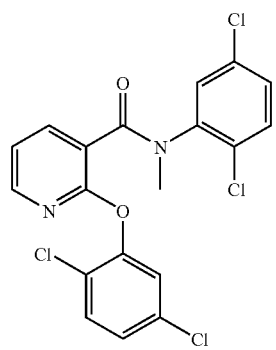

The title compound was prepared in analogy to Example 133 replacing 2-(2H-pyrazol-3-yl)-phenylamine with 2,5-dichloro-phenylamine ([CAS RN 95-82-9]). MS (ISP): 443.1 [M+H]⁺.

Example 136

[2-(2,5-Dichloro-phenoxy)-pyridin-3-yl]-(2,3,3a,4-tetrahydro-1H-pyrrolo[1,2-a]quinoxalin-5-yl)-methanone

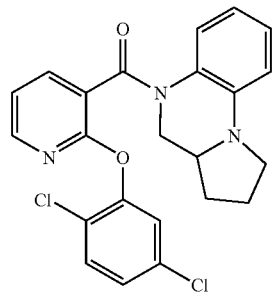

To a solution of 4,5-dihydro-pyrrolo[1,2-α]quinoxaline (30.6 mg, 0.18 mmol, 1.2 equiv; [CAS RN 56721-86-9]) in ethanol (5 mL) was added palladium on carbon (3.2 mg, 0.003 mmol, 0.02 equiv; 10% Pd/C; [CAS RN 7440-05-3]) and the reaction mixture stirred under an atmosphere of hydrogen (3 bar) at rt for 4 h. The reaction mixture was concentrated under reduced pressure, filtered over Celite® and the remaining residue redissolved in anhydrous DMF (1 mL). To this solution was added N-ethyldiisopropylamine (64 mg, 86 µL, 0.50 mmol, 5.0 equiv; [CAS RN 7087-68-5]) and 2-(2,5-dichloro-phenoxy)-nicotinoylchloride (45.4 mg, 0.15 mmol, 1.0 equiv; prepared according to Example 122) and the reaction mixture stirred at rt over night. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 21.4 mg (32%) of the title compound. MS (ISP): 440.1 [M+H]+.

Example 137

[2-(2,5-Dichloro-phenoxy)-pyridin-3-yl]-(4-isobutyl-3,4-dihydro-2H-quinoxalin-1-yl)-methanone

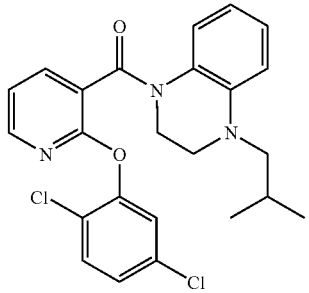

To a solution of [2-(2,5-dichloro-phenoxy)-pyridin-3-yl]-(3,4-dihydro-2H-quinoxalin-1-yl)-methanone (24 mg, 0.06 mmol, 1.0 equiv; Example 122) in anhydrous DMF (1 mL) was added 2-methyl-propionaldehyde (17.3 mg, 22 µL, 0.24 mmol, 4.0 equiv; [CAS RN 78-84-2]), dibutyltin dichloride (1.8 mg, 0.006 mmol, 0.1 equiv; [CAS RN 683-18-1]) and phenylsilane (13.0 mg, 15 µL, 0.12 mmol, 2.0 equiv; [CAS RN 694-53-1]). The reaction mixture was heated by microwave irradiation to 150° C. for 15 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 10.3 mg (38%) of the title compound as a light yellow powder. MS (ISP): 456.4 [M+H]+.

Example 138

(4-Cyclopropylmethyl-3,4-dihydro-2H-quinoxalin-1-yl)-[2-(2,5-dichloro-phenoxy)-pyridin-3-yl]-methanone

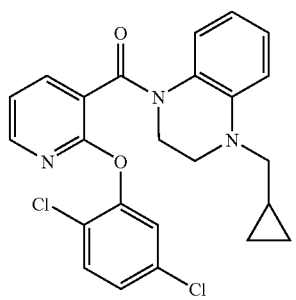

The title compound was prepared in analogy to Example 137 replacing 2-methyl-propionaldehyde with cyclopropanecarbaldehyde ([CAS RN 1489-69-6]). MS (ISP): 454.0 [M+H]+.

Example 139

(4-Cyclobutylmethyl-3,4-dihydro-2H-quinoxalin-1-yl)-[2-(2,5-dichloro-phenoxy)-pyridin-3-yl]-methasone

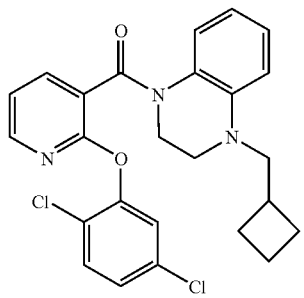

The title compound was prepared in analogy to Example 137 replacing 2-methyl-propionaldehyde with cyclobutanecarbaldehyde ([CAS RN 2987-17-9]). MS (ISP): 468.3 [M+H]+.

Example 140

Acetic acid 2-{4-[2-(2,5-dichloro-phenoxy)-pyridine-3-carbonyl]-3,4-dihydro-2H-quinoxalin-1-yl}-ethyl ester

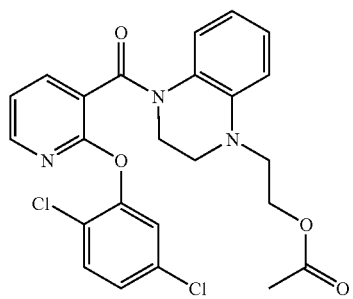

To a solution of [2-(2,5-dichloro-phenoxy)-pyridin-3-yl]-(3,4-dihydro-2H-quinoxalin-1-yl)-methanone (24 mg, 0.06 mmol, 1.0 equiv; Example 122) in anhydrous DMF (1 mL) was added lithium aluminum hydride (2.3 mg, 0.06 mmol, 1.0 equiv; [CAS RN 16853-85-3]) and the reaction mixture stirred at rt. After 30 min, acetic acid 2-bromo-ethyl ester (12.0 mg, 8 µL, 0.072 mmol, 1.2 equiv; [CAS RN 927-68-4]) was added and the reaction mixture heated by microwave irradiation to 180° C. for 60 min. Removal of the solvent mixture under reduced pressure and purification by preparative HPLC on reversed phase (Xterra® PrepMSC 18, 5 µM, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 8.9 mg (31%) of the title compound as a light yellow powder. MS (ISP): 486.1 [M+H]+.

Example 141

{4-[2-(2,5-Dichloro-phenoxy)-pyridine-3-carbonyl]-3,4-dihydro-2H-quinoxalin-1-yl}-acetic acid ethyl ester

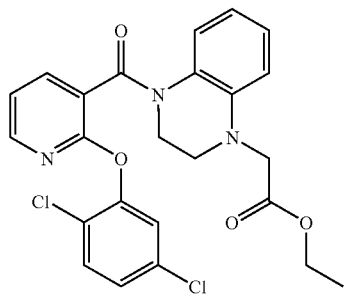

To a solution of [2-(2,5-dichloro-phenoxy)-pyridin-3-yl]-(3,4-dihydro-2H-quinoxalin-1-yl)-methanone (60 mg, 0.15 mmol, 1.0 equiv; Example 122) in anhydrous DMF (0.5 mL) was added N-ethyldiisopropylamine (96 mg, 129 µL, 0.75 mmol, 5.0 equiv; [CAS RN 7087-68-5]) and ethyl bromoacetate (55.1 mg, 37 µL, 0.33 mmol, 2.2 equiv; [CAS RN 105-36-2]) and the reaction mixture heated by microwave irradiation to 100° C. for 2 h. Removal of the solvent under reduced pressure and purification by preparative HPLC on reversed phase (Xterra® PrepMSC 18, 5 µM, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 42.7 mg (62%) of the title compound as a light yellow powder. MS (ISP): 486.1 [M+H]$^+$.

Example 142

{4-[2-(2,5-Dichloro-phenoxy)-pyridine-3-carbonyl]-3,4-dihydro-2H-quinoxalin-1-yl}-acetic acid

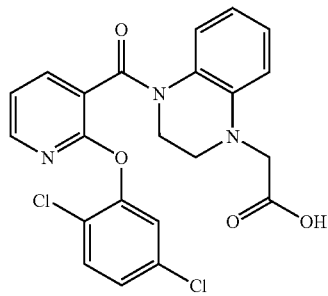

To a solution of [2-(2,5-dichloro-phenoxy)-pyridin-3-yl]-(3,4-dihydro-2H-quinoxalin-1-yl)-methanone (30 mg, 0.075 mmol, 1.0 equiv; Example 122) in anhydrous DMF (0.5 mL) was added N-ethyldiisopropylamine (48 mg, 65 µL, 0.375 mmol, 5.0 equiv; [CAS RN 7087-68-5]) and ethyl bromoacetate (27.6 mg, 19 µL, 0.165 mmol, 2.2 equiv; [CAS RN 105-36-2]) and the reaction mixture heated by microwave irradiation to 100° C. After 2 h, a 5 M solution of sodium hydroxide (0.5 mL, 2.5 mmol, 33 equiv; [CAS RN 1310-73-2]) was added and the reaction mixture stirred at rt over night. Removal of the solvent under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 7.5 mg (22%) of the title compound as a light yellow powder. MS (ISP): 458.1 [M+H]$^+$.

Example 143

3-(4-{4-[2-(2,5-Dichloro-phenoxy)-pyridine-3-carbonyl]-3,4-dihydro-2H-quinoxaline-1-sulfonyl}-phenyl)-propionic acid

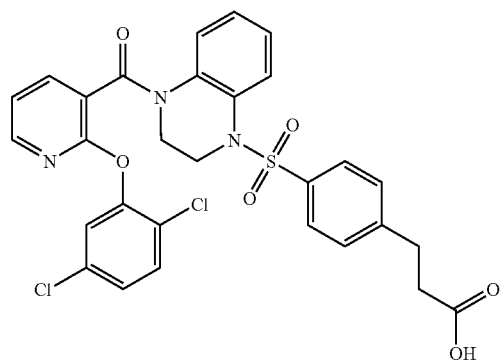

Step 1: 3-(4-{-4-[2-(2,5-Dichloro-phenoxy)-pyridine-3-carbonyl]-3,4-dihydro-2H-quinoxaline-1-sulfonyl}-phenyl)-propionic acid methyl ester To a solution of [2-(2,5-dichloro-phenoxy)-pyridin-3-yl]-(3,4-dihydro-2H-quinoxalin-1-yl)-methanone (80 mg, 0.2 mmol, 1.0 equiv; Example 122) in anhydrous dichloromethane (2 mL) was added N-ethyldiisopropylamine (51.3 mg, 69 µL, 0.4 mmol, 2.0 equiv; [CAS RN 7087-68-5]) and methyl 3-(4-chlorosulphonyl)phenylproprionate (57.8 mg, 0.22 mmol, 1.1 equiv; [CAS RN 374537-95-8]) and the reaction mixture stirred at rt over night. Removal of the solvent under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 44 mg (35%) of the title compound as a light off-white powder. MS (ISP): 626.2 [M+H]$^+$.

Step 2

To a suspension of 3-(4-{4-[2-(2,5-dichloro-phenoxy)-pyridine-3-carbonyl]-3,4-dihydro-2H-quinoxaline-1-sulfonyl}-phenyl)-propionic acid methyl ester (36 mg, 0.058 mmol, 1.0 equiv) in ethanol (1 mL) was added a 1 M solution of sodium hydroxide (120 µL, 0.12 mmol, 2.0 equiv; [CAS RN 1310-73-2]) and the reaction mixture stirred at rt over night. Removal of the solvent under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter

Example 144

(3,4-Dihydro-2H-quinolin-1-yl)-[2-(2-fluoro-5-trifluoromethyl-phenoxy)-pyridin-3-yl]-methanone

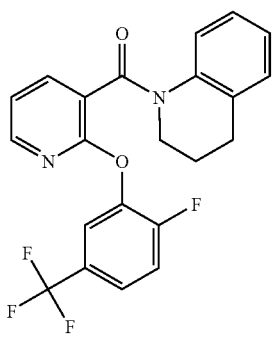

To a solution of (2-chloro-pyridin-3-yl)-(3,4-dihydro-2H-quinolin-1-yl)-methanone (50 mg, 0.18 mmol, 1.0 equiv; Example 6, Step 1) and 2-fluoro-5-trifluoromethyl-phenol (42.1 mg, 0.23 mmol, 1.3 equiv; [CAS RN 141483-15-0]) in anhydrous toluene (0.5 mL) was added caesium carbonate (176 mg, 0.54 mmol, 3.0 equiv; [CAS RN 534-17-8]) and tetrakis(acetonitrile)copper(I) hexafluorophosphate (20.1 mg, 0.054 mmol, 0.3 equiv; [CAS RN 64443-05-6]). The reaction mixture was heated by microwave irradiation to 150° C. for 1 h. Purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 50 mg (67%) of the title compound as a light yellow solid. MS (ISP): 417.4 [M+H]$^+$.

Example 145

2-(2,5-Dichloro-phenoxy)-5-fluoro-N-(2-methoxy-pyridin-3-yl)-N-methyl-nicotinamide

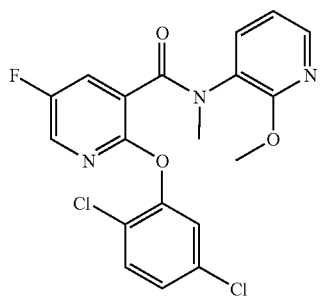

To a solution of 2-(2,5-dichloro-phenoxy)-5-fluoro-nicotinic acid (100 mg, 0.33 mmol, 1.0 equiv; Example 80, Step 1) in anhydrous DMF (1 mL) was added N-ethyldiisopropylamine (213 mg, 282 µL, 1.65 mmol, 5.0 equiv; [CAS RN 7087-68-5]) and HATU (151 mg, 0.40 mmol, 1.2 equiv; [CAS RN 148893-10-1]) and the reaction mixture stirred at rt. After 1 h, 3-amino-2-methoxypyridine (49 mg, 0.40 mmol, 1.2 equiv; [CAS RN 20265-38-7]) was added and stirring at rt continued over night. The reaction mixture was extracted from a sat. solution of NaHCO$_3$ (100 mL) with dichloromethane (3×50 mL), the combined organic phases dried over MgSO$_4$, the solvent removed by evaporation under reduced pressure and the crude reaction mixture redissolved in DMF (1.5 mL). To this solution was added sodium hydride (28.6 mg, 0.66 mmol, 2.0 equiv; 55% free-flowing powder moistened with oil; [CAS RN 7646-69-7]) and iodomethane (93.7 mg, 41 µL, 0.66 mmol, 2.0 equiv; [CAS RN 74-88-4]) and the reaction mixture stirred at rt for 30 min. Purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 28.5 mg (20%) of the title compound. MS (ISP): 422.0 [M+H]$^+$.

Example 146

N-(2,6-Dichloro-3-methoxy-phenyl)-2-(2,5-dichloro-phenoxy)-5-fluoro-N-methyl-nicotinamide

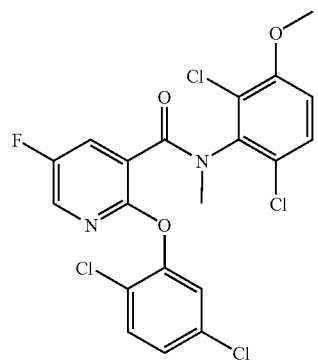

Step 1:
2-(2,5-Dichloro-phenoxy)-5-fluoro-nicotinoyl chloride

To a solution of 2-(2,5-dichloro-phenoxy)-5-fluoro-nicotinic acid (2.14 g, 7.08 mmol, 1.0 equiv; Example 80, Step 1) in dichloromethane (15 mL) was added thionyl chloride (16.4 g, 10 mL, 138 mmol, 19.5 equiv; [CAS RN 7719-09-7]) and the reaction mixture heated to reflux for 2 h. The reaction mixture was concentrated under reduced pressure and remaining thionyl chloride removed by azotropic distillation with toluene. The crude material was used in the consecutive reaction step without further purification.

Step 2

To a solution of 2-(2,5-dichloro-phenoxy)-5-fluoro-nicotinoyl chloride (76.6 mg, 0.24 mmol, 1.0 equiv) in anhydrous DMF (1 mL) was added N-ethyldiisopropylamine (155 mg, 205 µL, 1.2 mmol, 5.0 equiv; [CAS RN 7087-68-5]) and 2,6-dichloro-3-methoxy-phenylamine (50.7 mg, 0.264 mmol, 1.1 equiv; [CAS RN 55285-43-3]) and the reaction mixture stirred at rt over night. To this solution was added sodium hydride (20.6 mg, 0.48 mmol, 2.0 equiv; 55% free-flowing powder moistened with oil; [CAS RN 7646-69-7]) and iodomethane (68.2 mg, 29 μL, 0.48 mmol, 2.0 equiv; [CAS RN 74-88-4]) and stirring of the reaction mixture at rt continued for 2 h. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 8.1 mg (7%) of the title compound as an off-white powder. MS (ISP): 490.9 [M+H]+.

Example 147

[2-(2,5-Dichloro-phenoxy)-5-fluoro-pyridin-3-yl]-(3,4-dihydro-2H-quinoxalin-1-yl)-methanone

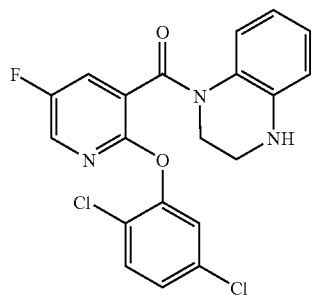

The title compound was prepared in analogy to Example 146, Step 2, replacing 2,6-dichloro-3-methoxy-phenylamine with 1,2,3,4-tetrahydro-quinoxaline ([CAS RN 3476-89-9]). MS (ISP): 418.3 [M+H]+.

Example 148

1-[2-(2,5-Dichloro-phenoxy)-5-fluoro-pyridine-3-carbonyl]-1,2,3,4-tetrahydro-quinoline-4-carboxylic acid methyl ester

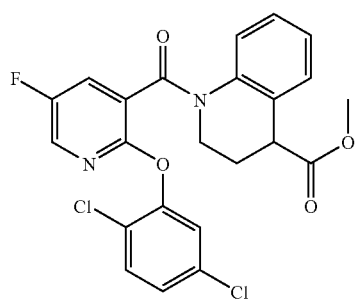

To a solution of 2-(2,5-dichloro-phenoxy)-5-fluoro-nicotinoyl chloride (48.1 mg, 0.15 mmol, 1.0 equiv; Example 146, Step 1) in anhydrous DMF (1 mL) was added N-ethyldiisopropylamine (97 mg, 128 μL, 0.75 mmol, 5.0 equiv; [CAS RN 7087-68-5]) and 1,2,3,4-tetrahydro-quinoline-4-carboxylic acid methyl ester (31.6 mg, 0.165 mmol, 1.1 equiv; [CAS RN 68066-85-3]) and the reaction mixture stirred at rt for 2 h. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 9.1 mg (13%) of the title compound as a light yellow solid. MS (ISP): 475.1 [M+H]+.

Example 149

1-[2-(2,5-Dichloro-phenoxy)-5-fluoro-pyridine-3-carbonyl]-1,2,3,4-tetrahydro-quinoline-4-carboxylic acid methyl ester

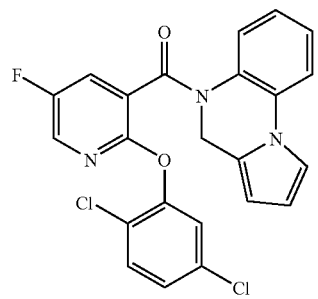

The title compound was prepared in analogy to Example 148 replacing 1,2,3,4-tetrahydro-quinoline-4-carboxylic acid methyl ester with 4,5-dihydro-pyrrolo[1,2-c]quinoxaline ([CAS RN 56721-86-9]). MS (ISP): 454.0 [M+H]+.

Example 150

(4-Cyclobutyl-3,4-dihydro-2H-quinoxalin-1-yl)-[2-(2,5-dichloro-phenoxy)-5-fluoro-pyridin-3-yl]-methanone

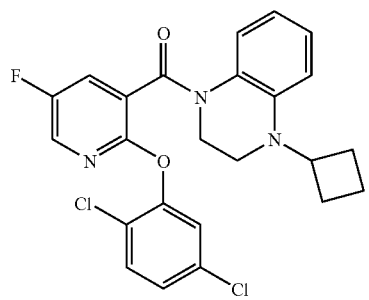

To a solution of [2-(2,5-dichloro-phenoxy)-5-fluoro-pyridin-3-yl]-(3,4-dihydro-2H-quinoxalin-1-yl)-methanone (52.3 mg, 0.125 mmol, 1.0 equiv; Example 147) in methanol (0.5 mL) was added cyclobutanone (188 mg, 0.2 mL, 2.68 mmol, 21.4 equiv; [CAS RN 1191-95-3]), acetic acid (28 mg, 27 μL, 0.5 mmol, 4.0 equiv; [CAS RN 64-19-7]) and the reaction mixture stirred at rt. After 90 min, sodium cyanoborohydride (15.7 mg, 0.25 mmol, 2.0 equiv; [CAS RN 25895-60-7]) was added and stirring at rt continued for 18 h. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 3.3 mg (6%) of the title compound. MS (ISP): 474.1 [M+H]+.

Example 151

[2-(2,5-Dichloro-phenoxy)-5-fluoro-pyridin-3-yl]-(4-furan-3-ylmethyl-3,4-dihydro-2H-quinoxalin-1-yl)-methanone

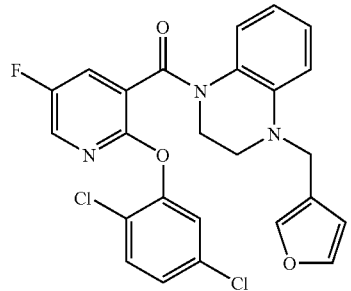

To a solution of [2-(2,5-dichloro-phenoxy)-5-fluoro-pyridin-3-yl]-(3,4-dihydro-2H-quinoxalin-1-yl)-methanone (25.1 mg, 0.06 mmol, 1.0 equiv; Example 148) in anhydrous DMF (1 mL) was added furan-3-carbaldehyde (23.1 mg, 20 µL, 0.24 mmol, 4.0 equiv; [CAS RN 498-60-2]), dibutyltin dichloride (1.8 mg, 0.006 mmol, 0.1 equiv; [CAS RN 683-18-1]) and phenylsilane (13.0 mg, 15 µL, 0.12 mmol, 2.0 equiv; [CAS RN 694-53-1]). The reaction mixture was heated by microwave irradiation to 150° C. for 15 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 5.4 mg (18%) of the title compound as a light yellow solid. MS (ISP): 498.3 [M+H]+.

Example 152

(4-Cyclobutylmethyl-3,4-dihydro-2H-quinoxalin-1-yl)-[2-(2,5-dichloro-phenoxy)-5-fluoro-pyridin-3-yl]-methanone

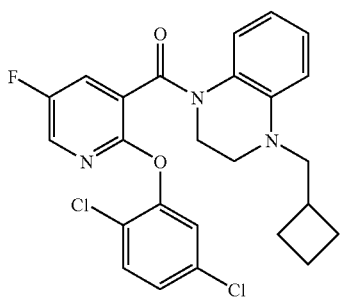

The title compound was prepared in analogy to Example 151 replacing furan-3-carbaldehyde with cyclobutanecarbaldehyde ([CAS RN 2987-17-9]). MS (ISP): 486.3 [M+H]+.

Example 153

[2-(2,5-Dichloro-phenoxy)-5-fluoro-pyridin-3-yl]-[4-(3,3,3-trifluoro-propyl)-3,4-dihydro-2H-quinoxalin-1-yl]-methanone

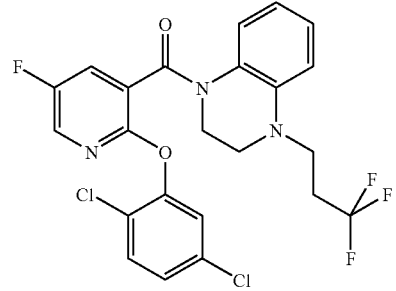

The title compound was prepared in analogy to Example 151 replacing furan-3-carbaldehyde with 3,3,3-trifluoro-propionaldehyde ([CAS RN 460-40-2]). MS (ISP): 486.3 [M+H]+.

Example 154

{4-[2-(2,5-Dichloro-phenoxy)-5-fluoro-pyridine-3-carbonyl]-3,4-dihydro-2H-quinoxalin-1-yl}-acetic acid ethyl ester

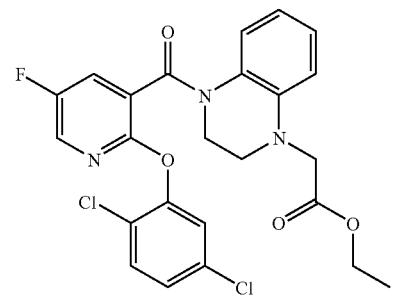

To [2-(2,5-dichloro-phenoxy)-5-fluoro-pyridin-3-yl]-(3,4-dihydro-2H-quinoxalin-1-yl)-methanone (200 mg, 0.478 mmol, 1.0 equiv; Example 147) was added a 50% solution of glyoxylic acid ethylester in toluene (1.03 g, 1 mL, 1.913 mmol, 4.0 equiv; [CAS RN 924-44-7]), dibutyltin dichloride (14.6 mg, 0.048 mmol, 0.1 equiv; [CAS RN 683-18-1]) and phenylsilane (103.8 mg, 118 µL, 0.956 mmol, 2.0 equiv; [CAS RN 694-53-1]). The reaction mixture was heated by microwave irradiation to 100° C. for 30 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/ water provided 82.7 mg (34%) of the title compound as a light yellow solid. MS (ISP): 504.3 [M+H]+.

Example 155

{4-[2-(2,5-Dichloro-phenoxy)-5-fluoro-pyridine-3-carbonyl]-3,4-dihydro-2H-quinoxalin-1-yl}-acetic acid

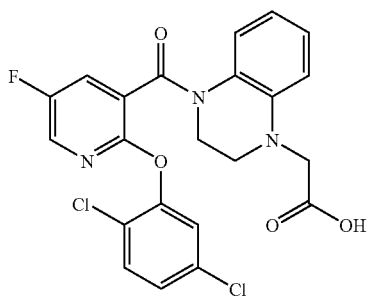

To a solution of {4-[2-(2,5-dichloro-phenoxy)-5-fluoro-pyridine-3-carbonyl]-3,4-dihydro-2H-quinoxalin-1-yl}-acetic acid ethyl ester (82 mg, 0.163 mmol, 1.0 equiv; Example 154) in THF (1 mL) was added a 5 M solution of sodium hydroxide (0.5 mL, 2.5 mmol, 15 equiv; [CAS RN 1310-73-2]) and the reaction mixture heated by microwave irradiation to 120° C. for 30 min. Removal of the solvent under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 7.5 mg (10%) of the title compound as a light yellow powder. MS (ISP): 476.0 [M+H]+.

Example 156

3-{4-[2-(2,5-Dichloro-phenoxy)-5-fluoro-pyridine-3-carbonyl]-3,4-dihydro-2H-quinoxalin-1-yl}-propionic acid ethyl ester

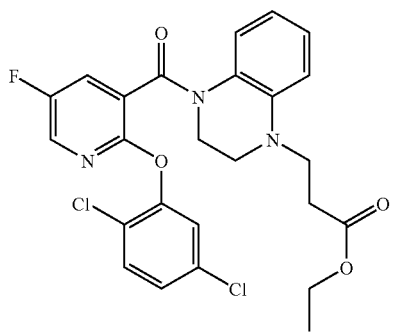

To a solution of [2-(2,5-dichloro-phenoxy)-5-fluoro-pyridin-3-yl]-(3,4-dihydro-2H-quinoxalin-1-yl)-methanone (25.1 mg, 0.06 mmol, 1.0 equiv; Example 147) in anhydrous DMF (1 mL) was added lithium aluminium hydride (2.3 mg, 0.06 mmol, 1.0 equiv; [CAS RN 16853-85-3]) and the reaction mixture stirred at rt. After 30 min, 3-bromo-propionic acid ethyl ester (13.0 mg, 10 µL, 0.072 mmol, 1.2 equiv; [CAS RN 539-74-2]) was added and the reaction mixture heated by microwave irradiation to 150° C. for 30 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 2.4 mg (8%) of the title compound as a light brown oil. MS (ISP): 518.3 [M+H]+.

Example 157

3-{4-[2-(2,5-Dichloro-phenoxy)-5-fluoro-pyridine-3-carbonyl]-3,4-dihydro-2H-quinoxalin-1-yl}-2-methyl-propionic acid

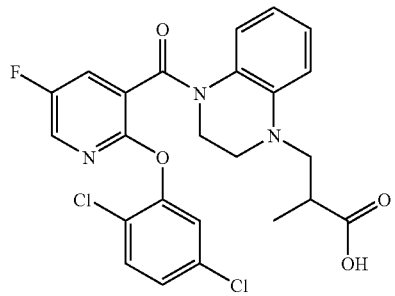

To a solution of [2-(2,5-dichloro-phenoxy)-5-fluoro-pyridin-3-yl]-(3,4-dihydro-2H-quinoxalin-1-yl)-methanone (25.1 mg, 0.06 mmol, 1.0 equiv; Example 147) in a 1:1 mixture of THF and water (1 mL) was added 2-methyl-3-oxo-propionic acid methyl ester (27.9 mg, 0.24 mmol, 4.0 equiv; [CAS RN 51673-64-4]), dibutyltin dichloride (1.8 mg, 0.006 mmol, 0.1 equiv; [CAS RN 683-18-1]) and phenylsilane (13.0 mg, 15 µL, 0.12 mmol, 2.0 equiv; [CAS RN 694-53-1]). The reaction mixture was heated by microwave irradiation to 150° C. for 1.5 h. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 2.2 mg (7%) of the title compound as a light yellow solid. MS (ISP): 504.0 [M+H]+.

Example 158

4-{4-[2-(2,5-Dichloro-phenoxy)-5-fluoro-pyridine-3-carbonyl]-3,4-dihydro-2H-quinoxalin-1-yl}-butyric acid ethyl ester

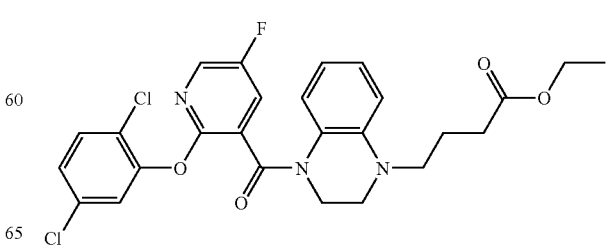

To a solution of [2-(2,5-dichloro-phenoxy)-5-fluoro-pyridin-3-yl]-(3,4-dihydro-2H-quinoxalin-1-yl)-methanone (50.2 mg, 0.12 mmol, 1.0 equiv; Example 147) in anhydrous DMF (1 mL) was added sodium hydride (10.3 mg, 0.24 mmol, 2.0 equiv; 55% free-flowing powder moistened with oil; [CAS RN 7646-69-7]) and the reaction mixture stirred at rt. After 1 h, 4-bromo-butyric acid ethyl ester (545 mg, 400 µL, 2.80 mmol, 23.3 equiv; [CAS RN 2969-81-5]) was added and stirring continued under microwave heating to 120° C. for 30 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 5.5 mg (9%) of the title compound as a light yellow oil. MS (ISP): 532.2 [M+H]$^+$.

Example 159

5-{4-[2-(2,5-Dichloro-phenoxy)-5-fluoro-pyridine-3-carbonyl]-3,4-dihydro-2H-quinoxalin-1-yl}-pentanoic acid ethyl ester

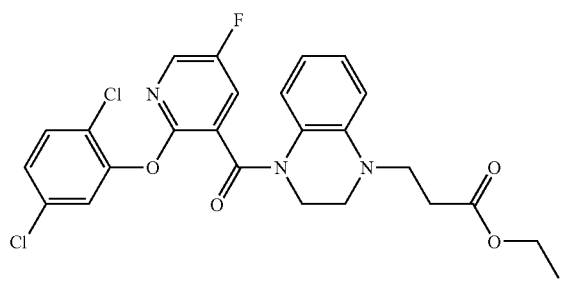

The title compound was prepared in analogy to Example 158 replacing 4-bromo-butyric acid ethyl ester with 5-bromo-pentanoic acid ethyl ester ([CAS RN 14660-52-7]). MS (ISP): 546.3 [M+H]$^+$.

Example 160

6-{4-[2-(2,5-Dichloro-phenoxy)-5-fluoro-pyridine-3-carbonyl]-3,4-dihydro-2H-quinoxalin-1-yl}-hexanoic acid methyl ester

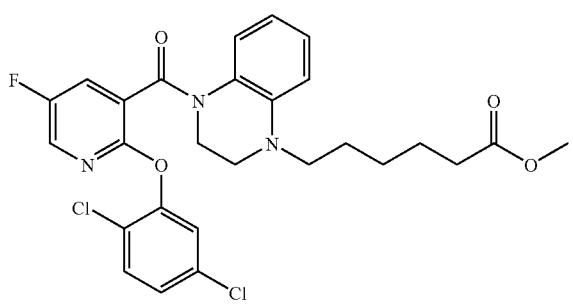

The title compound was prepared in analogy to Example 151 replacing furan-3-carbaldehyde with adipic semialdehyde methyl ester ([CAS RN 6654-36-0]). MS (ISP): 546.3 [M+H]$^+$.

Example 161

6-{4-[2-(2,5-Dichloro-phenoxy)-5-fluoro-pyridine-3-carbonyl]-3,4-dihydro-2H-quinoxalin-1-yl}-hexanoic acid

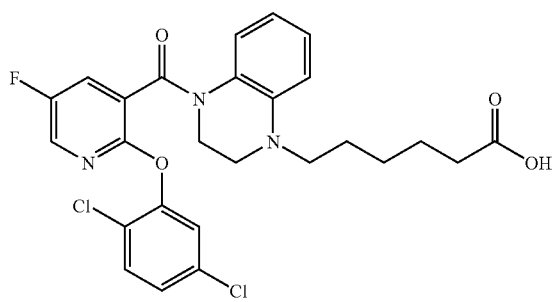

The title compound was prepared in analogy to Example 157 replacing 2-methyl-3-oxo-propionic acid methyl ester with adipic semialdehyde methyl ester ([CAS RN 6654-36-0]). MS (ISP): 532.2 [M+H]$^+$.

Example 162

4-{4-[2-(2,5-Dichloro-phenoxy)-5-fluoro-pyridine-3-carbonyl]-3,4-dihydro-2H-quinoxaline-1-carbonyl}-benzoic acid methyl ester

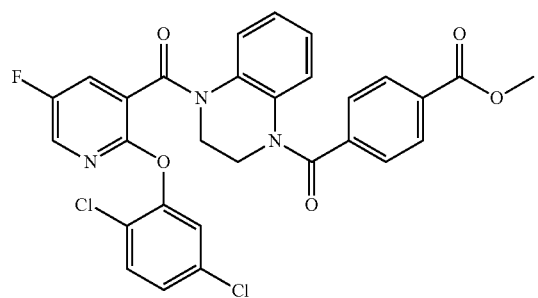

To a solution of [2-(2,5-dichloro-phenoxy)-5-fluoro-pyridin-3-yl]-(3,4-dihydro-2H-quinoxalin-1-yl)-methanone (52.3 mg, 0.125 mmol, 1.0 equiv; Example 147) in anhydrous DMF (1 mL) was added N-ethyldiisopropylamine (65 mg, 85 µL, 0.5 mmol, 4.0 equiv; [CAS RN 7087-68-5]) and 4-chlorocarbonyl-benzoic acid methyl ester (29.8 mg, 0.15 mmol, 1.2 equiv; [CAS RN 7377-26-6]). The reaction mixture was heated by microwave irradiation to 120° C. for 15 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient

Example 163

[2-(4-Bromo-2,5-dichloro-phenoxy)-pyridin-3-yl]-(4-cyclopropyl-3,4-dihydro-2H-quinoxalin-1-yl)-methanone

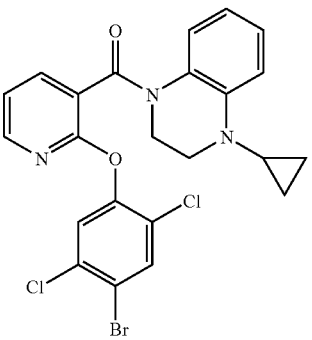

Step 1: 2-(4-Bromo-2,5-dichloro-phenoxy)-nicotinic acid

To a solution of 2-chloro-nicotinic acid (100 mg, 0.64 mmol, 1.0 equiv; [CAS RN 2942-59-8]) and 4-bromo-2,5-dichloro-phenol (184 mg, 0.76 mmol, 1.2 equiv; [CAS RN 1940-42-7]) in toluene (1 mL) was added caesium carbonate (517 mg, 1.59 mmol, 2.5 equiv; [CAS RN 534-17-8]) and tetrakis(acetonitrile)copper(I) hexafluorophosphate (47 mg, 0.13 mmol, 0.2 equiv; [CAS RN 64443-05-6]). The reaction mixture was heated by microwave irradiation to 140° C. for 1 h. The solvent was evaporated under reduced pressure and the crude reaction product taken up in water (100 mL) acidified to pH 1 by addition of a solution of 1 M HCl and extracted with ethyl acetate (3×100 mL). The combined organic phases were dried over MgSO$_4$ and the product purified by silica column chromatography using a MPLC system (CombiFlash Companion, Isco Inc.) eluting with a gradient of dichloromethane/methanol affording 170 mg (73%) of the title compound as an off-white solid. $^1$H NMR (400 MHz, DMSO): δ7.21 (dd, J=-7.6 Hz, J=4.8 Hz, 1H), 7.42 (s, 1H), 7.76 (s, 1H), 8.29 (dd, J=4.8 Hz, J=1.9 Hz, 1H), 8.50 (dd, J=7.7 Hz, J=2.0 Hz, 1H). MS (ISN): 362.0 [M−H]$^−$.

Step 2

To a solution of 2-(4-bromo-2,5-dichloro-phenoxy)-nicotinic acid (50 mg, 0.14 mmol, 1.0 equiv) in anhydrous dichloromethane (1.5 mL) was added N-ethyldiisopropylamine (36 mg, 47 μL, 0.28 mmol, 2.0 equiv; [CAS RN 7087-68-5]) and HATU (68 mg, 0.18 mmol, 1.3 equiv; [CAS RN 148893-10-1]) and the reaction mixture stirred at rt. After 10 min, 1-cyclopropyl-1,2,3,4-tetrahydro-quinoxaline (29 mg, 0.17 mmol, 1.2 equiv; Example 125, Step 5) was added and stirring at rt continued over night. To the reaction was added a sat. solution of NaHCO$_3$ (20 mL) and the solution extracted with dichloromethane (3×20 mL). The combined organic phases were dried over Na$_2$SO$_4$ and the product purified by silica column chromatography using a MPLC system (CombiFlash Companion, Isco Inc.) eluting with a gradient of heptane/ethyl acetate affording 45 mg (63%) of the title compound as an off-white powder. MS (ISP): 520.3 [M+H]$^+$.

Example 164

(4-Cyclopropyl-3,4-dihydro-2H-quinoxalin-1-yl)-{2-[2,5-dichloro-4-(3-hydroxy-prop-1-ynyl)-phenoxy]-pyridin-3-yl}-methanone

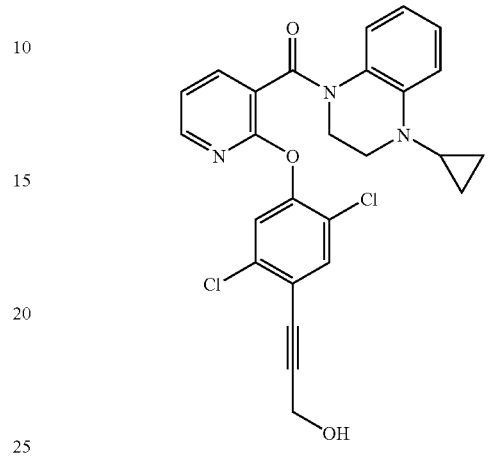

To a degassed suspension of [2-(4-bromo-2,5-dichloro-phenoxy)-pyridin-3-yl]-(4-cyclopropyl-3,4-dihydro-2H-quinoxalin-1-yl)-methanone (100 mg, 0.19 mmol, 1.0 equiv; Example 163) in triethylamine (0.8 mL) under Ar was added 2-propyn-1-ol (216 mg, 220 μL, 3.85 mmol, 20 equiv; [CAS RN 107-19-7]), tetrakis(triphenylphosphine)palladium(0) (22 mg, 0.02 mmol, 0.1 equiv; [CAS RN 14221-01-3]) and copper(I) iodide (3.7 mg, 0.02 mmol, 0.1 equiv; [CAS RN 7681-65-4]). The reaction mixture was heated by microwave irradiation to 100° C. for 1 h. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 49 mg (52%) of the title compound as an off-white powder. MS (ISP): 494.3 [M+H]$^+$.

Example 165

[2-(4-Bromo-2,5-dichloro-phenoxy)-pyridin-3-yl]-(3,4-dihydro-2H-quinolin-1-yl)-methanone

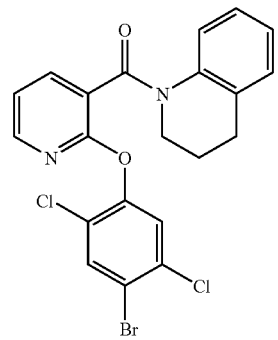

To a solution of 2-(4-bromo-2,5-dichloro-phenoxy)-nicotinic acid (50 mg, 0.14 mmol, 1.0 equiv; Example 163, Step 1)

in anhydrous dichloromethane (1.5 mL) was added N-ethyl-diisopropylamine (152 mg, 200 μL, 1.18 mmol, 8.4 equiv; [CAS RN 7087-68-5]) and 2-chloro-1-methylpyridinium iodide (42 mg, 0.17 mmol, 1.2 equiv; [CAS RN 14338-32-0]) and the reaction mixture stirred at rt. After 1 h, 1,2,3,4-tetrahydro-quinoline (22 mg, 21 μL, 0.17 mmol, 1.2 equiv; [CAS RN 635-46-1]) was added and stirring at rt continued over night. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 41 mg (61%) of the title compound as a white powder. MS (ISP): 476.9 [M+H]+.

Example 166

5-{2,5-Dichloro-4-[3-(3,4-dihydro-2H-quinoline-1-carbonyl)-pyridin-2-yloxy]-phenyl}-pent-4-ynoic acid methyl ester

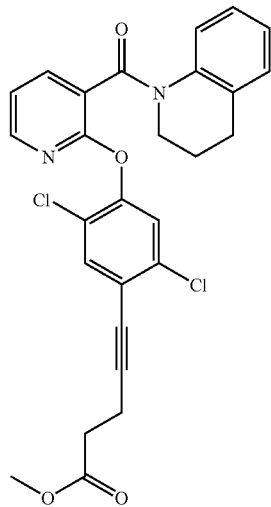

To a degassed suspension of [2-(4-bromo-2,5-dichloro-phenoxy)-pyridin-3-yl]-(3,4-dihydro-2H-quinolin-1-yl)-methanone (50 mg, 0.10 mmol, 1.0 equiv; Example 165) in THF (2 mL) under Ar was added pent-4-ynoic acid methyl ester (34 mg, 0.30 mmol, 3 equiv; [CAS RN 21565-82-2]), tris(dibenzylideneacetone)dipalladium(0) chloroform adduct (1 mg, 0.001 mmol, 0.01 equiv; [CAS RN 52522-40-4]), copper(I) iodide (0.2 mg, 0.001 mmol, 0.01 equiv; [CAS RN 7681-65-4]) and triethylamine (20 mg, 28 μL, 0.20 mmol, 2.0 equiv; [CAS RN 121-44-8]). The reaction mixture was stirred at 60° C. over the weekend. Removal of the solvent mixture under reduced pressure and purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 3 mg (6%) of the title compound as a light brown oil. MS (ISP): 509.1 [M+H]+.

Example 167

2-Chloro-4-{2,5-dichloro-4-[3-(4-cyclopropyl-3,4-dihydro-2H-quinoxaline-1-carbonyl)-pyridin-2-yloxy]-phenylethynyl}-benzoic acid methyl ester

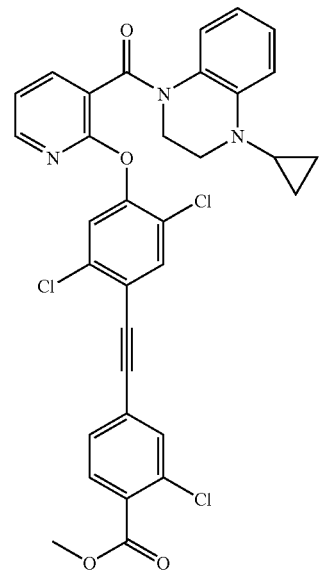

Step 1: 2-Chloro-4-trimethylsilanylethynyl-benzoic acid methyl ester

To a degassed solution of 4-bromo-2-chloro-benzoic acid methyl ester (3.0 g, 12.0 mmol, 1.0 equiv; [CAS RN 185312-82-7]) in triethylamine (24.3 g, 33.5 mL, 240.5 mmol, 20.0 equiv; [CAS RN 121-44-8]) under Ar was added ethynyl-trimethyl-silane (1.24 g, 1.78 mL, 12.63 mmol, 1.05 equiv; [CAS RN 1066-54-2]), tetrakis(triphenylphosphine)palladium(0) (0.70 g, 0.60 mmol, 0.05 equiv; [CAS RN 14221-01-3]) and copper(I) iodide (0.23 g, 1.20 mmol, 0.1 equiv; [CAS RN 7681-65-4]) and the reaction mixture heated to 70° C. for 18 h. The crude reaction was filtered over Celite®, a sat. solution of NaCl (50 mL) added and extracted with ethyl acetate (3×50 mL). The combined organic phases were dried over Na2SO4 and the product used in the consecutive step without any further purification. Yield: 4.52 g (99%) of the title compound in ca. 70% purity as a slightly brown oil. MS (ISN): 267.0 [M+H]+.

Step 2: 2-Chloro-4-ethynyl-benzoic acid methyl ester

To a solution of 2-chloro-4-trimethylsilanylethynyl-benzoic acid methyl ester (4.52 g, 12.0 mmol, 1.0 equiv; 70% purity) in THF (50 mL) was as added a 1 M solution of tetrabutylammonium fluoride in THF (14.4 mL, 14.40 mmol, 1.20 equiv; [CAS RN 429-41-4]) and the reaction mixture stirred at rt over night. The crude reaction was extracted from a sat. solution of NH4Cl (50 mL) with ethyl acetate (3×50 mL) and the combined organic phases dried over Na2SO4. Purification of the crude reaction product by silica column chromatography using a MPLC system (CombiFlash Companion, Isco Inc.) eluting with a mixture of dichloromethane/methanol (4:1) provided 1.12 g (48%) of the title compound as a slightly orange solid. MS (ISN): 195.1 [M+H]+.

Step 3

To a degassed suspension of [2-(4-bromo-2,5-dichlorophenoxy)-pyridin-3-yl]-(4-cyclopropyl-3,4-dihydro-2H-quinoxalin-1-yl)-methanone (100 mg, 0.19 mmol, 1.0 equiv; Example 163) in triethylamine (0.73 g, 1.0 mL, 7.21 mmol, 38.0 equiv; [CAS RN 121-44-8]) under Ar was added 2-chloro-4-ethynyl-benzoic acid methyl ester (120 mg, 0.62 mmol, 3.2 equiv), tetrakis(triphenylphosphine)palladium(0) (22 mg, 0.02 mmol, 0.1 equiv; [CAS RN 14221-01-3]) and copper(I) iodide (3.7 mg, 0.02 mmol, 0.1 equiv; [CAS RN 7681-65-4]). The reaction mixture was heated by microwave irradiation to 100° C. for 40 min. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) and eluting with a gradient of acetonitrile/water provided 40 mg (33%) of the title compound as a light brown powder. MS (ISP): 634.2 [M+H]+.

Example 168
2-Chloro-4-{2,5-dichloro-4-[3-(4-cyclopropyl-3,4-dihydro-2H-quinoxaline-1-carbonyl)-pyridin-2-yloxy]-phenylethynyl}-benzoic acid

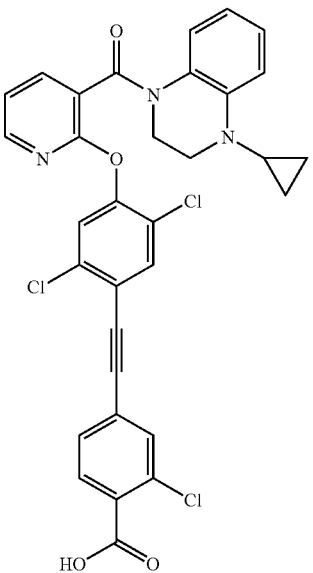

To a solution of 2-chloro-4-{2,5-dichloro-4-[3-(4-cyclopropyl-3,4-dihydro-2H-quinoxaline-1-carbonyl)-pyridin-2-yloxy]-phenylethynyl}-benzoic acid methyl ester (150 mg, 0.24 mmol, 1.0 equiv; Example 167) in a 2:2:1 mixture of THF, methanol and water (2 mL) was added lithium hydroxide (11.4 mg, 0.47 mmol, 2.0 equiv; [CAS RN 1310-65-2]) and the reaction mixture stirred at rt over night. The crude reaction product was taken up in water (50 mL), acidified to pH 1 by addition of a solution of 1 M HCl and extracted with ethyl acetate (3×40 mL). The combined organic phases were dried over MgSO4 and the product purified by silica column chromatography using a MPLC system (CombiFlash Companion, Isco Inc.) eluting with a gradient of dichloromethane/methanol to give 110 mg (75%) of the title compound as a light brown solid. MS (ISN): 616.1 [M−H]−.

Example 169
2-Chloro-4-(2-{2,5-dichloro-4-[3-(4-cyclopropyl-3,4-dihydro-2H-quinoxaline-1-carbonyl)-pyridin-2-yloxy]-phenyl}-ethyl)-benzoic acid

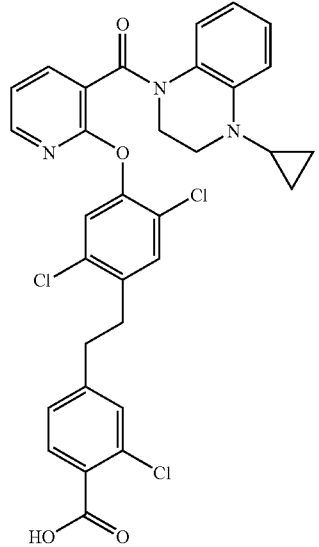

To a suspension of 2-chloro-4-{2,5-dichloro-4-[3-(4-cyclopropyl-3,4-dihydro-2H-quinoxaline-1-carbonyl)-pyridin-2-yloxy]-phenylethynyl}-benzoic acid (100 mg, 0.16 mmol, 1.0 equiv; Example 168) in ethanol (1.5 mL) was added palladium on carbon (3.2 mg, 0.003 mmol, 0.02 equiv; 10% Pd/C; [CAS RN 7440-05-3]) and the reaction mixture stirred under an atmosphere of hydrogen (3 bar) at rt over night. Removal of the solvent mixture under reduced pressure, filtration over Celite® and lyophilization from dioxane provided 100 mg (96%) of the title compound as an off-white solid. MS (ISP): 620.3 [M−H]−.

Example 170
4-(2-{2,5-Dichloro-4-[3-(4-cyclopropyl-3,4-dihydro-2H-quinoxaline-1-carbonyl)-pyridin-2-yloxy]-phenyl}-ethyl)-benzoic acid

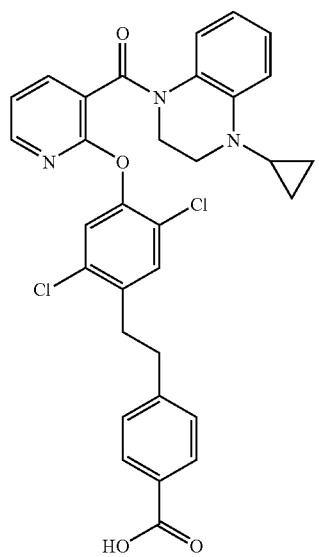

Step 1: 4-{2,5-Dichloro-4-[3-(4-cyclopropyl-3,4-dihydro-2H-quinoxaline-1-carbonyl)-pyridin-2-yloxy]-phenylethynyl}-benzoic acid methyl ester The title compound was prepared in analogy to Example 167, Step 3, replacing 2-chloro-4-ethynyl-benzoic acid methyl ester with 4-ethynyl-benzoic acid methyl ester ([CAS RN 3034-86-4]). MS (ISP): 598.2 [M+H]⁺.

Step 2: 4-{2,5-Dichloro-4-[3-(4-cyclopropyl-3,4-dihydro-2H-quinoxaline-1-carbonyl)-pyridin-2-yloxy]-phenylethynyl}-benzoic acid methyl ester The title compound was prepared in analogy to Example 169 replacing 2-chloro-4-{2,5-dichloro-4-[3-(4-cyclopropyl-3,4-dihydro-2H-quinoxaline-1-carbonyl)-pyridin-2-yloxy]-phenylethynyl}-benzoic acid with 4-{2,5-dichloro-4-[3-(4-cyclopropyl-3,4-dihydro-2H-quinoxaline-1-carbonyl)-pyridin-2-yloxy]-phenylethynyl}-benzoic acid methyl ester. MS (ISP): 602.2 [M+H]⁺.

Step 3

The title compound was prepared in analogy to Example 168 replacing 2-chloro-4-{2,5-dichloro-4-[3-(4-cyclopropyl-3,4-dihydro-2H-quinoxaline-1-carbonyl)-pyridin-2-yloxy]-phenylethynyl}-benzoic acid methyl ester with 4-{2,5-dichloro-4-[3-(4-cyclopropyl-3,4-dihydro-2H-quinoxaline-1-carbonyl)-pyridin-2-yloxy]-phenylethynyl}-benzoic acid methyl ester. MS (ISP): 588.2 [M+H]⁺.

Example 171

4-(2-{2,5-Dichloro-4-[3-(4-cyclopropyl-3,4-dihydro-2H-quinoxaline-1-carbonyl)-pyridin-2-yloxy]-phenyl}-ethyl)-3-methoxy-benzoic acid

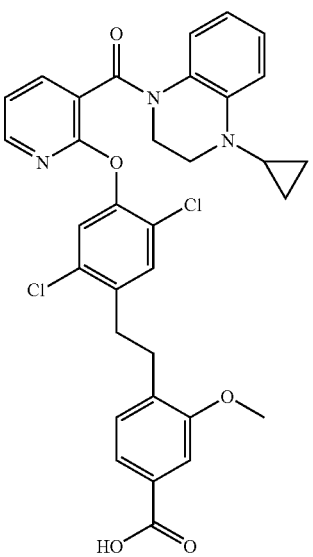

The title compound was prepared in analogy to Example 170, Steps 1-3, replacing 4-ethynyl-benzoic acid methyl ester with 4-ethynyl-3-methoxy-benzoic acid methyl ester (prepared in analogy to Example 167, Steps 1-2, replacing 4-bromo-2-chloro-benzoic acid methyl ester with 4-bromo-3-methoxy-benzoic acid methyl ester ([CAS RN 17100-63-9])). MS (ISP): 616.3 [M–H]⁻.

Example 172

3-{2,5-Dichloro-4-[3-(4-cyclopropyl-3,4-dihydro-2H-quinoxaline-1-carbonyl)-pyridin-2-yloxy]-phenyl}-acrylic acid

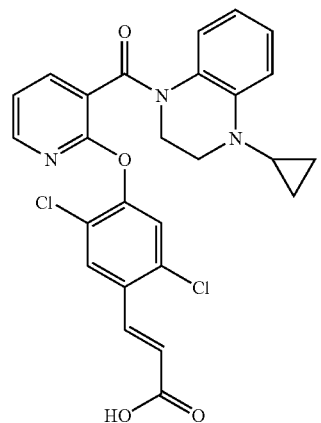

Step 1: 3-{2,5-Dichloro-4-[3-(4-cyclopropyl-3,4-dihydro-2H-quinoxaline-1-carbonyl)-pyridin-2-yloxy]-phenyl}-acrylic acid ethyl ester To a degassed solution of [2-(4-bromo-2,5-dichloro-phenoxy)-pyridin-3-yl]-(4-cyclopropyl-3,4-dihydro-2H-quinoxalin-1-yl)-methanone (500 mg, 0.96 mmol, 1.0 equiv; Example 163) in propionitrile (10 mL) under Ar was added N-ethyldiisopropylamine (373 mg, 491 µL, 2.89 mmol, 3.0 equiv; [CAS RN 7087-68-5]), ethyl acrylate (0.58 g, 0.63 mL, 5.78 mmol, 6.0 equiv; [CAS RN 140-88-5]), palladium(II) acetate (22 mg, 0.10 mmol, 0.1 equiv; [CAS RN 3375-31-3]) and tri-o-tolyl-phosphane (59 mg, 0.19 mmol, 0.2 equiv; [CAS RN 6163-58-2]). The reaction mixture was heated to 95° C. over night. The crude reaction was filtered over Celite®, a sat. solution of NaCl (50 mL) added and extracted with ethyl acetate (3×50 mL). The combined organic phases were dried over Na₂SO₄ and the product purified by silica column chromatography using a MPLC system (CombiFlash Companion, Isco Inc.) eluting with a gradient of heptane/ethyl acetate affording 320 mg (62%) of the title compound as a yellow foam. MS (ISN): 538.3 [M+H]⁺.

Step 2

To a solution of 3-{2,5-dichloro-4-[3-(4-cyclopropyl-3,4-dihydro-2H-quinoxaline-1-carbonyl)-pyridin-2-yloxy]-phenyl}-acrylic acid ethyl ester (74 mg, 0.14 mmol, 1.0 equiv) in a 1:1 mixture of THF and water (2 mL) was added sodium hydroxide (11 mg, 0.28 mmol, 2.0 equiv; [CAS RN 1310-73-2]) and the reaction mixture heated by microwave irradiation to 100° C. for 10 min. The crude reaction product was taken up in water (50 mL), acidified to pH 1 by addition of a solution of 1 M HCl and extracted with ethyl acetate (3×40 mL). The combined organic phases were dried over MgSO₄ and the product purified by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water yielding 21 mg (30%) of the title compound as a yellow viscous oil. MS (ISP): 509.9 [M+H]⁺.

Example 173

3-{2,5-Dichloro-4-[3-(4-cyclopropyl-3,4-dihydro-2H-quinoxaline-1-carbonyl)-pyridin-2-yloxy]-phenyl}-propionic acid

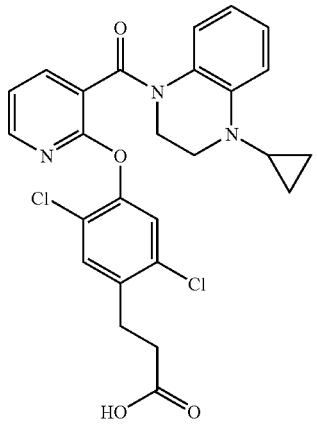

To a suspension of 3-{2,5-dichloro-4-[3-(4-cyclopropyl-3,4-dihydro-2H-quinoxaline-1-carbonyl)-pyridin-2-yloxy]-phenyl}-acrylic acid (36 mg, 0.07 mmol, 1.0 equiv; Example 172) in ethanol (1.5 mL) was added palladium on carbon (1.5 mg, 0.001 mmol, 0.02 equiv; 10% Pd/C; [CAS RN 7440-05-3]) and the reaction mixture stirred under an atmosphere of hydrogen (3 bar) at rt over night. Removal of the solvent mixture under reduced pressure, filtration over Celite® and purification by preparative HPLC on reversed phase (Xterra® PrepMSC 18, 5 μm, 19×50 mm column equipped with a Gilson Liquid Handler 215 auto sampler, two Rainin Dynamax® SD-300 pumps, a Sedex ELSD 75 lightscatter and a Dionex UVD 340S UV detector) eluting with a gradient of acetonitrile/water provided 12 mg (33%) of the title compound as a slightly yellow viscous oil. MS (ISP): 513.8 [M+H]⁺.

Example 174

4-{2,5-Dichloro-4-[3-(4-cyclopropyl-3,4-dihydro-2H-quinoxaline-1-carbonyl)-pyridin-2-yloxy]-phenyl}-but-3-enoic acid methyl ester

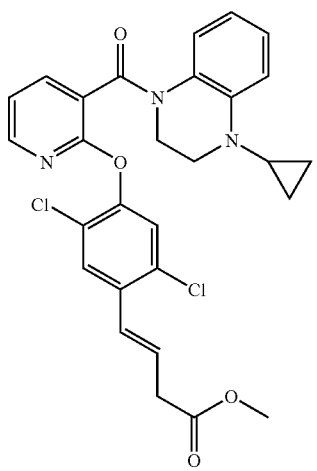

The title compound was prepared in analogy to Example 172, Step 1, replacing ethyl acrylate with but-3-enoic acid methyl ester ([CAS RN 3724-55-8]). MS (ISP): 538.3 [M+H]⁺.

Example 175

4-{2,5-Dichloro-4-[3-(4-cyclopropyl-3,4-dihydro-2H-quinoxaline-1-carbonyl)-pyridin-2-yloxy]-phenyl}-but-3-enoic acid

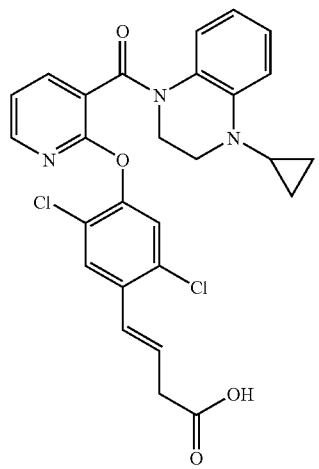

The title compound was prepared in analogy to Example 172, Step 2, replacing 3-{2,5-dichloro-4-[3-(4-cyclopropyl-3,4-dihydro-2H-quinoxaline-1-carbonyl)-pyridin-2-yloxy]-phenyl}-acrylic acid ethyl ester with 4-{2,5-dichloro-4-[3-(4-cyclopropyl-3,4-dihydro-2H-quinoxaline-1-carbonyl)-pyridin-2-yloxy]-phenyl}-but-3-enoic acid methyl ester (Example 174). MS (ISP): 524.5 [M+H]⁺.

Example 176

4-{2,5-Dichloro-4-[3-(4-cyclopropyl-3,4-dihydro-2H-quinoxaline-1-carbonyl)-pyridin-2-yloxy]-phenyl}-butyric acid

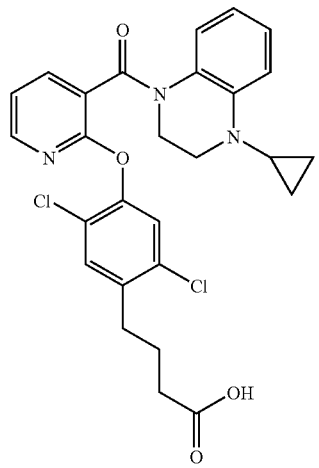

The title compound was prepared in analogy to Example 173 replacing 3-{2,5-dichloro-4-[3-(4-cyclopropyl-3,4-dihydro-2H-quinoxaline-1-carbonyl)-pyridin-2-yloxy]-phenyl}-acrylic acid with 4-{2,5-dichloro-4-[3-(4-cyclopropyl-3,4-dihydro-2H-quinoxaline-1-carbonyl)-pyridin-2-yloxy]-phenyl}-but-3-enoic acid (Example 175). MS (ISP): 526.3 [M+H]⁺.

Example 177

(3-{2,5-Dichloro-4-[3-(4-cyclopropyl-3,4-dihydro-2H-quinoxaline-1-carbonyl)-pyridin-2-yloxy]-phenyl}-propionylamino)-acetic acid

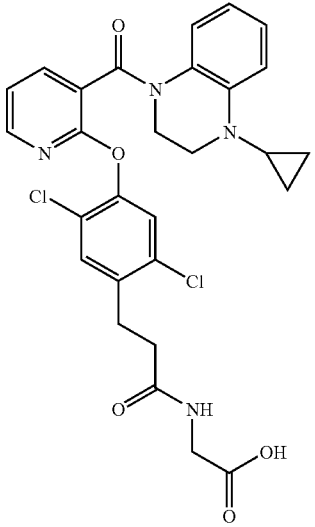

To a solution of 3-{2,5-dichloro-4-[3-(4-cyclopropyl-3,4-dihydro-2H-quinoxaline-1-carbonyl)-pyridin-2-yloxy]-phenyl}-propionic acid (50 mg, 0.098 mmol, 1.0 equiv; Example 173) in anhydrous DMF (1 mL) was added HATU (44.5 mg, 0.12 mmol, 1.2 equiv; [CAS RN 148893-10-1]) and N-ethyldiisopropylamine (25 mg, 33 µL, 0.20 mmol, 2.0 equiv; [CAS RN 7087-68-5]). After stirring the reaction mixture for 10 min, glycine (8.1 mg, 0.11 mmol, 1.1 equiv; [CAS RN 56-40-6]) was added and stirring continued at rt over night. Removal of the solvent mixture under reduced pressure and purification by preparative HPLC on reversed phase (Xterra® PrepMSC 18, 5 µm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 9 mg (16%) of the title compound as a light yellow oil. MS (ISP): 569.2 [M+H]$^+$.

Example 178

[(b 3-{2,5-Dichloro-4-[3-(4-cyclopropyl-3,4-dihydro-2H-quinoxaline-1-carbonyl)-pyridin-2-yloxy]-phenyl}-propionyl)-methyl-amino]-acetic acid

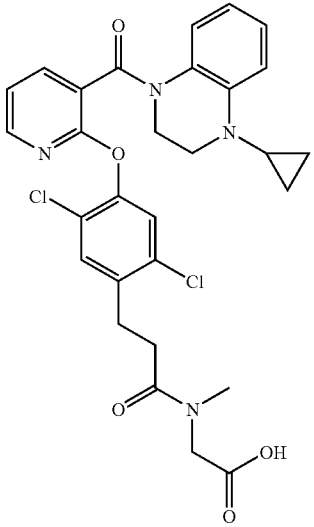

The title compound was prepared in analogy to Example 177 replacing glycine with sarcosine ([CAS RN 107-97-1]). MS (ISP): 583.0 [M+H]$^+$.

Example 179

3-(3-{2,5-Dichloro-4-[3-(4-cyclopropyl-3,4-dihydro-2H-quinoxaline-1-carbonyl)-pyridin-2-yloxy]-phenyl}-propionylamino)-propionic acid

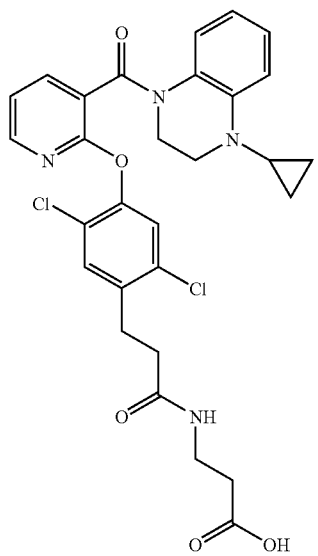

The title compound was prepared in analogy to Example 177 replacing glycine with β-alanine ([CAS RN 107-95-9]). MS (ISP): 583.2 [M+H]$^+$.

Example 180

1-(3-{2,5-Dichloro-4-[3-(4-cyclopropyl-3,4-dihydro-2H-quinoxaline-1-carbonyl)-pyridin-2-yloxy]-phenyl}-propionyl)-pyrrolidine-2-carboxylic acid

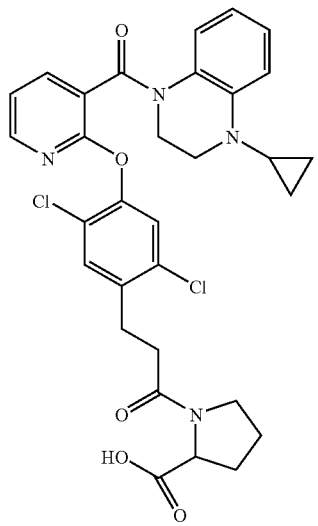

The title compound was prepared in analogy to Example 177 replacing glycine with DL-proline ([CAS RN 609-36-9]). MS (ISP): 607.3 [M+H]$^+$.

Example 181

3-(4-{2,5-Dichloro-4-[3-(4-cyclopropyl-3,4-dihydro-2H-quinoxaline-1-carbonyl)-pyridin-2-yloxy]-phenyl}-butyrylamino)-propionic acid

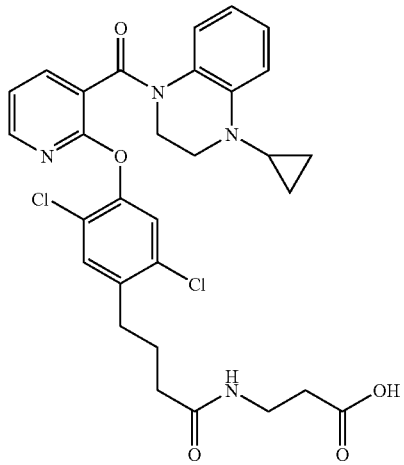

The title compound was prepared in analogy to Example 179 replacing 3-{2,5-dichloro-4-[3-(4-cyclopropyl-3,4-dihydro-2H-quinoxaline-1-carbonyl)-pyridin-2-yloxy]-phenyl}-propionic acid with 4-{2,5-dichloro-4-[3-(4-cyclopropyl-3,4-dihydro-2H-quinoxaline-1-carbonyl)-pyridin-2-yloxy]-phenyl}-butyric acid (Example 176). MS (ISP): 597.3 [M+H]+.

Example 182

2,5-Dichloro-4-[3-(4-cyclopropyl-3,4-dihydro-2H-quinoxaline-1-carbonyl)-pyridin-2-yloxy]-benzoic acid methyl ester

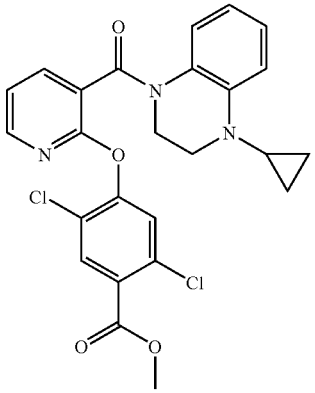

To a solution of [2-(4-bromo-2,5-dichloro-phenoxy)-pyridin-3-yl]-(4-cyclopropyl-3,4-dihydro-2H-quinoxalin-1-yl)-methanone (100 mg, 0.19 mmol, 1.0 equiv; Example 163) in a 1:1 mixture of methanol and ethyl acetate (4 mL) was added 1,1'-bis(diphenylphosphino)ferrocene palladium (II) chloride (10.1 mg, 0.012 mmol, 0.064 equiv; [CAS RN 95464-05-4]) and the reaction mixture stirred under an atmosphere of carbon monoxide (70 bar) at 100° C. for 20 h. The crude reaction mixture was filtered over Celite® and purified by silica column chromatography using a MPLC system (CombiFlash Companion, Isco Inc.) eluting with a gradient of heptane/ethyl acetate to afford 50 mg (52%) of the title compound as a off-white solid. MS (ISN): 498.3 [M+H]+.

Example 183

{2,5-Dichloro-4-[3-(4-cyclopropyl-3,4-dihydro-2H-quinoxaline-1-carbonyl)-pyridin-2-yloxy]-benzoylamino}-acetic acid methyl ester

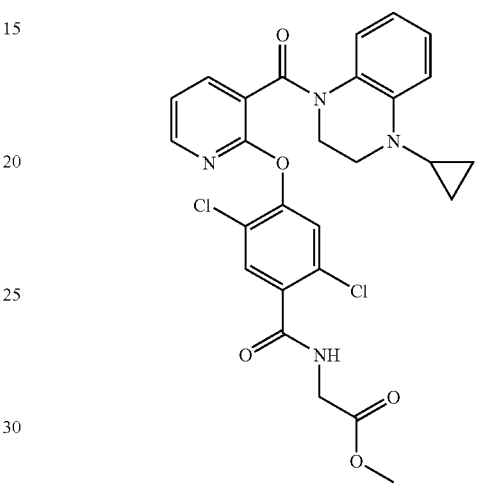

Step 1: 2,5-Dichloro-4-[3-(4-cyclopropyl-3,4-dihydro-2H-quinoxaline-1-carbonyl)-pyridin-2-yloxy]-benzoic acid To a solution of 2,5-dichloro-4-[3-(4-cyclopropyl-3,4-dihydro-2H-quinoxaline-1-carbonyl)-pyridin-2-yloxy]-benzoic acid methyl ester (50 mg, 0.10 mmol, 1.0 equiv; Example 182) in a 2:2:1 mixture of THF, methanol and water (2 mL) was added lithium hydroxide (4.8 mg, 0.20 mmol, 2.0 equiv; [CAS RN 1310-65-2]) and the reaction mixture stirred at rt over night. The crude reaction product was taken up in water (50 mL), acidified to pH 1 by addition of a solution of 1 M HCl and extracted with ethyl acetate (3×40 mL). The combined organic phases were dried over MgSO4 and the product purified by silica column chromatography using a MPLC system (CombiFlash Companion, Isco Inc.) eluting with a gradient of heptane/ethyl acetate to give 40 mg (82%) of the title compound as a light yellow solid. MS (ISN): 482.0 [M−H]−.

Step 2

To a solution of 2,5-dichloro-4-[3-(4-cyclopropyl-3,4-dihydro-2H-quinoxaline-1-carbonyl)-pyridin-2-yloxy]-benzoic acid (38 mg, 0.079 mmol, 1.0 equiv) in dichloromethane (1.5 mL) was added HATU (38.8 mg, 0.10 mmol, 1.3 equiv; [CAS RN 148893-10-1]) and triethylamine (16 mg, 22 μL, 0.16 mmol, 2.0 equiv; [CAS RN 121-44-8]). After stirring the reaction mixture for 15 min, glycine methyl ester hydrochloride (12.8 mg, 0.10 mmol, 1.3 equiv; [CAS RN 5680-79-5]) was added and stirring continued at rt for 4 h. The crude reaction product was taken up in a sat. solution of NaHCO3 (50 mL) and extracted with dichloromethane (3×40 mL). The combined organic phases were dried over MgSO₄ and the product purified by silica column chromatography using a MPLC system (CombiFlash Companion, Isco Inc.) eluting with a gradient of heptane/ethyl acetate to give 43 mg (99%) of the title compound as a light yellow viscous oil. MS (ISN): 555.3 [M+H]⁺.

Example 184

(4-Cyclopropyl-3,4-dihydro-2H-quinoxalin-1-yl)-[2-(2,5-dichloro-phenoxy)-phenyl]-methanone

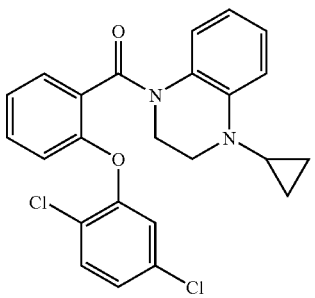

The title compound was prepared in analogy to Example 110, Step 2, replacing 1,2,3,4-tetrahydro-quinoline with 1-cyclopropyl-1,2,3,4-tetrahydro-quinoxaline (Example 125, Steps 1-5). MS (ISP): 439.1 [M+H]⁺.

Example 185

[3-(2,5-Dichloro-phenoxy)-pyridin-4-yl]-(2,3-dihydro-benzo[1,4]oxazin-4-yl)-methanone

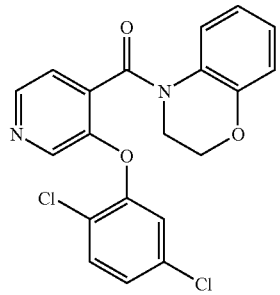

Step 1: (3-Bromo-pyridin-4-yl)-(2,3-dihydro-benzo[1,4]oxazin-4-yl)-methanone

The title compound was prepared in analogy to Example 6, Step 1, replacing 2-chloro-nicotinic acid with 3-bromo-isonicotinic acid [CAS RN 13959-02-9]) and 1,2,3,4-tetrahydro-quinoline with 3,4-dihydro-2H-benzo[1,4]oxazine ([CAS RN 5735-53-5]). MS (ISP): 319.0 [M+H]⁺.

Step 2

To a solution of (3-bromo-pyridin-4-yl)-(2,3-dihydro-benzo[1,4]oxazin-4-yl)-methanone (80 mg, 0.25 mmol, 1.0 equiv) and 2,5-dichloro-phenol (49 mg, 0.30 mmol, 1.2 equiv; [CAS RN 583-78-8]) in anhydrous toluene (1.5 mL) was added caesium carbonate (204 mg, 0.63 mmol, 2.5 equiv; [CAS RN 534-17-8]) and tetrakis(acetonitrile)copper(I) hexafluorophosphate (18.7 mg, 0.050 mmol, 0.2 equiv; [CAS RN 64443-05-6]). The reaction mixture was heated by microwave irradiation to 160° C. for 2 h. Purification by preparative HPLC on reversed phase (Xterra® PrepMSC 18, 5 μm, 19×50 mm column equipped with a Gilson Liquid Handler 215 autosampler, two Rainin Dynamax® SD-300 pumps, a Sedex ELSD 75 lightscatter and a Dionex UVD 340S UV detector) eluting with a gradient of acetonitrile/water provided 17 mg (17%) of the title compound as a light brown solid. MS (ISP): 400.9 [M+H]⁺.

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula I | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula I | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidone in water. The granulate is mixed with magnesiumstearate and the flavouring additives and filled into sachets.

It is to be understood that the invention is not limited to the particular embodiments of the invention described above, as variations of the particular embodiments may be made and still fall within the scope of the appended claims.

What is claimed is:

1. A compound, selected from the group consisting of:
(3,4-dihydro-2H-quinolin-1-yl)-[2-(3-trifluoromethyl-phenoxy)-pyridin-3-yl]-methanone,
[2-(2-chloro-phenoxy)-pyridin-3-yl]-(3,4-dihydro-2H-quinolin-1-yl)-methanone,
[2-(3-chloro-phenoxy)-pyridin-3-yl]-(3,4-dihydro-2H-quinolin-1-yl)-methanone,
(6-methyl-3,4-dihydro-2H-quinolin-1-yl)-[2-(3-trifluoromethyl-phenoxy)-pyridin-3-yl]-methanone,
[2-(3-chloro-phenoxy)-pyridin-3-yl]-(6-methyl-3,4-dihydro-2H-quinolin-1-yl)-methanone,
[2-(3,4-dichloro-phenoxy)-pyridin-3-yl]-(3,4-dihydro-2H-quinolin-1-yl)-methanone,
3-[3-(3,4-dihydro-2H-quinoline-1-carbonyl)-pyridin-2-yloxy]-benzonitrile,
(3,4-dihydro-2H-quinolin-1-yl)-(2-m-tolyloxy-pyridin-3-yl)-methanone,
[2-(3-chloro-4-methyl-phenoxy)-pyridin-3-yl]-(3,4-dihydro-2H-quinolin-1-yl)-methanone,
[2-(3-chloro-4-fluoro-phenoxy)-pyridin-3-yl]-(3,4-dihydro-2H-quinolin-1-yl)-methanone,
[2-(5-chloro-2-methyl-phenoxy)-pyridin-3-yl]-(3,4-dihydro-2H-quinolin-1-yl)-methanone,
[2-(2,3-dichloro-phenoxy)-pyridin-3-yl]-(3,4-dihydro-2H-quinolin-1-yl)-methanone,
[2-(3-chloro-5-fluoro-phenoxy)-pyridin-3-yl]-(3,4-dihydro-2H-quinolin-1-yl)-methanone,
(3,4-dihydro-2H-quinolin-1-yl)-[2-(2,4,5-trichloro-phenoxy)-pyridin-3-yl]-methanone,
[2-(3-benzoyl-phenoxy)-pyridin-3-yl]-(3,4-dihydro-2H-quinolin-1-yl)-methanone,
(3,4-dihydro-2H-quinolin-1-yl)-[2-(3-trifluoromethoxy-phenoxy)-pyridin-3-yl]-methanone,
[2-(3,5-dichloro-phenoxy)-pyridin-3-yl]-(3,4-dihydro-2H-quinolin-1-yl)-methanone,
(3,4-dihydro-2H-quinolin-1-yl)-[2-(3-fluoro-phenoxy)-pyridin-3-yl]-methanone,
(3,4-dihydro-2H-quinolin-1-yl)-[2-(3-isopropyl-phenoxy)-pyridin-3-yl]-methanone,
(3,4-dihydro-2H-quinolin-1-yl)-[2-(3-ethyl-phenoxy)-pyridin-3-yl]-methanone,
(3,4-dihydro-2H-quinolin-1-yl)-[2-(3-iodo-phenoxy)-pyridin-3-yl]-methanone,
[2-(3-chloro-2-fluoro-5-trifluoromethyl-phenoxy)-pyridin-3-yl]-(3,4-dihydro-2H-quinolin-1-yl)-methanone,
[2-(3-bromo-phenoxy)-pyridin-3-yl]-(3,4-dihydro-2H-quinolin-1-yl)-methanone,
[2-(2,5-dichloro-phenoxy)-pyridin-3-yl]-(3,4-dihydro-2H-quinolin-1-yl)-methanone,
[2-(3-chloro-phenoxy)-5-fluoro-pyridin-3-yl]-(3,4-dihydro-2H-quinolin-1-yl)-methanone,
[2-(2,5-difluoro-phenoxy)-5-fluoro-pyridin-3-yl]-(3,4-dihydro-2H-quinolin-1-yl)-methanone,
[5-chloro-2-(2,5-dichloro-phenoxy)-pyridin-3-yl]-(3,4-dihydro-2H-quinolin-1-yl)-methanone,
[5-chloro-2-(2,5-difluoro-phenoxy)-pyridin-3-yl]-(3,4-dihydro-2H-quinolin-1-yl)-methanone,
[2-(2,5-dichloro-phenoxy)-6-trifluoromethyl-pyridin-3-yl]-(3,4-dihydro-2H-quinolin-1-yl)-methanone,
[2-(3-chloro-phenoxy)-pyridin-3-yl]-(2,3-dihydro-benzo[1,4]oxazin-4-yl)-methanone,
[2-(2,5-dichloro-phenoxy)-pyridin-3-yl]-(6-methyl-3,4-dihydro-2H-quinolin-1-yl)-methanone, 2-(2,5-dichloro-phenoxy)-N-ethyl-N-phenyl-nicotinamide,
(7-chloro-3,4-dihydro-2H-quinolin-1-yl)-[2-(2,5-dichloro-phenoxy)-pyridin-3-yl]-methanone,
[2-(2,5-dichloro-phenoxy)-pyridin-3-yl]-(7-fluoro-3,4-dihydro-2H-quinolin-1-yl)-methanone,
2-(2,5-dichloro-phenoxy)-N-methyl-N-phenyl-nicotinamide,
[2-(2,5-dichloro-phenoxy)-pyridin-3-yl]-(2,3-dihydro-benzo[1,4]oxazin-4-yl)-methanone,
[2-(2,5-dichloro-phenoxy)-pyridin-3-yl]-(6-fluoro-3,4-dihydro-2H-quinolin-1-yl)-methanone,
[2-(2,5-dichloro-phenoxy)-pyridin-3-yl]-(6,7-difluoro-3,4-dihydro-2H-quinolin-1-yl)-methanone,
[2-(2,5-dichloro-phenoxy)-pyridin-3-yl]-(2,3-dihydro-benzo[1,4]thiazin-4-yl)-methanone,
N-(2-chloro-phenyl)-2-(2,5-dichloro-phenoxy)-N-methyl-nicotinamide,
2-(2,5-dichloro-phenoxy)-N-methyl-N-o-tolyl-nicotinamide,
2-(2,5-dichloro-phenoxy)-N-(2-methoxy-phenyl)-N-methyl-nicotinamide,
N-biphenyl-2-yl-2-(2,5-dichloro-phenoxy)-N-methyl-nicotinamide,
[2-(2,5-dichloro-phenoxy)-pyridin-3-yl]-(6,8-difluoro-3,4-dihydro-2H-quinolin-1-yl)-methanone,
2-(2,5-dichloro-phenoxy)-N-(2-ethyl-phenyl)-N-methyl-nicotinamide,
N-(3-chloro-pyridin-2-yl)-2-(2,5-dichloro-phenoxy)-N-methyl-nicotinamide,
N-(4-chloro-pyridin-3-yl)-2-(2,5-dichloro-phenoxy)-N-methyl-nicotinamide,
2-(2,5-dichloro-phenoxy)-N-(2-methoxy-pyridin-3-yl)-N-methyl-nicotinamide,
N-(3-chloro-2-methyl-phenyl)-2-(2,5-dichloro-phenoxy)-N-methyl-nicotinamide,
N-(5-chloro-2-methyl-phenyl)-2-(2,5-dichloro-phenoxy)-N-methyl-nicotinamide,
N-(2-chloro-6-methyl-phenyl)-2-(2,5-dichloro-phenoxy)-N-methyl-nicotinamide,
2-(2,5-dichloro-phenoxy)-N-(2,6-dimethyl-phenyl)-N-methyl-nicotinamide,
2-(2,5-dichloro-phenoxy)-N-(2-methoxy-6-methyl-phenyl)-N-methyl-nicotinamide,
2-(2,5-dichloro-phenoxy)-N-(5-fluoro-2-methoxy-phenyl)-N-methyl-nicotinamide,
N-(5-chloro-2-methoxy-phenyl)-2-(2,5-dichloro-phenoxy)-N-methyl-nicotinamide,
N-(4-chloro-2-methyl-phenyl)-2-(2,5-dichloro-phenoxy)-N-methyl-nicotinamide,
2-(2,5-dichloro-phenoxy)-N-(2,3-dimethyl-phenyl)-N-methyl-nicotinamide,
2-(2,5-dichloro-phenoxy)-N-(2,4-dimethyl-phenyl)-N-methyl-nicotinamide,
2-(2,5-dichloro-phenoxy)-N-(2-methoxy-5-methyl-phenyl)-N-methyl-nicotinamide,
2-(2,5-dichloro-phenoxy)-N-(2,6-dimethoxy-phenyl)-N-methyl-nicotinamide,
N-(6-chloro-4-methyl-pyridin-3-yl)-2-(2,5-dichloro-phenoxy)-N-methyl-nicotinamide,
N-(2-cyano-phenyl)-2-(2,5-dichloro-phenoxy)-N-methyl-nicotinamide,
2-(2,5-dichloro-phenoxy)-N-(2-fluoro-phenyl)-N-methyl-nicotinamide,
2-(2,5-dichloro-phenoxy)-N-(2,6-difluoro-phenyl)-N-methyl-nicotinamide,
2-(2,5-dichloro-phenoxy)-N-methyl-N-(2-pyrrol-1-yl-phenyl)-nicotinamide,
2-(2,5-dichloro-phenoxy)-N-(2,4-difluoro-phenyl)-N-methyl-nicotinamide,
[2-(2,5-dichloro-phenoxy)-pyridin-3-yl]-(2-methyl-3,4-dihydro-2H-quinolin-1-yl)-methanone,
[2-(2,5-dichloro-phenoxy)-pyridin-3-yl]-(8-fluoro-6-methyl-3,4-dihydro-2H-quinolin-1-yl)-methanone,
N-(2-chloro-4-methyl-pyridin-3-yl)-2-(2,5-dichloro-phenoxy)-N-methyl-nicotinamide,
[2-(2,5-dichloro-phenoxy)-pyridin-3-yl]-(8-methoxy-3,4-dihydro-2H-quinolin-1-yl)-methanone,
(6-chloro-3,4-dihydro-2H-quinolin-1-yl)-[2-(2,5-dichloro-phenoxy)-pyridin-3-yl]-methanone,
[2-(2,5-dichloro-phenoxy)-pyridin-3-yl]-(6-fluoro-2,3-dihydro-benzo[1,4]oxazin-4-yl)-methanone,
[2-(2,5-dichloro-phenoxy)-pyridin-3-yl]-(6,8-difluoro-2,3-dihydro-benzo[1,4]oxazin-4-yl)-methanone,
[2-(2,5-dichloro-phenoxy)-pyridin-3-yl]-(4-phenyl-3,4-dihydro-2H-quinoxalin-1-yl)-methanone,
2-(2,5-dichloro-phenoxy)-N-(4-methoxy-pyridin-3-yl)-N-methyl-nicotinamide,
[2-(2,4-dichloro-phenoxy)-pyridin-3-yl]-(3,4-dihydro-2H-quinolin-1-yl)-methanone,
[2-(3-chloro-4-fluoro-phenoxy)-pyridin-3-yl]-(6-methyl-3,4-dihydro-2H-quinolin-1-yl)-methanone,
[2-(3-chloro-4-fluoro-phenoxy)-pyridin-3-yl]-(3,4-dihydro-2H-[1,5]naphthyridin-1-yl)-methanone,
[2-(3-chloro-4-fluoro-phenoxy)-pyridin-3-yl]-(6,7-difluoro-3,4-dihydro-2H-quinolin-1-yl)-methanone,
[2-(2,5-dichloro-phenoxy)-5-fluoro-pyridin-3-yl]-(2-methyl-3,4-dihydro-2H-quinolin-1-yl)-methanone,
[2-(2,5-dichloro-phenoxy)-5-fluoro-pyridin-3-yl]-(2,3-dihydro-benzo[1,4]oxazin-4-yl)-methanone,
1-[2-(2,5-dichloro-phenoxy)-5-fluoro-pyridine-3-carbonyl]-1,2,3,4-tetrahydro-benzo[b]azepin-5-one,
[2-(2,5-dichloro-phenoxy)-5-fluoro-pyridin-3-yl]-(3,4-dihydro-2H-quinolin-1-yl)-methanone,
2-(2,5-dichloro-phenoxy)-N-ethyl-5-fluoro-N-phenyl-nicotinamide,
[2-(3-chloro-phenoxy)-5-fluoro-pyridin-3-yl]-(6,7-difluoro-3,4-dihydro-2H-quinolin-1-yl)-methanone,
[2-(3-chloro-4-fluoro-phenoxy)-5-fluoro-pyridin-3-yl]-(3,4-dihydro-2H-quinolin-1-yl)-methanone,
[2-(3-chloro-4-fluoro-phenoxy)-5-fluoro-pyridin-3-yl]-(6,7-difluoro-3,4-dihydro-2H-quinolin-1-yl)-methanone,
[2-(3-chloro-4-fluoro-phenoxy)-5-fluoro-pyridin-3-yl]-(8-methyl-3,4-dihydro-2H-quinolin-1-yl)-methanone,
[3-(2,5-dichloro-phenoxy)-pyridin-4-yl]-(3,4-dihydro-2H-quinolin-1-yl)-methanone,
[3-(2,5-dichloro-phenoxy)-pyridin-4-yl]-(7-fluoro-3,4-dihydro-2H-quinolin-1-yl)-methanone,
[3-(2,5-dichloro-phenoxy)-pyridin-4-yl]-(6-fluoro-3,4-dihydro-2H-quinolin-1-yl)-methanone,
[3-(2,5-dichloro-phenoxy)-pyridin-4-yl]-(6,8-difluoro-3,4-dihydro-2H-quinolin-1-yl)-methanone,
3-(2,5-dichloro-phenoxy)-N-methyl-N-o-tolyl-isonicotinamide,
N-(2-chloro-phenyl)-3-(2,5-dichloro-phenoxy)-N-methyl-isonicotinamide,
3-(2,5-dichloro-phenoxy)-N-(2-methoxy-phenyl)-N-methyl-isonicotinamide,
[3-(2,4-dichloro-phenoxy)-pyridin-4-yl]-(7-fluoro-3,4-dihydro-2H-quinolin-1-yl)-methanone,
[3-(2,4-dichloro-phenoxy)-pyridin-4-yl]-(6-fluoro-3,4-dihydro-2H-quinolin-1-yl)-methanone,

[3-(2,4-dichloro-phenoxy)-pyridin-4-yl]-(6,8-difluoro-3,4-dihydro-2H-quinolin-1-yl)-methanone,
3-(2,4-dichloro-phenoxy)-N-methyl-N-o-tolyl-isonicotinamide,
N-(2-chloro-phenyl)-3-(2,4-dichloro-phenoxy)-N-methyl-isonicotinamide,
3-(2,4-dichloro-phenoxy)-N-(2-methoxy-phenyl)-N-methyl-isonicotinamide,
3-(2,4-dichloro-phenoxy)-N-(2-methoxy-pyridin-3-yl)-N-methyl-isonicotinamide,
[3-(3-chloro-4-fluoro-phenoxy)-pyridin-4-yl]-(7-fluoro-3,4-dihydro-2H-quinolin-1-yl)-methanone,
[3-(3-chloro-4-fluoro-phenoxy)-pyridin-4-yl]-(6-fluoro-3,4-dihydro-2H-quinolin-1-yl)-methanone,
[3-(3-chloro-4-fluoro-phenoxy)-pyridin-4-yl]-(6,8-difluoro-3,4-dihydro-2H-quinolin-1-yl)-methanone,
3-(3-chloro-4-fluoro-phenoxy)-N-methyl-N-o-tolyl-isonicotinamide,
3-(3-chloro-4-fluoro-phenoxy)-N-(2-chloro-phenyl)-N-methyl-isonicotinamide,
3-(3-chloro-4-fluoro-phenoxy)-N-(2-methoxy-phenyl)-N-methyl-isonicotinamide,
3-(3-chloro-4-fluoro-phenoxy)-N-(2-methoxy-pyridin-3-yl)-N-methyl-isonicotinamide,
[2-(2,5-dichloro-phenoxy)-phenyl]-(3,4-dihydro-2H-quinolin-1-yl)-methanone,
[2-(2,5-dichloro-phenoxy)-phenyl]-(6,7-difluoro-3,4-dihydro-2H-quinolin-1-yl)-methanone,
[2-(2,5-dichloro-phenoxy)-phenyl]-(2-methyl-2,3-dihydro-indol-1-yl)-methanone,
[2-(2,5-dichloro-phenoxy)-5-fluoro-phenyl]-(3,4-dihydro-2H-quinolin-1-yl)-methanone,
[2-(2,5-dichloro-phenoxy)-5-fluoro-phenyl]-(2-methyl-3,4-dihydro-2H-quinolin-1-yl)-methanone,
[2-(2,5-dichloro-phenoxy)-5-fluoro-phenyl]-(8-methyl-3,4-dihydro-2H-quinolin-1-yl)-methanone,
[2-(2,5-dichloro-phenoxy)-5-fluoro-phenyl]-(6-methyl-3,4-dihydro-2H-quinolin-1-yl)-methanone,
[2-(2,5-dichloro-phenoxy)-5-fluoro-phenyl]-(2,3-dihydro-benzo[1,4]oxazin-4-yl)-methanone,
2-(2,5-dichloro-phenoxy)-5-fluoro-N-methyl-N-phenyl-benzamide,
4-(2,5-dichloro-phenoxy)-3-(3,4-dihydro-2H-quinoline-1-carbonyl)-benzonitrile,
[2-(2,5-dichloro-phenoxy)-phenyl]-(8-fluoro-6-methyl-3,4-dihydro-2H-quinolin-1-yl)-methanone, and
[2-(2,5-dichloro-phenoxy)-phenyl]-(6,8-difluoro-3,4-dihydro-2H-quinolin-1-yl)-methanone,
or pharmaceutically acceptable salts thereof.

2. A compound, selected from the group consisting of:
[2-(2,5-dichloro-phenoxy)-pyridin-3-yl]-(3,4-dihydro-2H-quinoxalin-1-yl)-methanone,
[2-(2,5-dichloro-phenoxy)-pyridin-3-yl]-(4-methyl-3,4-dihydro-2H-quinoxalin-1-yl)-methanone,
[2-(2,5-dichloro-phenoxy)-pyridin-3-yl]-(4-isopropyl-3,4-dihydro-2H-quinoxalin-1-yl)-methanone,
(4-cyclopropyl-3,4-dihydro-2H-quinoxalin-1-yl)-[2-(2,5-dichloro-phenoxy)-pyridin-3-yl]-methanone,
(4-cyclobutyl-3,4-dihydro-2H-quinoxalin-1-yl)-[2-(2,5-dichloro-phenoxy)-pyridin-3-yl]-methanone,
[2-(2,5-dichloro-phenoxy)-pyridin-3-yl]-(4-oxetan-3-yl-3,4-dihydro-2H-quinoxalin-1-yl)-methanone,
1-[2-(2,5-dichloro-phenoxy)-pyridine-3-carbonyl]-2,3-dihydro-1H-quinolin-4-one,
[2-(2,5-dichloro-phenoxy)-pyridin-3-yl]-(4-methylene-3,4-dihydro-2H-quinolin-1-yl)-methanone,
[2-(2,5-dichloro-phenoxy)-pyridin-3-yl]-[4-(3,3-difluoro-azetidin-1-yl)-3,4-dihydro-2H-quinolin-1-yl]-methanone,
N-(2-cyclopropyl-phenyl)-2-(2,5-dichloro-phenoxy)-N-methyl-nicotinamide,
2-(2,5-dichloro-phenoxy)-N-methyl-N-(2-methylsulfanyl-phenyl)-nicotinamide,
2-(2,5-dichloro-phenoxy)-N-methyl-N-[2-(2-methyl-2H-pyrazol-3-yl)-phenyl]-nicotinamide,
N-(2-amino-phenyl)-2-(2,5-dichloro-phenoxy)-N-methyl-nicotinamide,
2-(2,5-dichloro-phenoxy)-N-(2,5-dichloro-phenyl)-N-methyl-nicotinamide,
[2-(2,5-dichloro-phenoxy)-pyridin-3-yl]-(2,3,3a,4-tetrahydro-1H-pyrrolo[1,2-a]quinoxalin-5-yl-methanone,
[2-(2,5-dichloro-phenoxy)-pyridin-3-yl]-(4-isobutyl-3,4-dihydro-2H-quinoxalin-1-yl)-methanone,
(4-cyclopropylmethyl-3,4-dihydro-2H-quinoxalin-1-yl)-[2-(2,5-dichloro-phenoxy)-pyridin-3-yl]-methanone,
(4-cyclobutylmethyl-3,4-dihydro-2H-quinoxalin-1-yl)-[2-(2,5-dichloro-phenoxy)-pyridin-3-yl]-methanone,
acetic acid 2-{4-[2-(2,5-dichloro-phenoxy)-pyridine-3-carbonyl]-3,4-dihydro-2H-quinoxalin-1-yl}-ethyl ester,
{4-[2-(2,5-dichloro-phenoxy)-pyridine-3-carbonyl]-3,4-dihydro-2H-quinoxalin-1-yl}-acetic acid ethyl ester,
{4-[2-(2,5-dichloro-phenoxy)-pyridine-3-carbonyl]-3,4-dihydro-2H-quinoxalin-1-yl}-acetic acid,
3-(4-{4-[2-(2,5-dichloro-phenoxy)-pyridine-3-carbonyl]-3,4-dihydro-2H-quinoxaline-1-sulfonyl}-phenyl)-propionic acid,
(3,4-dihydro-2H-quinolin-1-yl)-[2-(2-fluoro-5-trifluoromethyl-phenoxy)-pyridin-3-yl]-methanone,
2-(2,5-dichloro-phenoxy)-5-fluoro-N-(2-methoxy-pyridin-3-yl)-N-methyl-nicotinamide,
N-(2,6-dichloro-3-methoxy-phenyl)-2-(2,5-dichloro-phenoxy)-5-fluoro-N-methyl-nicotinamide,
[2-(2,5-dichloro-phenoxy)-5-fluoro-pyridin-3-yl]-(3,4-dihydro-2H-quinoxalin-1-yl)-methanone,
1-[2-(2,5-dichloro-phenoxy)-5-fluoro-pyridine-3-carbonyl]-1,2,3,4-tetrahydro-quinoline-4-carboxylic acid methyl ester,
[2-(2,5-dichloro-phenoxy)-5-fluoro-pyridin-3-yl]-(4H-pyrrolo[1,2-a]quinoxalin-5-yl)-methanone,
(4-cyclobutyl-3,4-dihydro-2H-quinoxalin-1-yl)-[2-(2,5-dichloro-phenoxy)-5-fluoro-pyridin-3-yl]-methanone,
[2-(2,5-dichloro-phenoxy)-5-fluoro-pyridin-3-yl]-(4-furan-3-ylmethyl-3,4-dihydro-2H-quinoxalin-1-yl)-methanone,
(4-cyclobutylmethyl-3,4-dihydro-2H-quinoxalin-1-yl)-[2-(2,5-dichloro-phenoxy)-5-fluoro-pyridin-3-yl]-methanone,
[2-(2,5-dichloro-phenoxy)-5-fluoro-pyridin-3-yl]-[4-(3,3,3-trifluoro-propyl)-3,4-dihydro-2H-quinoxalin-1-yl]-methanone,
{4-[2-(2,5-dichloro-phenoxy)-5-fluoro-pyridine-3-carbonyl]-3,4-dihydro-2H-quinoxalin-1-yl}-acetic acid ethyl ester,
{4-[2-(2,5-dichloro-phenoxy)-5-fluoro-pyridine-3-carbonyl]-3,4-dihydro-2H-quinoxalin-1-yl}-acetic acid,
3-{4-[2-(2,5-dichloro-phenoxy)-5-fluoro-pyridine-3-carbonyl]-3,4-dihydro-2H-quinoxalin-1-yl}-propionic acid ethyl ester,
3-{4-[2-(2,5-dichloro-phenoxy)-5-fluoro-pyridine-3-carbonyl]-3,4-dihydro-2H-quinoxalin-1-yl}-2-methyl-propionic acid, 4-{4-[2-(2,5-dichloro-phenoxy)-5-fluoro-pyridine-3-carbonyl]-3,4-dihydro-2H-quinoxalin-1-yl}-butyric acid ethyl ester,
5-{4-[2-(2,5-dichloro-phenoxy)-5-fluoro-pyridine-3-carbonyl]-3,4-dihydro-2H-quinoxalin-1-yl}-pentanoic acid ethyl ester,
6-{4-[2-(2,5-dichloro-phenoxy)-5-fluoro-pyridine-3-carbonyl]-3,4-dihydro-2H-quinoxalin-1-yl}-hexanoic acid methyl ester,
6-{4-[2-(2,5-dichloro-phenoxy)-5-fluoro-pyridine-3-carbonyl]-3,4-dihydro-2H-quinoxalin-1-yl}-hexanoic acid,
4-{4-[2-(2,5-dichloro-phenoxy)-5-fluoro-pyridine-3-carbonyl]-3,4-dihydro-2H-quinoxaline-1-carbonyl}-benzoic acid methyl ester,
[2-(4-bromo-2,5-dichloro-phenoxy)-pyridin-3-yl]-(4-cyclopropyl-3,4-dihydro-2H-quinoxalin-1-yl)-methanone,
(4-cyclopropyl-3,4-dihydro-2H-quinoxalin-1-yl)-{2-[2,5-dichloro-4-(3-hydroxy-prop-1-ynyl)-phenoxy]-pyridin-3-yl}-methanone,
[2-(4-bromo-2,5-dichloro-phenoxy)-pyridin-3-yl]-(3,4-dihydro-2H-quinolin-1-yl)-methanone,
5-{2,5-dichloro-4-[3-(3,4-dihydro-2H-quinoline-1-carbonyl)-pyridin-2-yloxy]-phenyl}-pent-4-ynoic acid methyl ester,
2-chloro-4-{2,5-dichloro-4-[3-(4-cyclopropyl-3,4-dihydro-2H-quinoxaline-1-carbonyl)-pyridin-2-yloxy]-phenylethynyl}-benzoic acid methyl ester,
2-chloro-4-{2,5-dichloro-4-[3-(4-cyclopropyl-3,4-dihydro-2H-quinoxaline-1-carbonyl)-pyridin-2-yloxy]-phenylethynyl}-benzoic acid,
2-chloro-4-(2-{2,5-dichloro-4-[3-(4-cyclopropyl-3,4-dihydro-2H-quinoxaline-1-carbonyl)-pyridin-2-yloxy]-phenyl}-ethyl)-benzoic acid,
4-(2-{2,5-dichloro-4-[3-(4-cyclopropyl-3,4-dihydro-2H-quinoxaline-1-carbonyl)-pyridin-2-yloxy]-phenyl}-ethyl)-benzoic acid,
4-(2-{2,5-dichloro-4-[3-(4-cyclopropyl-3,4-dihydro-2H-quinoxaline-1-carbonyl)-pyridin-2-yloxy]-phenyl}-ethyl)-3-methoxy-benzoic acid,
3-{2,5-dichloro-4-[3-(4-cyclopropyl-3,4-dihydro-2H-quinoxaline-1-carbonyl)-pyridin-2-yloxy]-phenyl}-acrylic acid,
3-{2,5-dichloro-4-[3-(4-cyclopropyl-3,4-dihydro-2H-quinoxaline-1-carbonyl)-pyridin-2-yloxy]-phenyl}-propionic acid,
4-{2,5-dichloro-4-[3-(4-cyclopropyl-3,4-dihydro-2H-quinoxaline-1-carbonyl)-pyridin-2-yloxy]-phenyl}-but-3-enoic acid methyl ester,
4-{2,5-dichloro-4-[3-(4-cyclopropyl-3,4-dihydro-2H-quinoxaline-1-carbonyl)-pyridin-2-yloxy]-phenyl}-but-3-enoic acid,
4-{2,5-dichloro-4-[3-(4-cyclopropyl-3,4-dihydro-2H-quinoxaline-1-carbonyl)-pyridin-2-yloxy]-phenyl}-butyric acid,
(3-{2,5-dichloro-4-[3-(4-cyclopropyl-3,4-dihydro-2H-quinoxaline-1-carbonyl)-pyridin-2-yloxy]-phenyl}-propionylamino)-acetic acid,
[(3-{2,5-dichloro-4-[3-(4-cyclopropyl-3,4-dihydro-2H-quinoxaline-1-carbonyl)-pyridin-2-yloxy]-phenyl}-propionyl)-methyl-amino]-acetic acid,
3-(3-{2,5-dichloro-4-[3-(4-cyclopropyl-3,4-dihydro-2H-quinoxaline-1-carbonyl)-pyridin-2-yloxy]-phenyl}-propionylamino)-propionic acid,
1-(3-{2,5-dichloro-4-[3-(4-cyclopropyl-3,4-dihydro-2H-quinoxaline-1-carbonyl)-pyridin-2-yloxy]-phenyl}-propionyl)-pyrrolidine-2-carboxylic acid,
3-(4-{2,5-dichloro-4-[3-(4-cyclopropyl-3,4-dihydro-2H-quinoxaline-1-carbonyl)-pyridin-2-yloxy]-phenyl}-butyrylamino)-propionic acid,
2,5-dichloro-4-[3-(4-cyclopropyl-3,4-dihydro-2H-quinoxaline-1-carbonyl)-pyridin-2-yloxy]benzoic acid methyl ester,
{2,5-dichloro-4-[3-(4-cyclopropyl-3,4-dihydro-2H-quinoxaline-1-carbonyl)-pyridin-2-yloxy]-benzoylamino}-acetic acid methyl ester,
(4-cyclopropyl-3,4-dihydro-2H-quinoxalin-1-yl)-[2-(2,5-dichloro-phenoxy)-phenyl]-methanone, and
[3-(2,5-dichloro-phenoxy)-pyridin-4-yl]-(2,3-dihydro-benzo[1,4]oxazin-4-yl)-methanone,
or pharmaceutically acceptable salts thereof.

3. A compound, selected from the group consisting of:
[2-(3-chloro-4-fluoro-phenoxy)-pyridin-3-yl]-(3,4-dihydro-2H-quinolin-1-yl)-methanone,
[2-(2,5-dichloro-phenoxy)-pyridin-3-yl]-(3,4-dihydro-2H-quinolin-1-yl)-methanone,
2-(2,5-dichloro-phenoxy)-N-ethyl-N-phenyl-nicotinamide,
[2-(2,5-dichloro-phenoxy)-pyridin-3-yl]-(7-fluoro-3,4-dihydro-2H-quinolin-1-yl)-methanone,
[2-(2,5-dichloro-phenoxy)-pyridin-3-yl]-(6-fluoro-3,4-dihydro-2H-quinolin-1-yl)-methanone,
[2-(2,5-dichloro-phenoxy)-pyridin-3-yl]-(6,7-difluoro-3,4-dihydro-2H-quinolin-1-yl)-methanone,
[2-(2,5-dichloro-phenoxy)-pyridin-3-yl]-(2,3-dihydro-benzo[1,4]thiazin-4-yl)-methanone,
2-(2,5-dichloro-phenoxy)-N-methyl-N-o-tolyl-nicotinamide,
2-(2,5-dichloro-phenoxy)-N-(2-methoxy-phenyl)-N-methyl-nicotinamide,
[2-(2,5-dichloro-phenoxy)-pyridin-3-yl]-(6,8-difluoro-3,4-dihydro-2H-quinolin-1-yl)-methanone,
N-(2-chloro-6-methyl-phenyl)-2-(2,5-dichloro-phenoxy)-N-methyl-nicotinamide,
2-(2,5-dichloro-phenoxy)-N-(5-fluoro-2-methoxy-phenyl)-N-methyl-nicotinamide,
[2-(2,5-dichloro-phenoxy)-5-fluoro-pyridin-3-yl]-(3,4-dihydro-2H-quinolin-1-yl)-methanone,
[3-(2,5-dichloro-phenoxy)-pyridin-4-yl]-(3,4-dihydro-2H-quinolin-1-yl)-methanone,
[3-(2,5-dichloro-phenoxy)-pyridin-4-yl]-(7-fluoro-3,4-dihydro-2H-quinolin-1-yl)-methanone,
[3-(2,5-dichloro-phenoxy)-pyridin-4-yl]-(6-fluoro-3,4-dihydro-2H-quinolin-1-yl)-methanone,
[3-(2,5-dichloro-phenoxy)-pyridin-4-yl]-(6,8-difluoro-3,4-dihydro-2H-quinolin-1-yl)-methanone,
3-(2,5-dichloro-phenoxy)-N-methyl-N-o-tolyl-isonicotinamide,
3-(2,5-dichloro-phenoxy)-N-(2-methoxy-phenyl)-N-methyl-isonicotinamide,
[2-(2,5-dichloro-phenoxy)-phenyl]-(3,4-dihydro-2H-quinolin-1-yl)-methanone,
[2-(2,5-dichloro-phenoxy)-pyridin-3-yl]-(3,4-dihydro-2H-quinoxalin-1-yl)-methanone,
[2-(2,5-dichloro-phenoxy)-pyridin-3-yl]-(4-methyl-3,4-dihydro-2H-quinoxalin-1-yl)-methanone,
(4-cyclopropyl-3,4-dihydro-2H-quinoxalin-1-yl)-[2-(2,5-dichloro-phenoxy)-pyridin-3-yl]-methanone,
(4-cyclobutyl-3,4-dihydro-2H-quinoxalin-1-yl)-[2-(2,5-dichloro-phenoxy)-pyridin-3-yl]-methanone,

[2-(2,5-dichloro-phenoxy)-pyridin-3-yl]-(4-oxetan-3-yl-3,4-dihydro-2H-quinoxalin-1-yl)-methanone,
[2-(2,5-dichloro-phenoxy)-pyridin-3-yl]-(4-methylene-3,4-dihydro-2H-quinolin-1-yl)-methanone,
2-(2,5-dichloro-phenoxy)-N-methyl-N-(2-methylsulfanyl-phenyl)-nicotinamide,
(4-cyclopropylmethyl-3,4-dihydro-2H-quinoxalin-1-yl)-[2-(2,5-dichloro-phenoxy)-pyridin-3-yl]-methanone,
[2-(2,5-dichloro-phenoxy)-5-fluoro-pyridin-3-yl]-(3,4-dihydro-2H-quinoxalin-1-yl)-methanone,
(4-cyclobutyl-3,4-dihydro-2H-quinoxalin-1-yl)-[2-(2,5-dichloro-phenoxy)-5-fluoro-pyridin-3-yl]-methanone,
{4-[2-(2,5-dichloro-phenoxy)-5-fluoro-pyridine-3-carbonyl]-3,4-dihydro-2H-quinoxalin-1-yl}-acetic acid ethyl ester,
[2-(4-bromo-2,5-dichloro-phenoxy)-pyridin-3-yl]-(4-cyclopropyl-3,4-dihydro-2H-quinoxalin-1-yl)-methanone,
(4-cyclopropyl-3,4-dihydro-2H-quinoxalin-1-yl)-{2-[2,5-dichloro-4-(3-hydroxy-prop-1-ynyl)-phenoxy]-pyridin-3-yl}-methanone,
4-(2-{2,5-dichloro-4-[3-(4-cyclopropyl-3,4-dihydro-2H-quinoxaline-1-carbonyl)-pyridin-2-yloxy]-phenyl}-ethyl)-benzoic acid,
3-{2,5-dichloro-4-[3-(4-cyclopropyl-3,4-dihydro-2H-quinoxaline-1-carbonyl)-pyridin-2-yloxy]-phenyl}-propionic acid,
4-{2,5-dichloro-4-[3-(4-cyclopropyl-3,4-dihydro-2H-quinoxaline-1-carbonyl)-pyridin-2-yloxy]-phenyl}-but-3-enoic acid methyl ester,
(3-{2,5-dichloro-4-[3-(4-cyclopropyl-3,4-dihydro-2H-quinoxaline-1-carbonyl)-pyridin-2-yloxy]-phenyl}-propionylamino)-acetic acid,
[(3-{2,5-dichloro-4-[3-(4-cyclopropyl-3,4-dihydro-2H-quinoxaline-1-carbonyl)-pyridin-2-yloxy]-phenyl}-propionyl)-methyl-amino]-acetic acid,
3-(3-{2,5-dichloro-4-[3-(4-cyclopropyl-3,4-dihydro-2H-quinoxaline-1-carbonyl)-pyridin-2-yloxy]-phenyl}-propionylamino)-propionic acid,
1-(3-{2,5-dichloro-4-[3-(4-cyclopropyl-3,4-dihydro-2H-quinoxaline-1-carbonyl)-pyridin-2-yloxy]-phenyl}-propionyl)-pyrrolidine-2-carboxylic acid,
3-(4-{2,5-dichloro-4-[3-(4-cyclopropyl-3,4-dihydro-2H-quinoxaline-1-carbonyl)-pyridin-2-yloxy]-phenyl}-butyrylamino)-propionic acid,
(4-cyclopropyl-3,4-dihydro-2H-quinoxalin-1-yl)-[2-(2,5-dichloro-phenoxy)-phenyl]-methanone,
[3-(2,5-dichloro-phenoxy)-pyridin-4-yl]-(2,3-dihydro-benzo[1,4]oxazin-4-yl)-methanone, and
or pharmaceutically acceptable salts thereof.

\* \* \* \* \*